United States Patent
Burgard et al.

(10) Patent No.: US 10,087,470 B2
(45) Date of Patent: Oct. 2, 2018

(54) METHODS FOR INCREASING PRODUCT YIELDS

(71) Applicant: Genomatica, Inc., San Diego, CA (US)

(72) Inventors: Anthony P. Burgard, Bellefonte, PA (US); Robin E. Osterhout, San Diego, CA (US); Jun Sun, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 14/806,435

(22) Filed: Jul. 22, 2015

(65) Prior Publication Data

US 2016/0145652 A1 May 26, 2016

Related U.S. Application Data

(63) Continuation of application No. 13/889,056, filed on May 7, 2013, now abandoned, which is a continuation of application No. 13/011,788, filed on Jan. 21, 2011, now Pat. No. 8,445,244.

(60) Provisional application No. 61/307,437, filed on Feb. 23, 2010, provisional application No. 61/314,570, filed on Mar. 16, 2010.

(51) Int. Cl.
| | |
|---|---|
| *C12N 9/08* | (2006.01) |
| *C12P 7/42* | (2006.01) |
| *C12N 9/02* | (2006.01) |
| *C12P 7/04* | (2006.01) |
| *C12P 7/16* | (2006.01) |
| *C12P 7/52* | (2006.01) |
| *C12P 7/18* | (2006.01) |

(52) U.S. Cl.
CPC .............. *C12P 7/42* (2013.01); *C12N 9/0008* (2013.01); *C12N 9/0095* (2013.01); *C12P 7/04* (2013.01); *C12P 7/16* (2013.01); *C12P 7/18* (2013.01); *C12P 7/52* (2013.01); Y02E 50/10 (2013.01)

(58) Field of Classification Search
CPC .. C12N 9/08; C12Y 102/99002; C12Y 102/02
See application file for complete search history.

(56) References Cited

U.S. PATENT DOCUMENTS 8,129,155 B2 * 3/2012 Trawick ............... C12N 9/0006
435/146

OTHER PUBLICATIONS

Murphy et al. 1967; Malate dehydrogenase. II. Purification and properties of Bacillus subtilis, Bacillus stearothermophilus, and *Escherichia coli* malate dehydrogenases. J. Biol. Chem. 242(7): 1548-1559.*

* cited by examiner

*Primary Examiner* — Karen Cochrane Carlson
(74) *Attorney, Agent, or Firm* — Jones Day

(57) ABSTRACT

A non-naturally occurring microbial organism includes a microbial organism having a reductive TCA or Wood-Ljungdahl pathway in which at least one exogenous nucleic acid encoding these pathway enzymes is expressed in a sufficient amount to enhance carbon flux through acetyl-CoA. A method for enhancing carbon flux through acetyl-CoA includes culturing theses non-naturally occurring microbial organisms under conditions and for a sufficient period of time to produce a product having acetyl-CoA as a building block. Another non-naturally occurring microbial organism includes at least one exogenous nucleic acid encoding an enzyme expressed in a sufficient amount to enhance the availability of reducing equivalents in the presence of carbon monoxide or hydrogen, thereby increasing the yield of redox-limited products via carbohydrate-based carbon feedstock. A method for enhancing the availability of reducing equivalents in the presence of carbon monoxide or hydrogen includes culturing this organism for a sufficient period of time to produce a product.

4 Claims, 22 Drawing Sheets

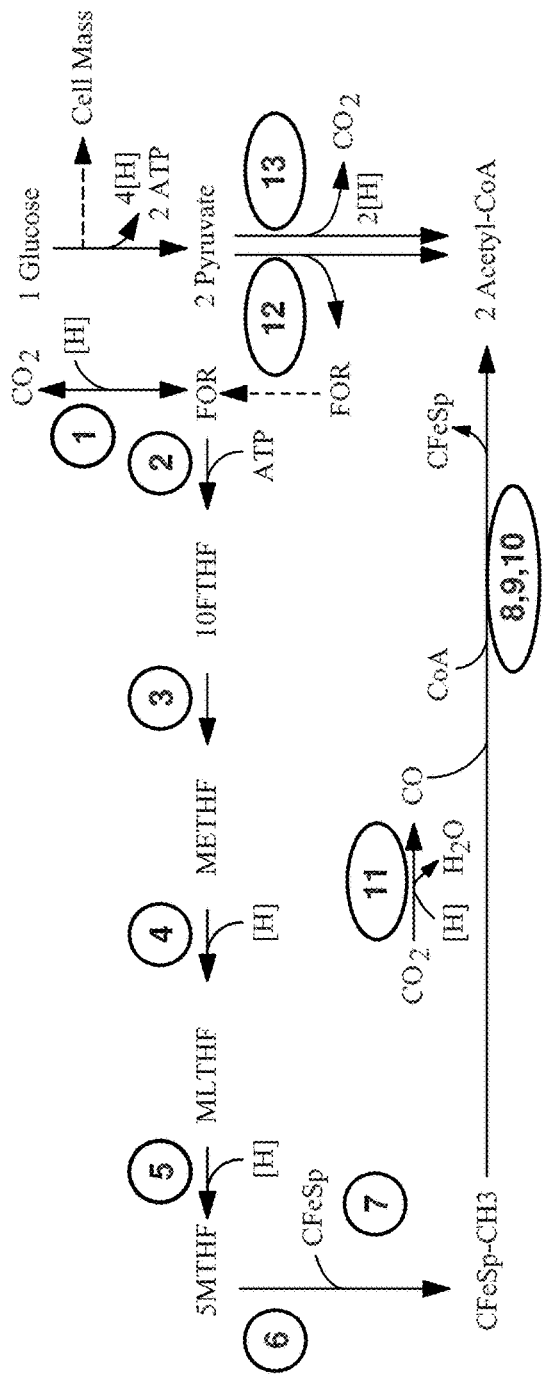

FIG. 4A

1) Formate dehydrogenase
2) Formyltetrahydrofolate synthetase
3) Methenyltetrahydrofolate cyclohydrolase
4) Methylenetetrahydrofolate dehydrogenase
5) Methylenetetrahydrofolate reductase
6) Methyltetrahydrofolate:corrinoid protein methyltranferase (AcsE)
7) Corrinoid iron-sulfur protein (AcsD)
8) Nickel-protein assembly protein (AcsF & CooC)
9) Ferredoxin (Orf7)
10) Acetyl-CoA synthase (AcsB & AcsC)
11) Carbon monoxide dehydrogenase (AcsA)
12) Pyruvate formate lyase (Pfl)
13) Pyruvate ferredoxin oxidoreductase (Por) or pyruvate dehydrogenase (PDH)

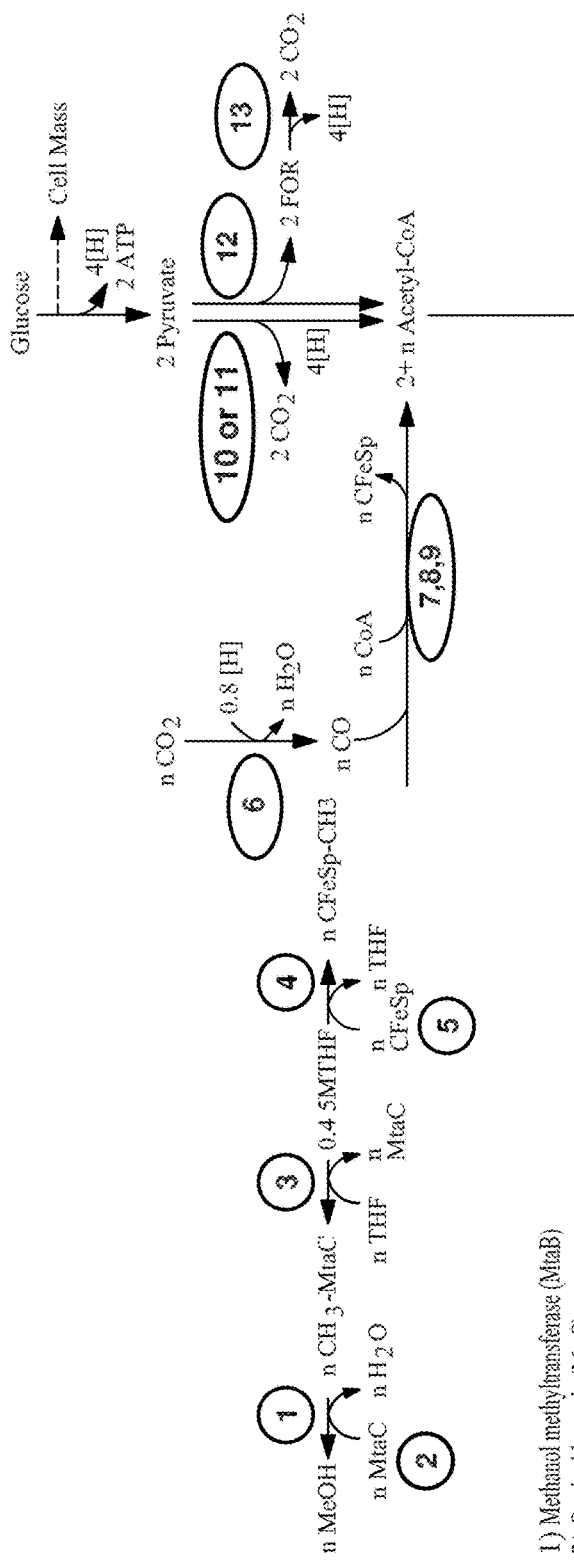

FIG. 4B

1) Methanol methyltransferase (MtaB)
2) Corrinoid protein (MtaC)
3) Methyltetrahydrofolate:corrinoid protein methyltransferase (MtaA)
4) Methyltetrahydrofolate:corrinoid protein methyltransferase (AcsE)
5) Corrinoid iron-sulfur protein (AcsD)
6) Carbon monoxide dehydrogenase (AcsA)
7) Nickel-protein assembly protein (AcsF & CooC)
8) Ferredoxin (Orf7)
9) Acetyl-CoA synthase (AcsB & AcsC)
10) Pyruvate ferredoxin oxidoreductase (Por)
11) Pyruvate dehydrogenase (PDH)
12) Pyruvate formate lyase (Pfl)
13) Formate dehydrogenase

METHODS FOR INCREASING PRODUCT YIELDS

CROSS-REFERENCE TO RELATED APPLICATIONS

This application is a continuation of U.S. Ser. No. 13/889,056 filed May 7, 2013, which is a continuation of U.S. Ser. No. 13/011,788 filed Jan. 21, 2011 (now U.S. Pat. No. 8,445,244), which claims the benefit of priority under 35 U.S.C § 119(e) to U.S. Provisional Application 61/307,437, filed Feb. 23, 2010 and U.S. Provisional Application 61/314,570, filed Mar. 16, 2010, each of which is incorporated herein by reference in its entirety.

BACKGROUND OF THE INVENTION

This invention relates generally to biosynthetic processes and, more specifically to organisms having enhanced carbon fixation capabilities.

1,3-butanediol (1,3-BDO) is a four carbon diol traditionally produced from acetylene via its hydration. The resulting acetaldehyde is then converted to 3-hydroxybutyraldehdye which is subsequently reduced to form 1,3-BDO. More recently, acetylene has been replaced by the less expensive ethylene as a source of acetaldehyde. 1,3-BDO is commonly used as an organic solvent for food flavoring agents. It is also used as a co-monomer for polyurethane and polyester resins and is widely employed as a hypoglycemic agent. Optically active 1,3-BDO is a useful starting material for the synthesis of biologically active compounds and liquid crystals. Another use of 1,3-butanediol is that its dehydration affords 1,3-butadiene (Ichikawa et al. *Journal of Molecular Catalysis A-Chemical* 256:106-112 (2006); Ichikawa et al. *Journal of Molecular Catalysis A-Chemical* 231:181-189 (2005), which is useful in the manufacture synthetic rubbers (e.g., tires), latex, and resins. The reliance on petroleum based feedstocks for either acetylene or ethylene warrants the development of a renewable feedstock based route to 1,3-butanediol and to butadiene.

Isopropanol (IPA) is a colorless, flammable liquid that mixes completely with most solvents, including water. The largest use for IPA is as a solvent, including its well known yet small use as "rubbing alcohol," which is a mixture of IPA and water. As a solvent, IPA is found in many everyday products such as paints, lacquers, thinners, inks, adhesives, general-purpose cleaners, disinfectants, cosmetics, toiletries, de-icers, and pharmaceuticals. Low-grade IPA is also used in motor oils. IPA is also used as a chemical intermediate for the production of isopropylamines (Ag products), isopropylethers, and isopropyl esters. Isopropanol is manufactured by two petrochemical routes. The predominant process entails the hydration of propylene either with or without sulfuric acid catalysis. Secondarily, IPA is produced via hydrogenation of acetone, which is a by-product formed in the production of phenol and propylene oxide.

4-hydroxybutanoic acid (4-hydroxybutanoate, 4-hydroxybutyrate, 4-HB) is a 4-carbon carboxylic acid that is used as a building block for various commodity and specialty chemicals. In particular, 4-HB can serve as an entry point into the 1,4-butanediol family of chemicals, which includes solvents, resins, polymer precursors, and specialty chemicals.

1,4-butanediol (BDO) is a valuable chemical for the production of high performance polymers, solvents, and fine chemicals. It is the basis for producing other high value chemicals such as tetrahydrofuran (THF) and gamma-butyrolactone (GBL). The value chain is comprised of three main segments including: (1) polymers, (2) THF derivatives, and (3) GBL derivatives. In the case of polymers, BDO is a comonomer for polybutylene terephthalate (PBT) production. PBT is a medium performance engineering thermoplastic used in automotive, electrical, water systems, and small appliance applications. Conversion to THF, and subsequently to polytetramethylene ether glycol (PTMEG), provides an intermediate used to manufacture spandex products such as LYCRA® fibers. PTMEG is also combined with BDO in the production of specialty polyester ethers (COPE). COPEs are high modulus elastomers with excellent mechanical properties and oil/environmental resistance, allowing them to operate at high and low temperature extremes. PTMEG and BDO also make thermoplastic polyurethanes processed on standard thermoplastic extrusion, calendaring, and molding equipment, and are characterized by their outstanding toughness and abrasion resistance. The GBL produced from BDO provides the feedstock for making pyrrolidones, as well as serving the agrochemical market. The pyrrolidones are used as high performance solvents for extraction processes of increasing use, including for example, in the electronics industry and in pharmaceutical production.

BDO is produced by two main petrochemical routes with a few additional routes also in commercial operation. One route involves reacting acetylene with formaldehyde, followed by hydrogenation. More recently BDO processes involving butane or butadiene oxidation to maleic anhydride, followed by hydrogenation have been introduced. BDO is used almost exclusively as an intermediate to synthesize other chemicals and polymers.

Thus, there exists a need for the development of methods for effectively producing commercial quantities of compounds such as 1,4-butanediol, 4-hydroxybutyrate, 1,3-butanediol, or isopropanol. The present invention satisfies this need and provides related advantages as well. Additional product molecules that can be produced by the teachings of this invention include but are not limited to ethanol, butanol, isobutanol, isopropanol, succinic acid, fumaric acid, malic acid, 3-hydroxypropionic acid, lactic acid, adipic acid, 6-aminocaproic acid, hexamethylenediamine, caprolactam, 3-hydoxyisobutyric acid, 2-hydroxyisobutyric acid, methacrylic acid, acrylic acid, 1,3-propanediol, glycerol, and long chain hydrocarbons, alcohols, acids, and esters.

SUMMARY OF THE INVENTION

In some aspects, embodiments disclosed herein relate to a non-naturally occurring microbial organism that includes a microbial organism having a reductive TCA pathway which includes at least one exogenous nucleic acid encoding a reductive TCA pathway enzyme expressed in a sufficient amount to enhance carbon flux through acetyl-CoA. The at least one exogenous nucleic acid is selected from an ATP-citrate lyase, citrate lyase, a fumarate reductase, and an alpha-ketoglutarate:ferredoxin oxidoreductase. In some aspects, embodiments disclosed herein relate to a method for enhancing carbon flux through acetyl-CoA that includes culturing this non-naturally occurring microbial organism under conditions and for a sufficient period of time to produce a product having acetyl-CoA as a building block.

In some aspects, embodiments disclosed herein relate to a non-naturally occurring microbial organism that includes a microbial organism having a Wood-Ljungdahl pathway which includes at least one exogenous nucleic acid encoding a Wood-Ljungdahl pathway enzyme expressed in a sufficient amount to enhance carbon flux through acetyl-CoA. The at least one exogenous nucleic acid is selected from a) Formate dehydrogenase, b) Formyltetrahydrofolate synthetase, c) Methenyltetrahydrofolate cyclohydrolase, d) Methylenetetrahydrofolate dehydrogenase, e) Methylenetetrahydrofolate reductase, f) Methyltetrahydrofolate:corrinoid protein methyltransferase (AcsE), g) Corrinoid iron-sulfer protein (AcsD), h) Nickel-protein assembly protein (AcsF & CooC), i) Ferredoxin (Orf7), j) Acetyl-CoA synthase (AcsB & AcsC), k) Carbon monoxide dehydrogenase (AcsA), and l) Pyruvate ferredoxin oxidoreductase or pyruvate dehydrogenase, and m) pyruvate formate lyase. In some aspects, embodiments disclosed herein relate to a method for enhancing carbon flux through acetyl-CoA that includes culturing this non-naturally occurring microbial organism under conditions and for a sufficient period of time to produce a product having acetyl-CoA as a building block.

In some aspects, embodiments disclosed herein relate to a non-naturally occurring microbial organism that includes a microbial organism having a methanol Wood-Ljungdahl pathway which includes at least one exogenous nucleic acid encoding a methanol Wood-Ljungdahl pathway enzyme expressed in a sufficient amount to enhance carbon flux through acetyl-CoA. The at least one exogenous nucleic acid is selected from a) Methanol methyltransferase (MtaB), b) Corrinoid protein (MtaC), c) Methyltetrahydrofolate:corrinoid protein methyltransferase (MtaA), d) Methyltetrahydrofolate:corrinoid protein methyltransferase (AcsE), e) Corrinoid iron-sulfer protein (AcsD), f) Nickel-protein assembly protein (AcsF & CooC), g) Ferredoxin (Orf7), h) Acetyl-CoA synthase (AcsB & AcsC), i) Carbon monoxide dehydrogenase (AcsA), j) Pyruvate ferredoxin oxidoreductase or pyruvate dehydrogenase, k) pyruvate formate lyase, and l) NAD(P)H:ferredoxin oxidoreductase. In some aspects, embodiments disclosed herein relate to a method for enhancing carbon flux through acetyl-CoA, comprising culturing this non-naturally occurring microbial organism under conditions and for a sufficient period of time to produce a product having acetyl-CoA as a building block.

In some aspects, embodiments disclosed herein relate to a non-naturally occurring microbial organism that includes at least one exogenous nucleic acid encoding an enzyme expressed in a sufficient amount to enhance the availability of reducing equivalents in the presence of carbon monoxide or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin. In some aspects, embodiments disclosed herein relate to a method for enhancing the availability of reducing equivalents in the presence of carbon monoxide or hydrogen thereby increasing the yield of redox-limited products via carbohydrate-based carbon feedstock, the method includes culturing this non-naturally occurring microbial organism under conditions and for a sufficient period of time to produce a product.

In some aspects, embodiments disclosed herein relate to a non-naturally occurring microbial organism that includes a microbial organism having a reductive TCA pathway which includes at least one exogenous nucleic acid encoding a reductive TCA pathway enzyme. the at least one exogenous nucleic acid is selected from an ATP-citrate lyase, citrate lyase, a fumarate reductase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of 1) CO, 2) $CO_2$ and $H_2$, 3) CO and $CO_2$, 4) synthesis gas comprising CO and $H_2$, and 5) synthesis gas comprising CO, $CO_2$, and $H_2$.

In some aspects, embodiments disclosed herein relate to a method that includes culturing a non-naturally occurring microbial organism that includes a microbial organism having a reductive TCA pathway comprising at least one exogenous nucleic acid encoding a reductive TCA pathway enzyme. The at least one exogenous nucleic acid is selected from an ATP-citrate lyase, citrate lyase, a fumarate reductase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of 1) CO, 2) $CO_2$ and $H_2$, 3) CO and $CO_2$, 4) synthesis gas comprising CO and $H_2$, and 5) synthesis gas comprising CO, $CO_2$, and $H_2$ to produce a product.

BRIEF DESCRIPTION OF THE DRAWINGS

FIG. 4a shows a pathway for enabling carbon fixation from syngas into acetyl CoA. The reducing equivalents are derived from carbohydrates such as glucose. The enzymatic transformations are carried out by the following enzymes: 1) Formate dehydrogenase, 2) Formyltetrahydrofolate synthetase, 3) Methenyltetrahydrofolate cyclohydrolase, 4) Methylenetetrahydrofolate dehydrogenase, 5) Methylenetetrahydrofolate reductase, 6) Methyltetrahydrofolate:corrinoid protein methyltransferase (AcsE), 7) Corrinoid iron-sulfur protein (AcsD), 8) Nickel-protein assembly protein (AcsF & CooC), 9) Ferredoxin (Orf7), 10) Acetyl-CoA synthase (AcsB & AcsC), 11) Carbon monoxide dehydrogenase (AcsA), 12) Pyruvate formate lyase (Pfl), 13) Pyruvate ferredoxin oxidoreductase (Por) or pyruvate dehydrogenase (PDH).

FIG. 4b shows a pathway for enabling carbon fixation from methanol into acetyl CoA. The reducing equivalents are derived from carbohydrates such as glucose. "n" depicts the number of moles of methanol that are provided. The enzymatic transformations are carried out by the following enzymes: 1) Methanol methyltransferase (MtaB), 2) Corrinoid protein (MtaC), 3) Methyltetrahydrofolate:corrinoid protein methyltransferase (MtaA), 4) Methyltetrahydrofolate:corrinoid protein methyltransferase (AcsE), 5) Corrinoid iron-sulfur protein (AcsD), 6) Carbon monoxide dehydrogenase (AcsA), 7) Nickel-protein assembly protein (AcsF & CooC), 8) Ferredoxin (Orf7), 9) Acetyl-CoA synthase (AcsB & AcsC), 10) Pyruvate ferredoxin oxidoreductase (Por), 11) Pyruvate dehydrogenase (PDH), 12) Pyruvate formate lyase (Pfl), 13) Formate dehydrogenase

corrinoid protein methyltransferase (MtaA), 4) Methyltetrahydrofolate:corrinoid protein methyltransferase (AcsE), 5) Corrinoid iron-sulfur protein (AcsD), 6) Carbon monoxide dehydrogenase (AcsA), 7) Nickel-protein assembly protein (AcsF & CooC), 8) Ferredoxin (Orf7), 9) Acetyl-CoA synthase (AcsB & AcsC), 10) Pyruvate ferredoxin oxidoreductase (Por), 11) Pyruvate dehydrogenase (PDH), 12) Pyruvate formate lyase (Pfl), 13) Formate dehydrogenase, 14) Acetoacetyl-CoA thiolase (AtoB), 15) Acetoacetyl-CoA: acetate:CoA transferase (AtoAD), 16) Acetoacetate decarboxylase (Adc), and 17) Isopropanol dehydrogenase (Adh); when glucose and methanol are fed in 1.2 ratio, it provides an increase from 1 mol isopropanol/mol glucose to 2 mol isopropanol/mol glucose.

Figure 7A:
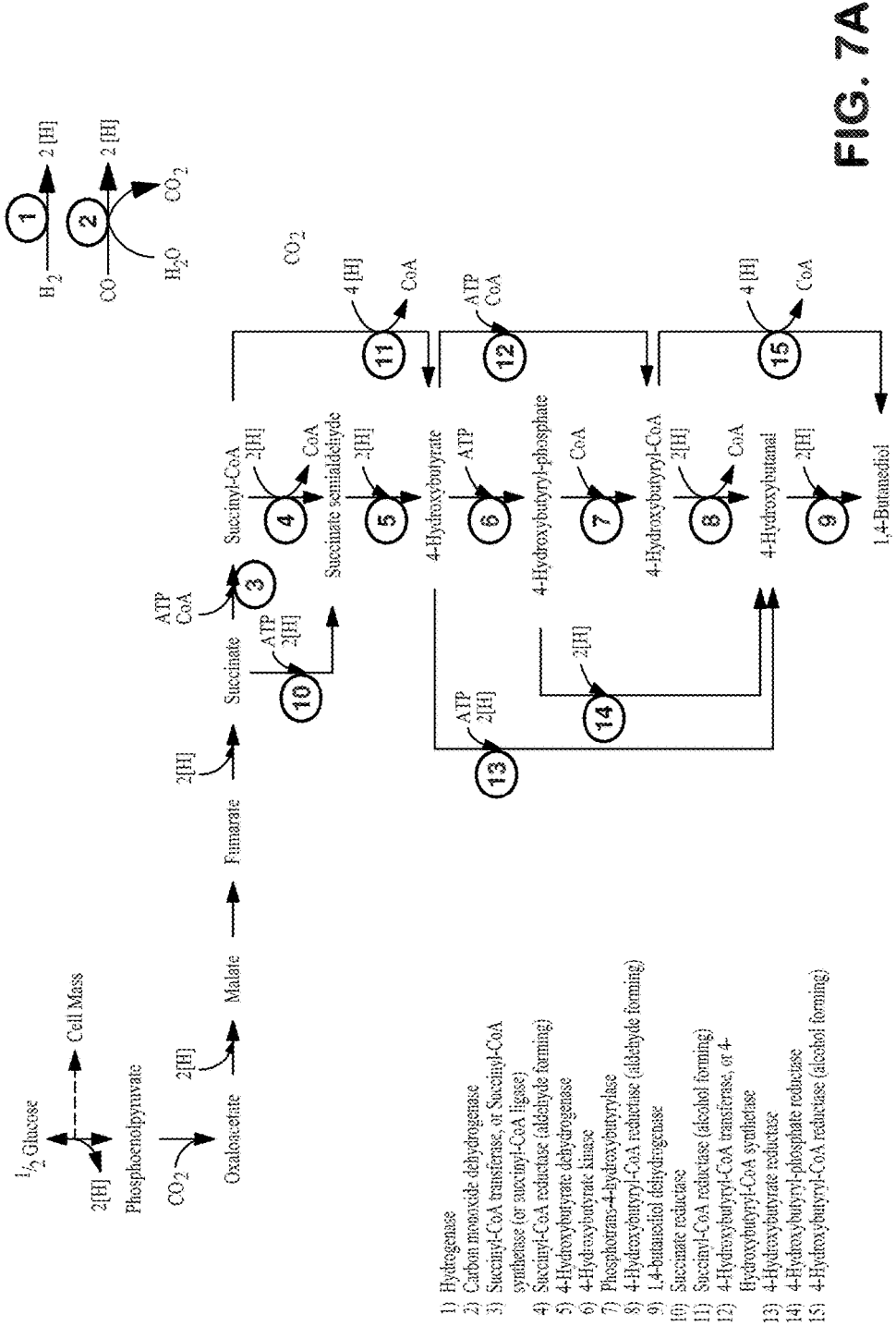

FIG. 7a shows flux distribution for improvement in 1,4-BDO yields from carbohydrates when reducing equivalents from syngas components are available; the enzymatic transformations shown are carried out by the following enzymes: 1) Hydrogenase, 2) Carbon monoxide dehydrogenase, 3) Succinyl-CoA transferase, Succinyl-CoA hydrolase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA reductase (aldehyde forming), 9) 1,4-butanediol dehydrogenase, 10) Succinate reductase, 11) Succinyl-CoA reductase (alcohol forming), 12) 4-Hydroxybutyryl-CoA transferase, 4-Hydroxybutyryl-CoA hydrolase, or 4-Hydroxybutyryl-CoA synthetase, 13) 4-Hydroxybutyrate reductase, 14) 4-Hydroxybutyryl-phosphate reductase, and 15) 4-Hydroxybutyryl-CoA reductase (alcohol forming).

Figure 7B:
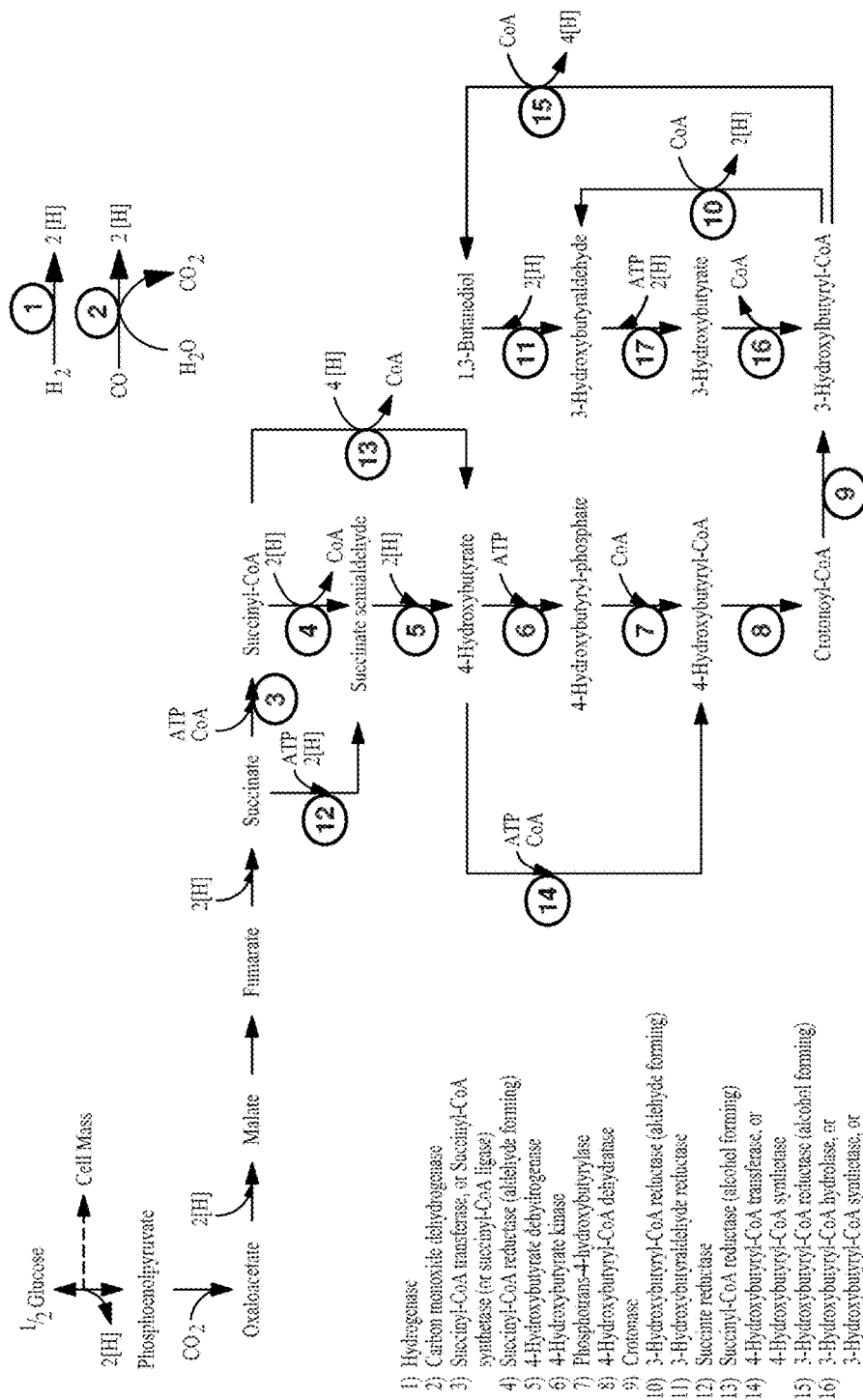

FIG. 7b shows flux distribution for improvement in 1,3-BDO yields from carbohydrates when reducing equivalents from syngas components are available; the enzymatic transformations shown are carried out by the following enzymes: 1) Hydrogenase, 2) Carbon monoxide dehydrogenase, 3) Succinyl-CoA transferase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA dehydratase, 9) crotonase, 10) 3-Hydroxybutyryl-CoA reductase (aldehyde forming), 11) 3-Hydroxybutyraldehyde reductase, 12) Succinate reductase, 13) Succinyl-CoA reductase (alcohol forming), 14) 4-Hydroxybutyryl-CoA transferase, or 4-Hydroxybutyryl-CoA synthetase, 15) 3-Hydroxybutyryl-CoA reductase (alcohol forming), 16) 3-Hydroxybutyryl-CoA hydrolase, or 3-Hydroxybutyryl-CoA synthetase, or 3-Hydroxybutyryl-CoA transferase, and 17) 3-Hydroxybutyrate reductase.

Figure 7C:
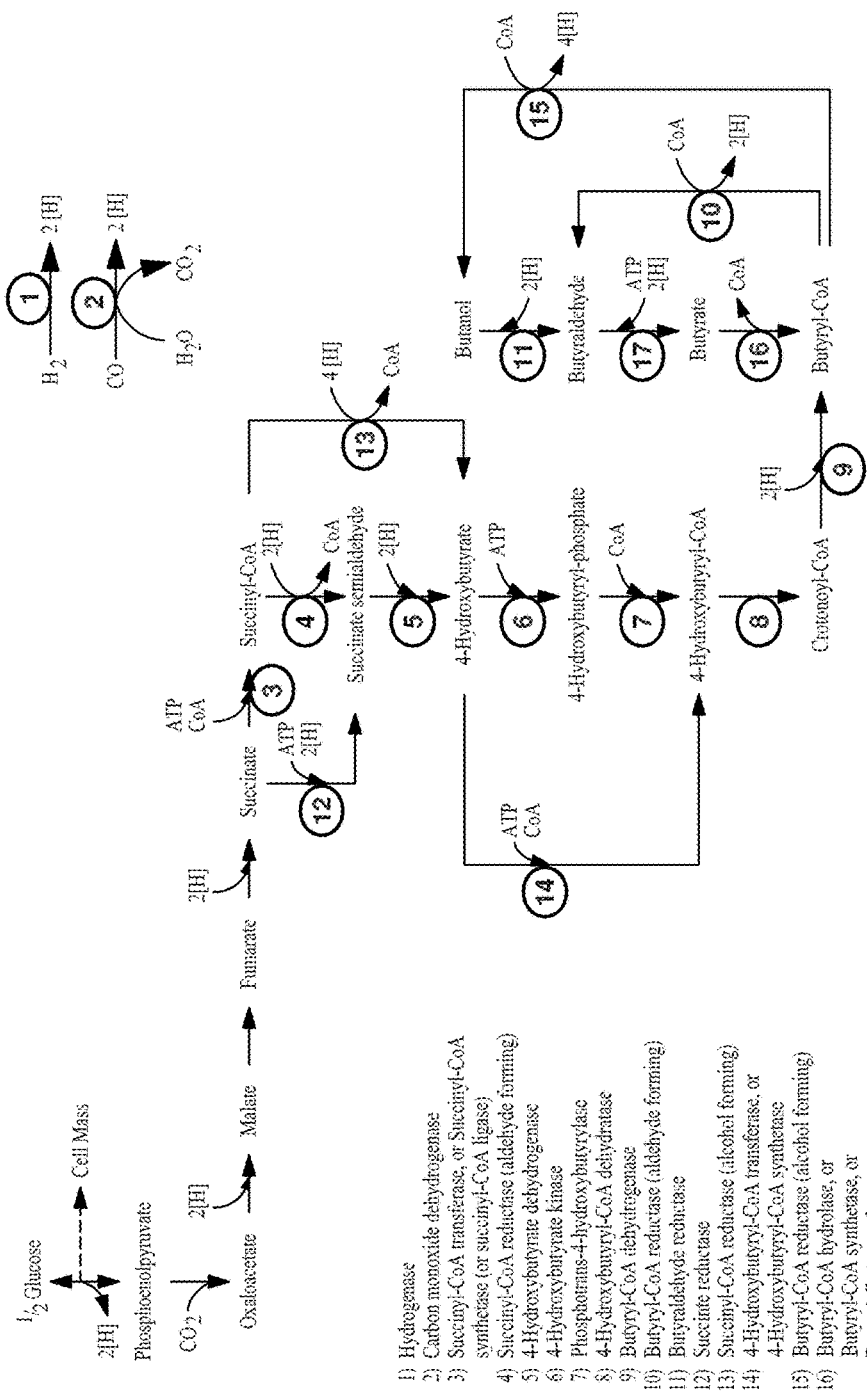

FIG. 7c shows flux distribution for improvement in butanol yields on carbohydrates when reducing equivalents from syngas components are available; the enzymatic transformations shown are carried out by the following enzymes: 1) Hydrogenase, 2) Carbon monoxide dehydrogenase, 3) Succinyl-CoA transferase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA dehydratase, 9) butyryl-CoA dehydrogenase, 10) Butyryl-CoA reductase (aldehyde forming), 11) Butyraldehyde reductase, 12) Succinate reductase, 13) Succinyl-CoA reductase (alcohol forming), 14) 4-Hydroxybutyryl-CoA transferase, or 4-Hydroxybutyryl-CoA synthetase, 15) Butyryl-CoA reductase (alcohol forming), 16) Butyryl-CoA hydrolase, or Butyryl-CoA synthetase, or Butyryl-CoA transferase, and 17) Butyrate reductase.

Figure 7D:
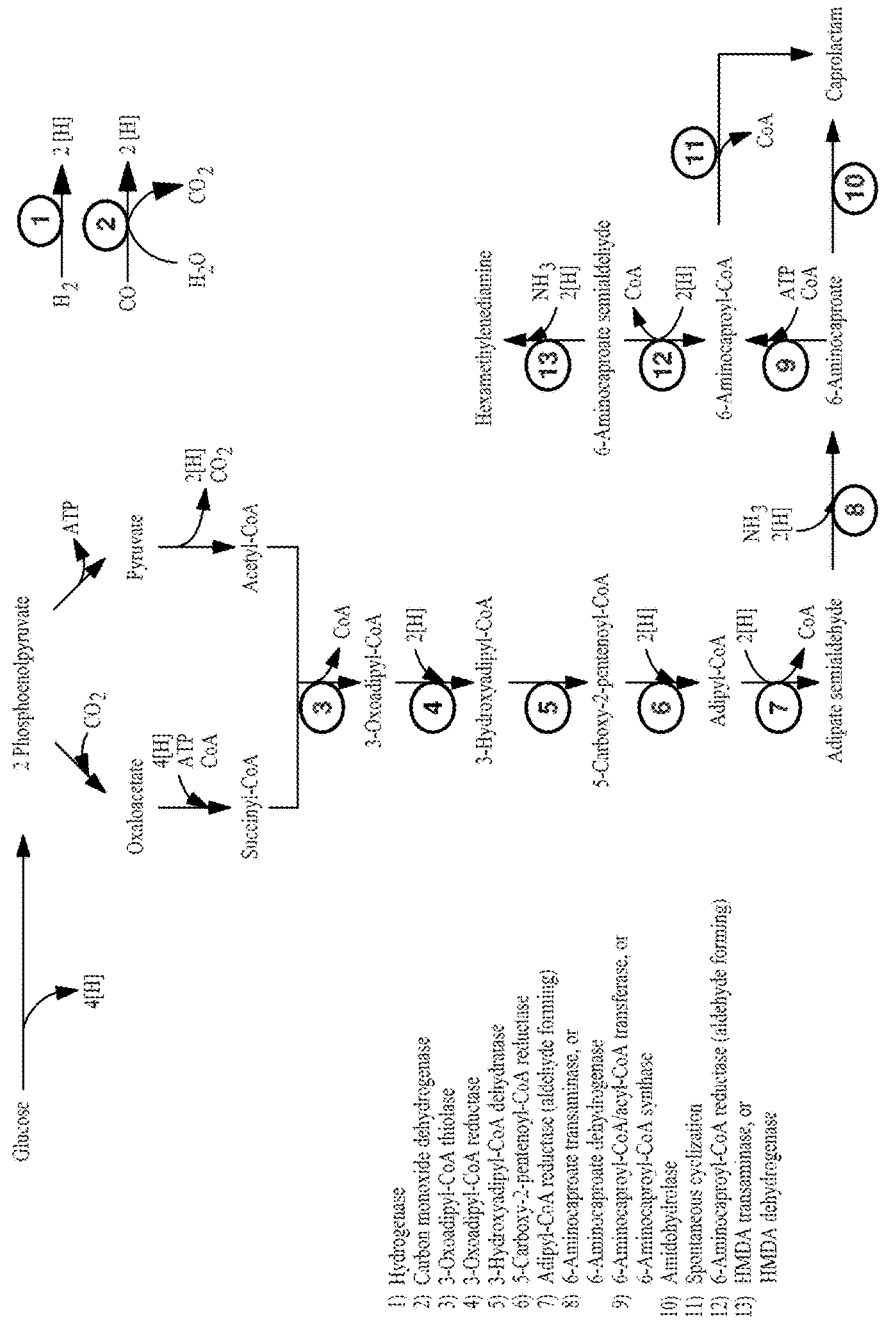

FIG. 7d shows flux distribution for improvement in yields of 6-aminocaproic acid and hexamethylene diamine on carbohydrates when reducing equivalents from syngas components are available; the enzymatic transformations shown are carried out by the following enzymes: 1) Hydrogenase, 2) Carbon monoxide dehydrogenase, 3) 3-Oxoadipyl-CoA thiolase, 4) 3-Oxoadipyl-CoA reductase, 5) 3-Hydroxyadipyl-CoA dehydratase, 6) 5-Carboxy-2-pentenoyl-CoA reductase, 7) Adipyl-CoA reductase (aldehyde forming), 8) 6-Aminocaproate transaminase, or 6-Aminocaproate dehydrogenase, 9) 6-Aminocaproyl-CoA/acyl-CoA transferase, or 6-Aminocaproyl-CoA synthase, 10) Amidohydrolase, 11) Spontaneous cyclization, 12) 6-Aminocaproyl-CoA reductase (aldehyde forming), and 13) HMDA transaminase, or HMDA dehydrogenase.

Figure 7E:
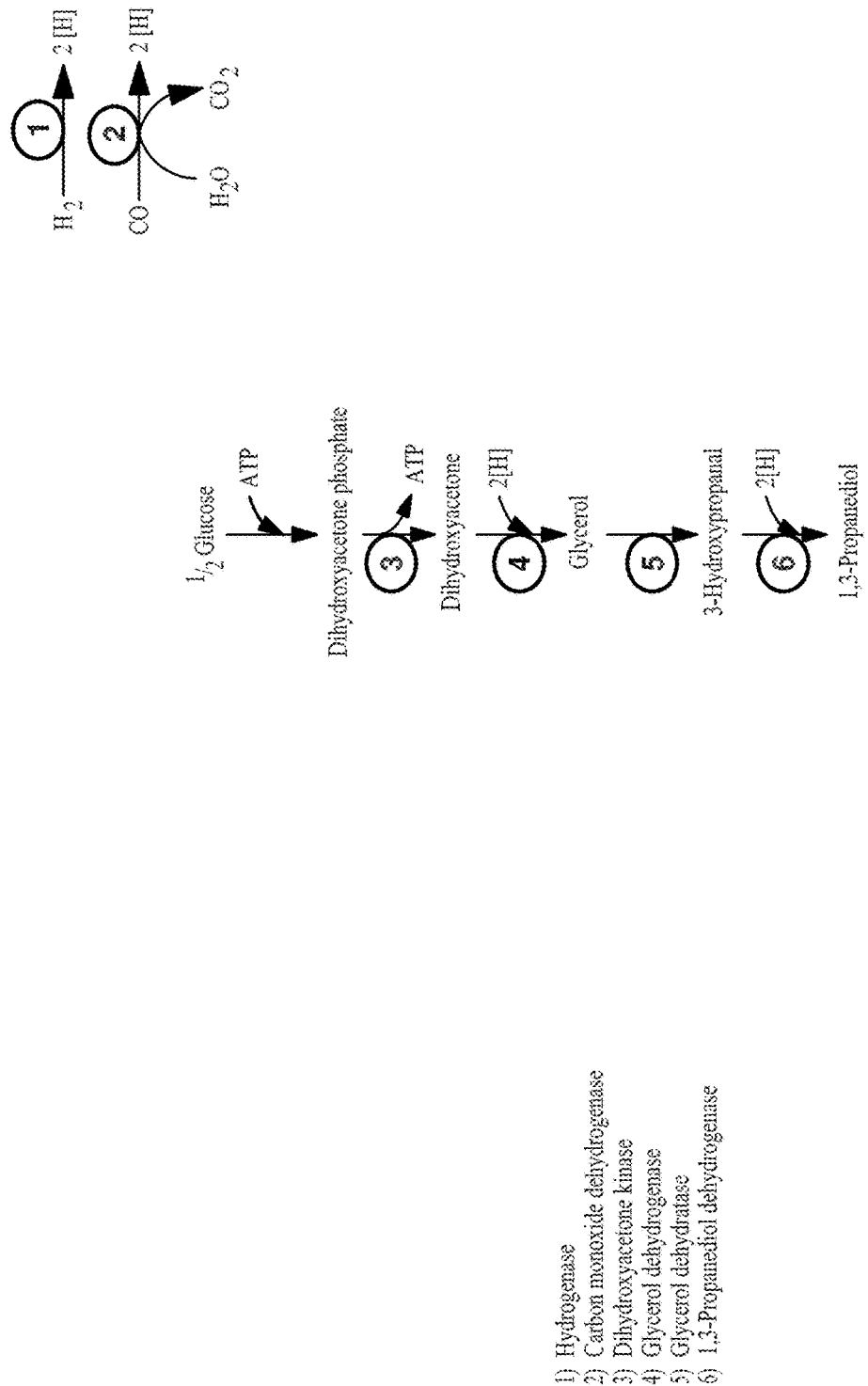

FIG. 7e shows flux distribution for improvement in yields of glycerol and 1,3-propanediol on carbohydrates when reducing equivalents from syngas components are available; the enzymatic transformations shown are carried out by the following enzymes: 1) Hydrogenase, 2) Carbon monoxide dehydrogenase, 3) Dihydroxyacetone kinase, 4) Glycerol dehydrogenase, 5) Glycerol dehydratase, 6) 1,3-Propanediol dehydrogenase.

Figure 8:
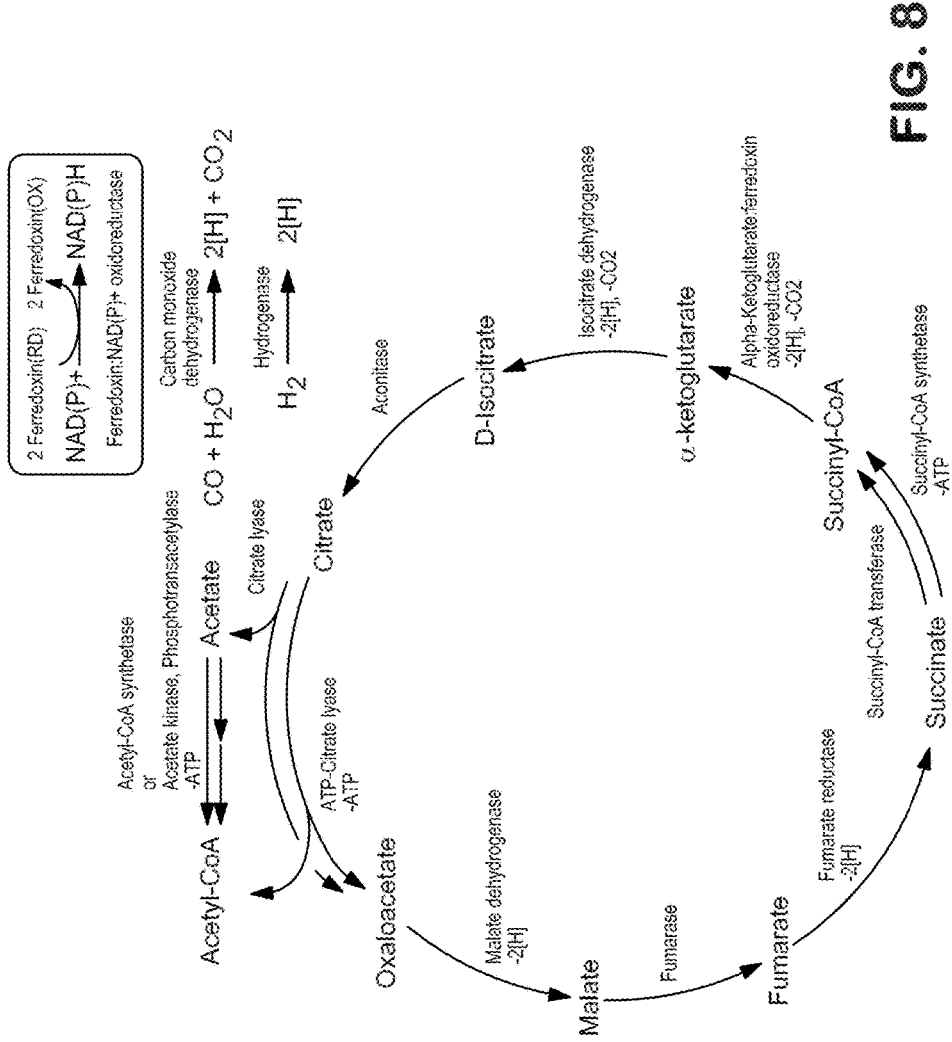

FIG. 8 shows the pathway for the reverse TCA cycle coupled with carbon monoxide dehydrogenase and hydrogenase for the conversion of syngas to acetyl-CoA.

Figure 9:
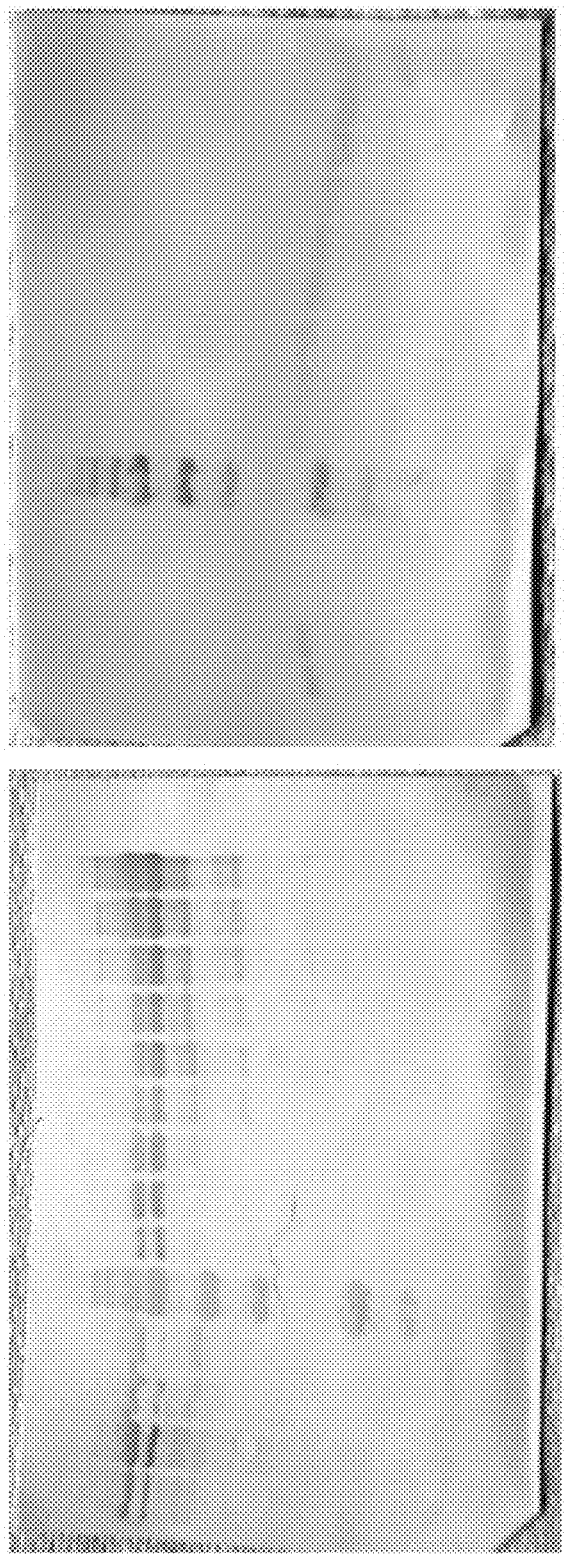

FIG. 9 shows Western blots of 10 micrograms ACS90 (lane 1), ACS91 (lane2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

Figure 10:
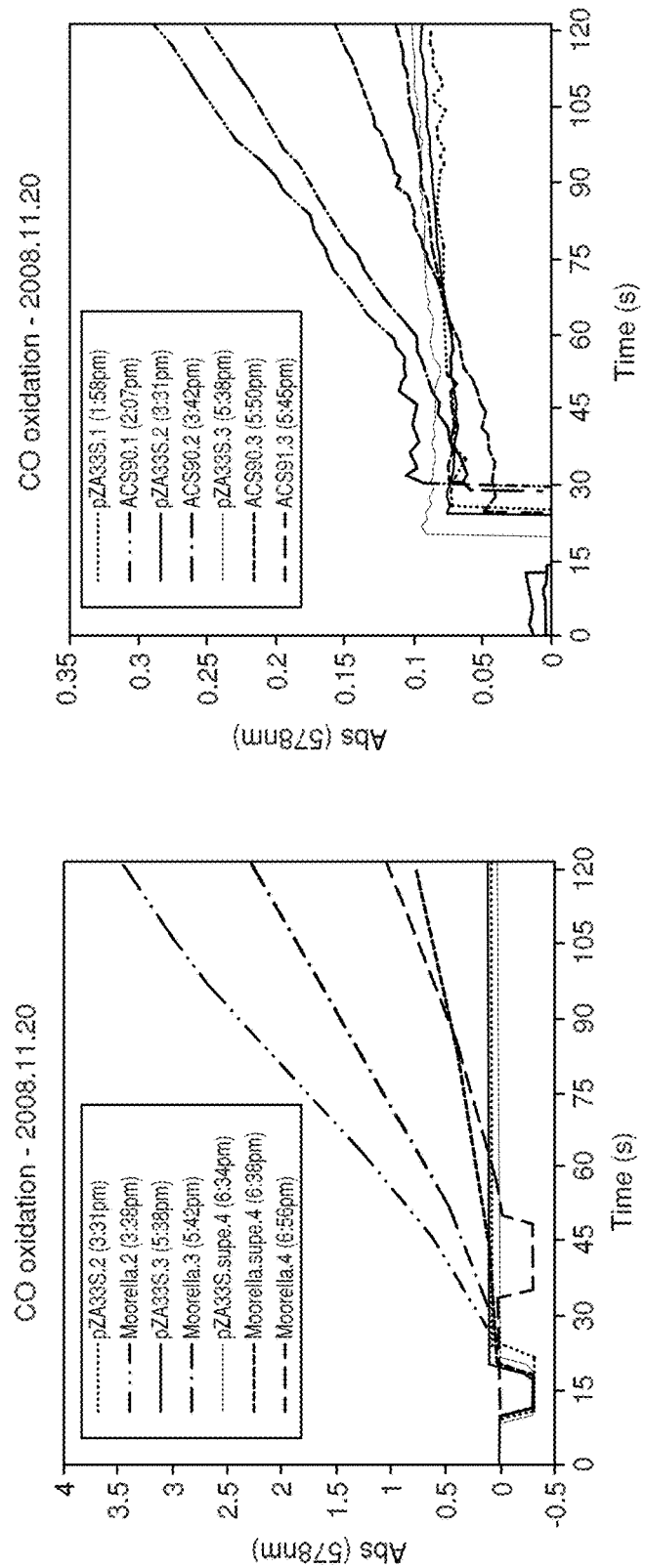

FIG. 10 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

DETAILED DESCRIPTION OF THE INVENTION

This invention is directed, in part to engineered biosynthetic pathways to improve carbon flux through the central metabolism intermediate, acetyl-CoA, en route to product molecules. Exemplary product molecules include, without limitation, 1,3-butanediol, isopropanol, 4-hydroxybutyrate, and 1,4-butanediol, although given the teachings and guidance provided herein, it will be recognized by one skilled in the art that any product molecule that has acetyl-CoA as a building block can exhibit enhanced production through increased carbon flux through acetyl-CoA. The present invention provides non-naturally occurring microbial organisms having one or more exogenous genes encoding enzymes that can catalyze various enzymatic transformations en route to acetyl-CoA. In some embodiments, these enzymatic transformations are part of the reductive tricarboxylic acid (RTCA) cycle and are used to improve product yields from carbohydrate-based carbon feedstock.

This invention is also directed, in part, to improving product yields based on enzymatic transformations of the Wood-Ljungdahl pathway. In some embodiments, syngas components, such as CO and $H_2$, can serve as source of reducing equivalents. Such reducing equivalents can improve product yields from carbohydrate-based carbon feedstock as described herein below.

In numerous engineered pathways, realization of maximum product yields based on carbohydrate feedstock is hampered by insufficient reducing equivalents or by loss of reducing equivalents and/or carbon to byproducts. In accordance with some embodiments, the present invention increases the yields of products by (i) enhancing carbon fixation via the Wood-Ljungdahl pathway and/or the reductive TCA cycle, and (ii) accessing additional reducing equivalents from gaseous syngas components such as CO, $CO_2$, and/or $H_2$. Products that can be produced by non-naturally occurring organisms and methods described herein include, without limitation, ethanol, butanol, isobutanol, 1,3-butanediol, isopropanol, 4-hydroxybutyrate, 1,4-butanediol, succinic acid, fumaric acid, malic acid, 3-hydroxypropionic acid, lactic acid, adipic acid, 6-aminocaproic acid, hexamethylenediamine, caprolactam, 3-hydoxyisobutyric acid, 2-hydroxyisobutyric acid, methacrylic acid, acrylic acid, 1,3-propanediol, glycerol, and long chain hydrocarbons, alcohols, acids, and esters.

Figure 2A:
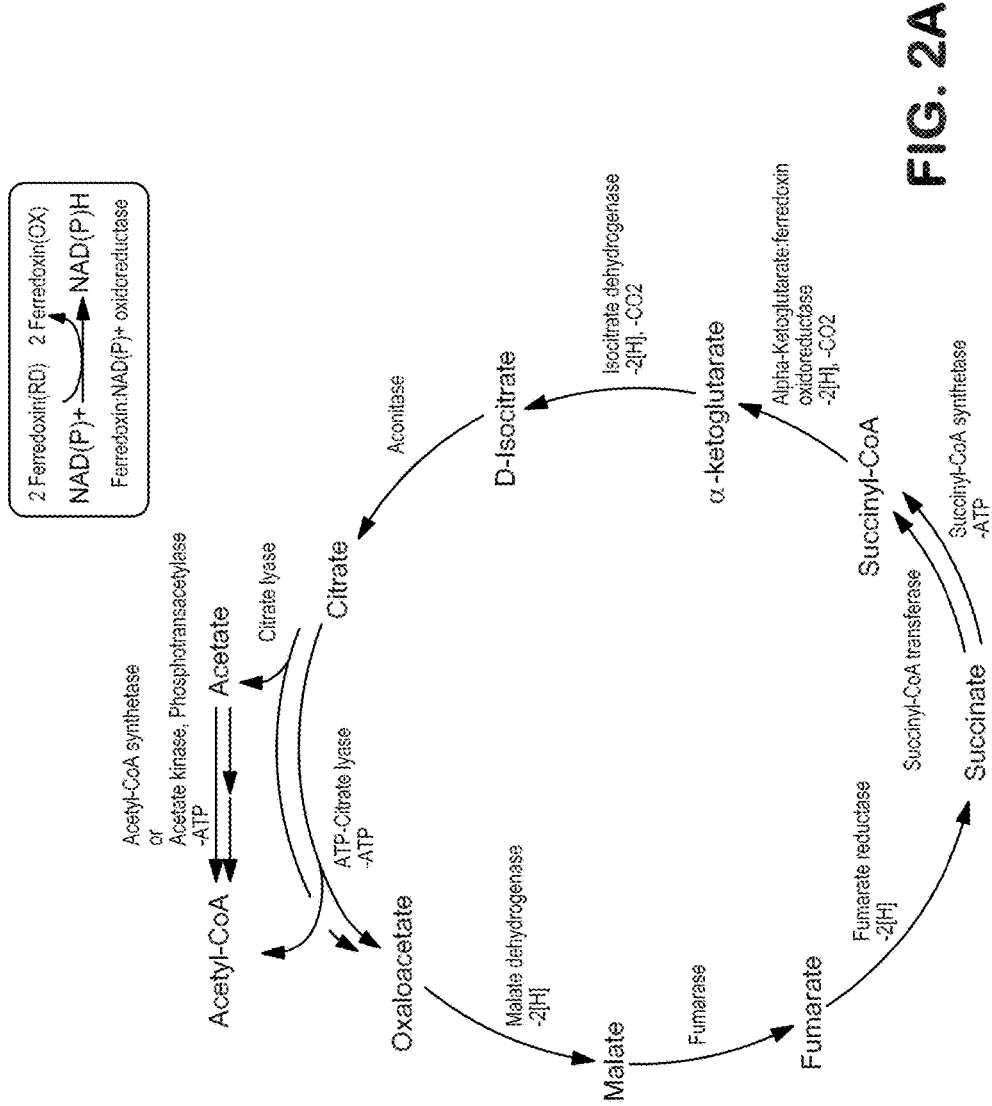
FIG. 2a shows the reverse TCA cycle for fixation of $CO_2$ on carbohydrates as substrates. The enzymatic transformations are carried out by the enzymes as shown.
Figure 2B:
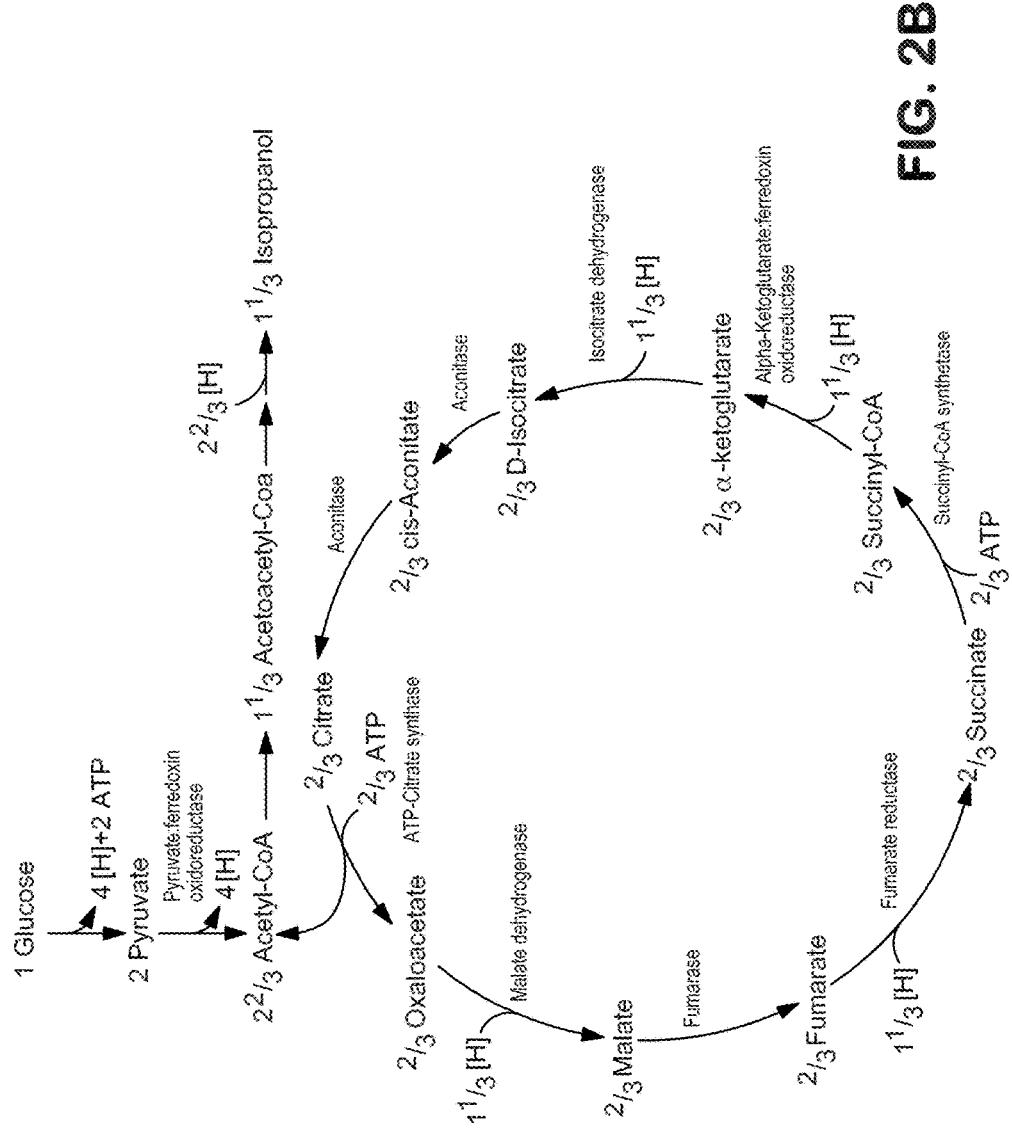
FIG. 2b shows the flux distribution showing an enhanced maximum theoretical yield of isopropanol on glucose when carbon is routed via the reductive TCA cycle

The $CO_2$-fixing reductive tricarboxylic acid (RTCA) cycle is an endergenic anabolic pathway of $CO_2$ assimilation which uses NAD(P)H and ATP (FIG. 2a). One turn of the RTCA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol. Note that the pathways for the exemplary product molecules described herein all proceed through acetyl-CoA. For example, the fixation of $CO_2$ provides 2.67 molecules of acetyl-CoA from every molecule of glucose, thus improving the maximum product yields as follows:

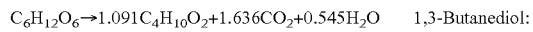 1,3-Butanediol:

 Isopropanol:

 4-Hydroxybutyate:

 1,4-Butanediol:

FIG. 2b provides an exemplary flux distribution showing how the maximum theoretical isopropanol yield increases from 1 mole/mole glucose to 1.33 moles per mole glucose. The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophillic Knallgas bacteria) and sulfur-dependent archaea (Hugler et al. *J. Bacteriol.* 187:3020-3027 (2005); Hugler et al. *Environ. Microbiol.* 9:81-92 (2007)). In some cases, reductive and oxidative (Krebs) TCA cycles are present in the same organism (Hugler et al. supra (2007); Siebers et al. *J. Bacteriol.* 186:2179-2194 (2004). Some methanogens and obligate anaerobes possess incomplete oxidative or reductive TCA cycles that can function to synthesize biosynthetic intermediates (Ekiel et al. *J. Bacteriol.* 162:905-908 (1985); Wood et al. *FEMS Microbiol.* 28: 335-352 (2004).

Many of the enzymes in the TCA cycle are reversible and can catalyze reactions in the reductive and oxidative directions. Several reactions are irreversible and utilize different enzymes to catalyze the forward and reverse directions. These reactions include: 1) conversion of citrate to oxaloacetate and acetyl-CoA, 2) conversion of fumarate to succinate, 3) conversion of succinyl-CoA to 2-oxoglutarate. In the catabolic TCA cycle, citrate is formed from the condensation of oxaloacetate and acetyl-CoA. The reverse reaction, cleavage of citrate to oxaloacetate and acetyl-CoA, is ATP-dependent and catalyzed by ATP citrate lyase or citryl-CoA synthetase and citryl-CoA lyase. The conversion of succinate to fumarate is catalyzed by succinate dehydrogenase while the reverse reaction is catalyzed by fumarate reductase. In the catabolic TCA cycle, succinyl-CoA is formed from the NAD(P)$^+$ dependent decarboxylation of 2-oxoglutarate by the AKGDH complex. The reverse reaction is catalyzed by alpha-ketoglutarate:ferredoxin oxidoreductase. In some embodiments, the invention provides non-naturally occurring organisms that enhance carbon flux through acetyl-CoA by engineering one or more enzymes that are part of the reverse TCA cycle.

In some embodiments, the invention provides enhanced product yields via carbohydrate-based carbon feedstock by fixing carbon dioxide and/or methanol via the Wood-Ljungdahl pathway or components thereof. Synthesis gas (syngas) is a mixture of $H_2$ and CO that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and this source represents an inexpensive and flexible feedstock for the biological production of renewable chemicals and fuels.

There are known pathways in organisms such as *Clostridia* that utilize syngas effectively. Specifically, acetogens, such as *Moorella thermoacetica*, *C. ljungdahlii* and *C. carboxidivorans*, can grow on a number of carbon sources ranging from hexose sugars to carbon monoxide. Hexoses, such as glucose, are metabolized first via Embden-Meyerhof-Parnas (EMP) glycolysis to pyruvate, which is then converted to acetyl-CoA via pyruvate:ferredoxin oxidoreductase (PFOR). Acetyl-CoA can be used to build biomass precursors or can be converted to acetate which produces energy via acetate kinase and phosphotransacetylase. The overall conversion of glucose to acetate, energy, and reducing equivalents is

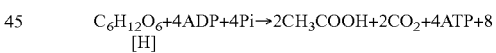

Acetogens extract even more energy out of the glucose to acetate conversion while also maintaining redox balance by further converting the released $CO_2$ to acetate via the Wood-Ljungdahl pathway:

The coefficient "n" in the above equation signifies that this conversion is an energy generating endeavor, as many acetogens can grow in the presence of $CO_2$ via the Wood-Ljungdahl pathway even in the absence of glucose as long as hydrogen is present to supply reducing equivalents.

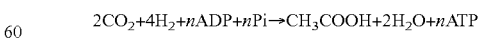

Figure 3A:
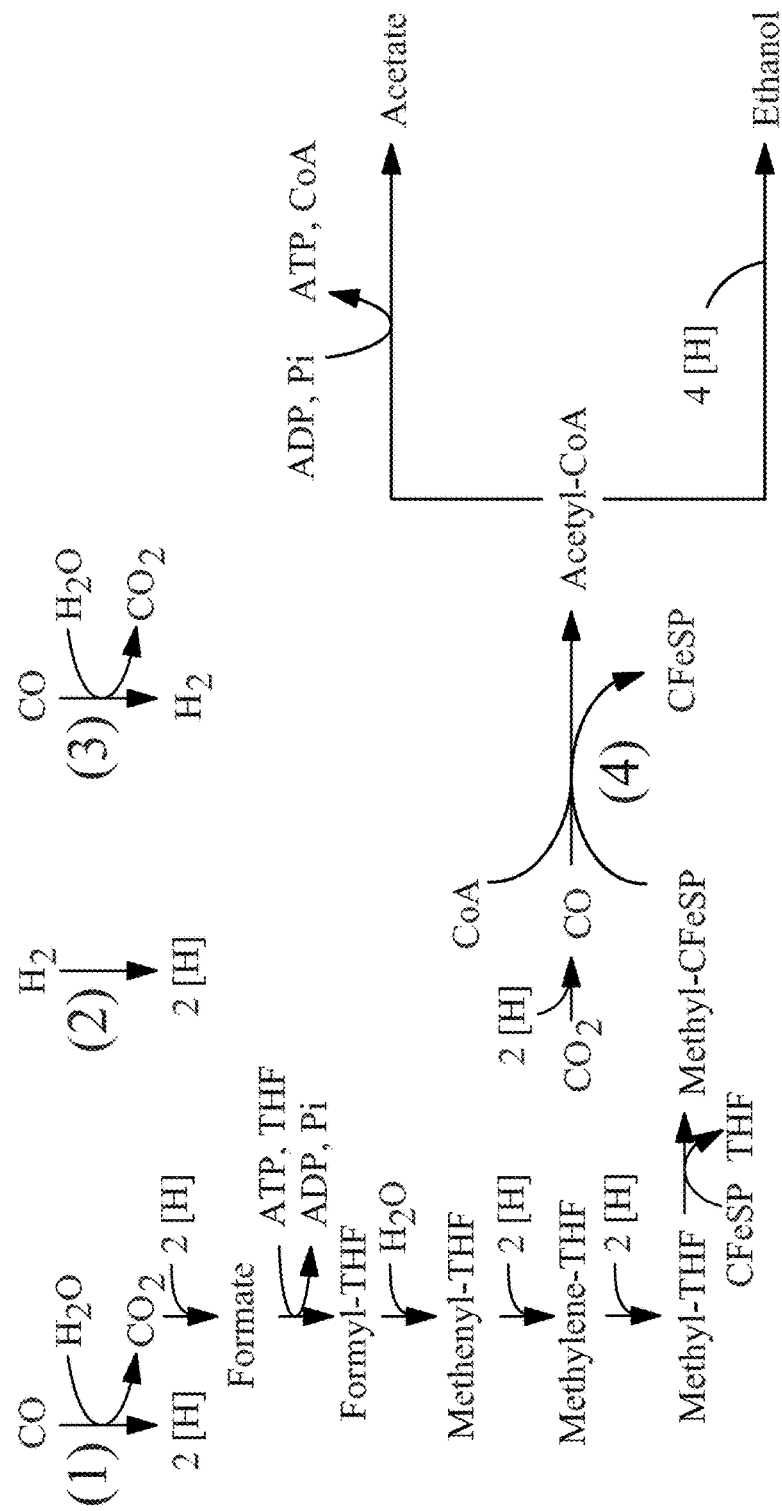
FIG. 3a shows a flow diagram depicting the Wood-Ljungdahl pathway and formation routes for acetate and ethanol; the transformations that are carried out in organisms capable of growth on synthesis gas are 1) CO dehydrogenase, 2) hydrogenase, 3) energy-conserving hydrogenase (ECH), and 4) bi-functional CO dehydrogenase/acetyl-CoA synthase.

The Wood-Ljungdahl pathway, illustrated in FIG. 3A, is coupled to the creation of Na$^+$ or H$^+$ ion gradients that can generate ATP via an Na$^+$- or H$^+$-dependant ATP synthase, respectively (Muller, V., *Appl. Environ. Microbiol.* 69:6345-6353 (2003)). Based on these known transformations, acetogens also have the capacity to utilize CO as the sole carbon and energy source. Specifically, CO can be oxidized to produce reducing equivalents and $CO_2$, or directly assimilated into acetyl-CoA which is subsequently converted to either biomass or acetate.

$$4CO + 2H_2O \rightarrow CH_3COOH + 2CO_2$$

Even higher acetate yields, however, can be attained when enough hydrogen is present to satisfy the requirement for reducing equivalents.

$$2CO + 2H_2 \rightarrow CH_3COOH$$

Following from FIG. 3A, the production of acetate via acetyl-CoA generates one ATP molecule.

Figure 3B:
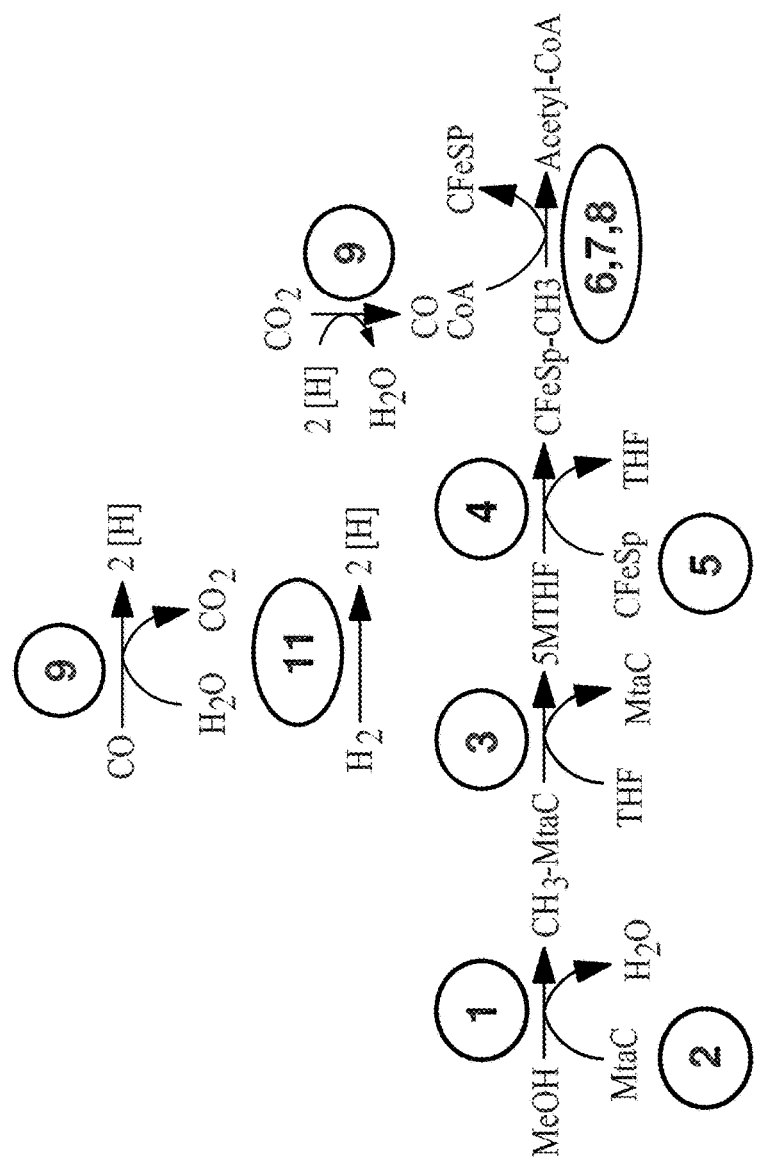
FIG. 3b shows a pathway for the utilization of methanol for the formation of acetyl-CoA; the enzymatic transformations shown are carried out by the following enzymes: 1) Methanol methyltransferase (MtaB), 2) Corrinoid protein (MtaC), 3) Methyltetrahydrofolate:corrinoid protein methyltransferase (MtaA), 4) Methyltetrahydrofolate:corrinoid protein methyltransferase (AcsE), 5) Corrinoid iron-sulfur protein (AcsD), 6) Nickel-protein assembly protein (AcsF & CooC), 7) Ferredoxin (Orf7), 8) Acetyl-CoA synthase (AcsB & AcsC), and 9) Carbon monoxide dehydrogenase (AcsA).

Methanol is a relatively inexpensive organic feedstock that can be derived from synthesis gas components, CO and $H_2$, via catalysis. A non-naturally occurring microbial organism of the invention capable of utilizing methanol can also utilize gases including, for example, CO, $CO_2$, and/or $H_2$ for conversion to acetyl-CoA, cell mass, and products. Specifically, acetogens such as *Moorella thermoacetica* (formerly, *Clostridium thermoaceticum*) use syngas via the Wood-Ljungdahl pathway. This pathway includes two branches: the Eastern (or methyl) branch converts $CO_2$ to methyltetrahydrofolate (Me-THF) and the Western (or carbonyl) branch that converts methyl-THF, CO, and Coenzyme-A into acetyl-CoA (FIG. 3B). Any non-naturally occurring microorganism of the invention expressing genes encoding enzymes that catalyze the carbonyl-branch of the Wood-Ljungdahl pathway in conjunction with a MtaABC-type methyltransferase system is capable of 'fixing' carbon from exogenous CO and/or $CO_2$ and methanol to synthesize acetyl-CoA, cell mass, and products.

Implementing the pathway to form acetyl-CoA from methanol and syngas, heretofor referred to as the "methanol Wood-Ljungdahl pathway," is energetically favorable compared to utilizing the full Wood-Ljungdahl pathway. For example, the direct conversion of synthesis gas to acetate is an energetically neutral process (see FIG. 3B). Specifically, one ATP molecule is consumed during the formation of formyl-THF by formyl-THF synthase and one ATP molecule is produced during the production of acetate via acetate kinase. ATP consumption can be circumvented by ensuring that the methyl group on the methyl branch product, methyl-THF, is obtained from methanol rather than $CO_2$. The result is that acetate formation has a positive ATP yield that can help support cell growth and maintenance. A non-naturally occurring microbial organism of the present invention, engineered with these capabilities, that also naturally possesses the capability for anapleurosis (e.g., *E. coli*) can grow on the methanol and syngas-generated acetyl-CoA in the presence of a suitable external electron acceptor such as nitrate. This electron acceptor is used to accept electrons from the reduced quinone formed via succinate dehydrogenase. A further use of adding an external electron acceptor is that additional energy for cell growth, maintenance, and product formation can be generated from respiration of acetyl-CoA. In some embodiments, engineering a pyruvate ferredoxin oxidoreductase (PFOR) enzyme into a non-naturally occurring microbial organism allows the synthesis of biomass precursors in the absence of an external electron acceptor.

Carbon from syngas and/or methanol can be fixed via the Wood-Ljungdahl pathway and portions thereof when using carbohydrate-based carbon feedstock for the formation of molecules such as 1,3-butanediol, isopropanol, 4-hydroxybutyrate, and 1,4-butanediol using the pathways described herein. Specifically, the combination of certain syngas-utilization pathway components with the acetyl-CoA to 1,3-butanediol, isopropanol, 4-hydroxybutyrate, or 1,4-butanediol pathways results in high yields of these products from carbohydrates by providing an efficient mechanism for fixing the carbon present in carbon dioxide, fed exogenously or produced endogenously, into acetyl-CoA as shown below. Exemplary carbohydrates include but are not limited to glucose, sucrose, xylose, arabinose and glycerol. The enzymatic transformations for carbon fixation are shown in FIGS. 4A and 4B respectively.

Figure 5A:
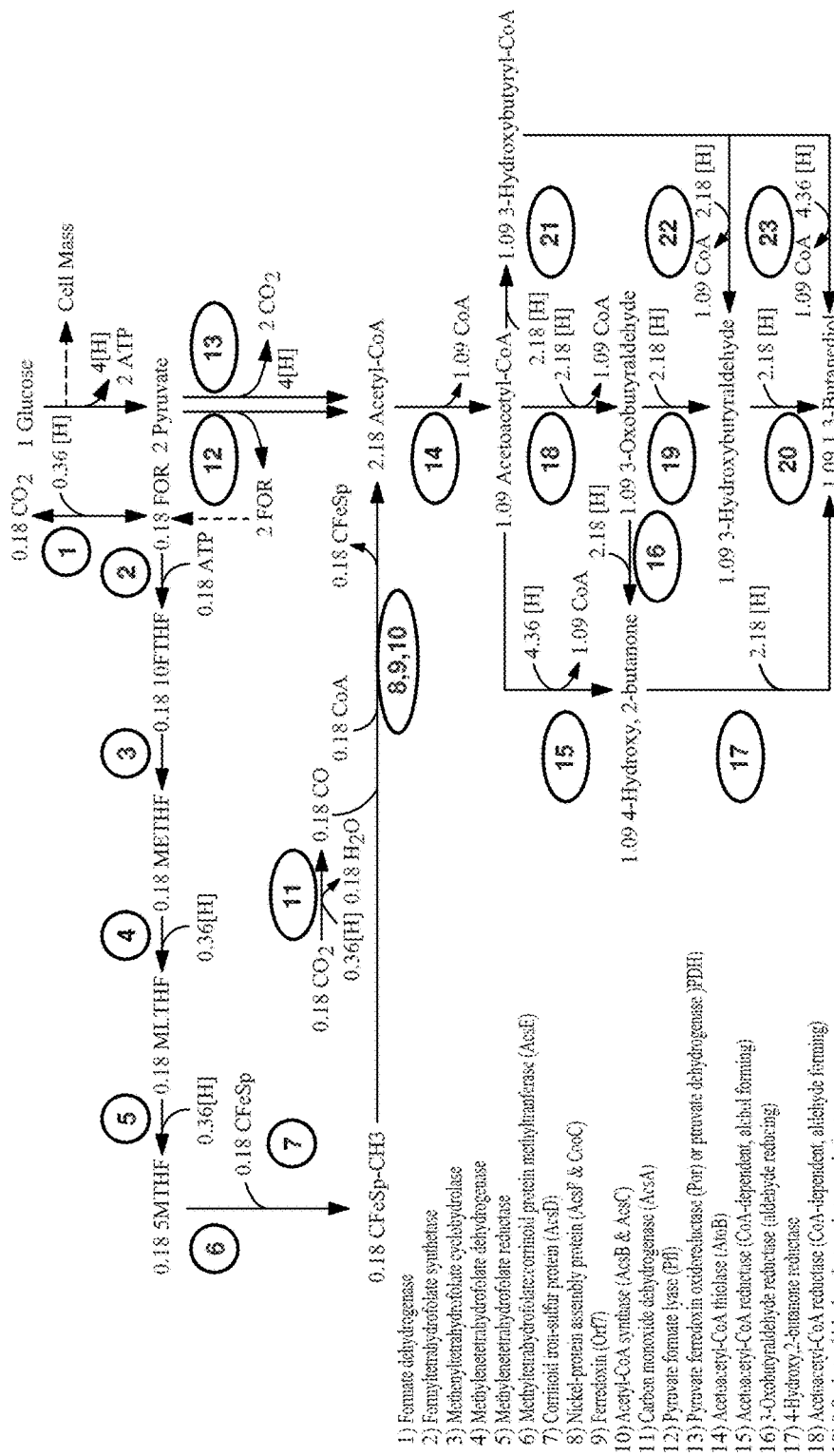
FIG. 5a shows the flux distribution with an enhanced maximum theoretical yield of 1,3-butanediol on glucose when carbon fixation via the Wood-Ljungdahl pathway is employed in the absence of methanol; the enzymatic transformations shown are carried out by the following enzymes: 1) Formate dehydrogenase, 2) Formyltetrahydrofolate synthetase, 3) Methenyltetra-hydrofolate cyclohydrolase, 4) Methylenetetrahydrofolate dehydrogenase, 5) Methylenetetra-hydrofolate reductase, 6) Methyltetrahydrofolate:corrinoid protein methyltransferase (AcsE), 7) Corrinoid iron-sulfur protein (AcsD), 8) Nickel-protein assembly protein (AcsF & CooC), 9) Ferredoxin (Orf7), 10) Acetyl-CoA synthase (AcsB & AcsC), 11) Carbon monoxide dehydrogenase (AcsA), 12) Pyruvate formate lyase (Pfl), 13) Pyruvate ferredoxin oxidoreductase (Por) or pyruvate dehydrogenase (PDH), 14) Acetoacetyl-CoA thiolase (AtoB), 15) Acetoacetyl-CoA reductase (CoA-dependent, alcohol forming), 16) 3-Oxobutyraldehyde reductase (aldehyde reducing), 17) 4-Hydroxy-2-butanone reductase, 18) Acetoacetyl-CoA reductase (CoA-dependent, aldehyde forming), 19) 3-Oxobutyraldehyde reductase (ketone reducing), 20) 3-Hydroxybutyraldehyde reductase, 21) Acetoacetyl-CoA reductase (ketone reducing), 22) 3-Hydroxybutyryl-CoA reductase (aldehyde forming), 23) 3-Hydroxybutyryl-CoA reductase (alcohol forming); when glucose is fed in the presence of the Wood-Ljungdahl pathway, a yield increase from 1 mol 1,3-butanediol/mol glucose to 1.09 mol 1,3-butanediol/mol glucose is realized.
Figure 5B:
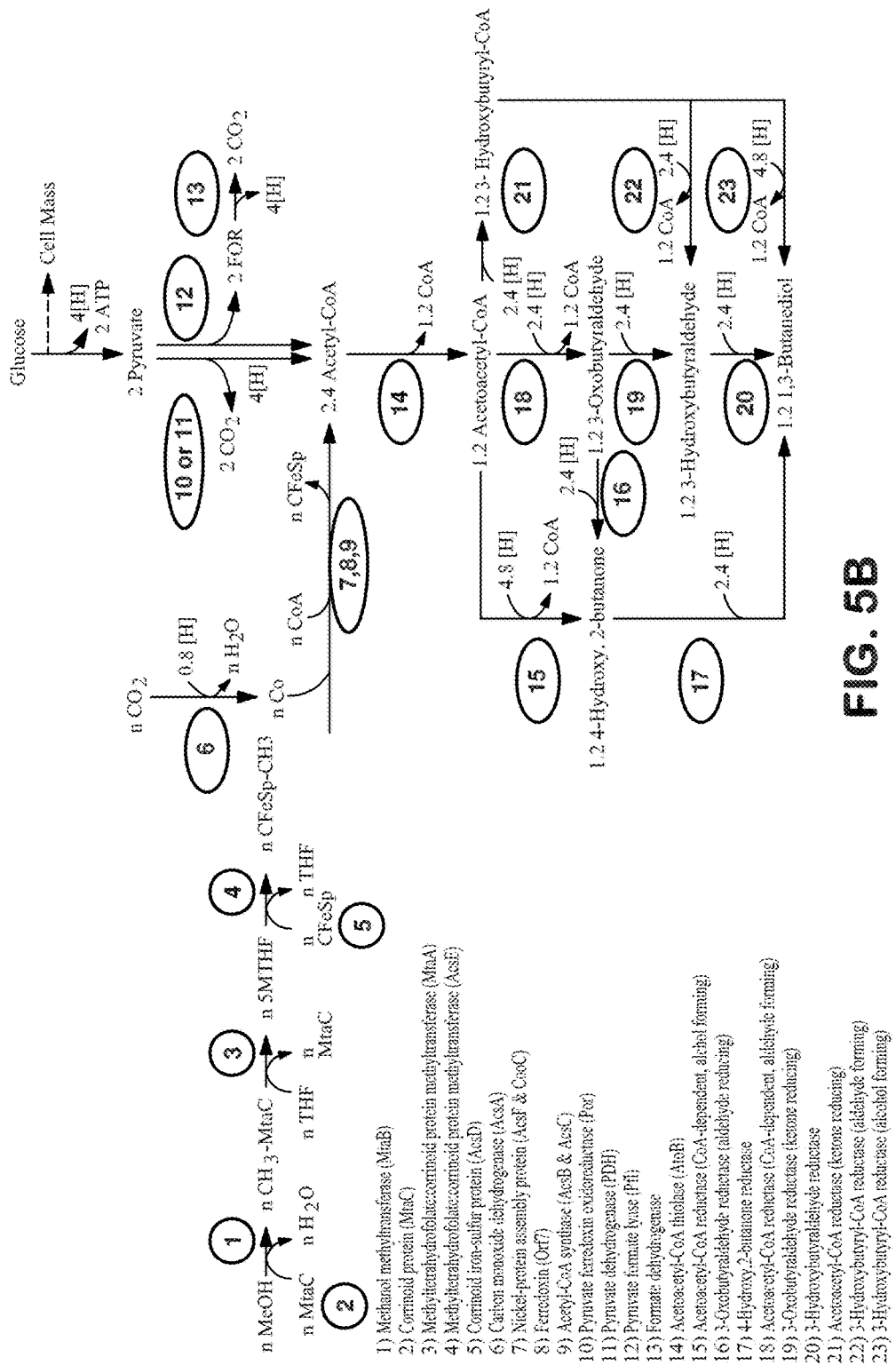
FIG. 5b shows the flux distribution with an enhanced maximum theoretical yield of 1,3-butanediol from glucose when carbon fixation via the methanol Wood-Ljungdahl pathway is employed using both syngas and methanol; the enzymatic transformations shown are carried out by the following enzymes: 1) Methanol methyltransferase (MtaB), 2) Corrinoid protein (MtaC), 3) Methyltetrahydrofolate:corrinoid protein methyltransferase (MtaA), 4) Methyltetrahydro-folate:corrinoid protein methyltransferase (AcsE), 5) Corrinoid iron-sulfur protein (AcsD), 6) Carbon monoxide dehydrogenase (AcsA), 7) Nickel-protein assembly protein (AcsF & CooC), 8) Ferredoxin (Orf7), 9) Acetyl-CoA synthase (AcsB & AcsC), 10) Pyruvate ferredoxin oxidoreductase (Por), 11) Pyruvate dehydrogenase (PDH), 12) Pyruvate formate lyase (Pfl), 13) Formate dehydrogenase, 14) Acetoacetyl-CoA thiolase (AtoB), 15) Acetoacetyl-CoA reductase (CoA-dependent, alcohol forming), 16) 3-Oxobutyraldehyde reductase (aldehyde reducing), 17) 4-Hydroxy-2-butanone reductase, 18) Acetoacetyl-CoA reductase (CoA-dependent, aldehyde forming), 19) 3-Oxobutyraldehyde reductase (ketone reducing), 20) 3-Hydroxybutyraldehyde reductase, 21) Acetoacetyl-CoA reductase (ketone reducing), 22) 3-Hydroxybutyryl-CoA reductase (aldehyde forming), 23) 3-Hydroxybutyryl-CoA reductase (alcohol forming); when glucose and methanol are fed in 1.0:0.4 ratio, it affords an increase from 1 mol 1,3-butanediol/mol glucose to 1.2 mol 1,3-butanediol/mol glucose.
Figure 6A:
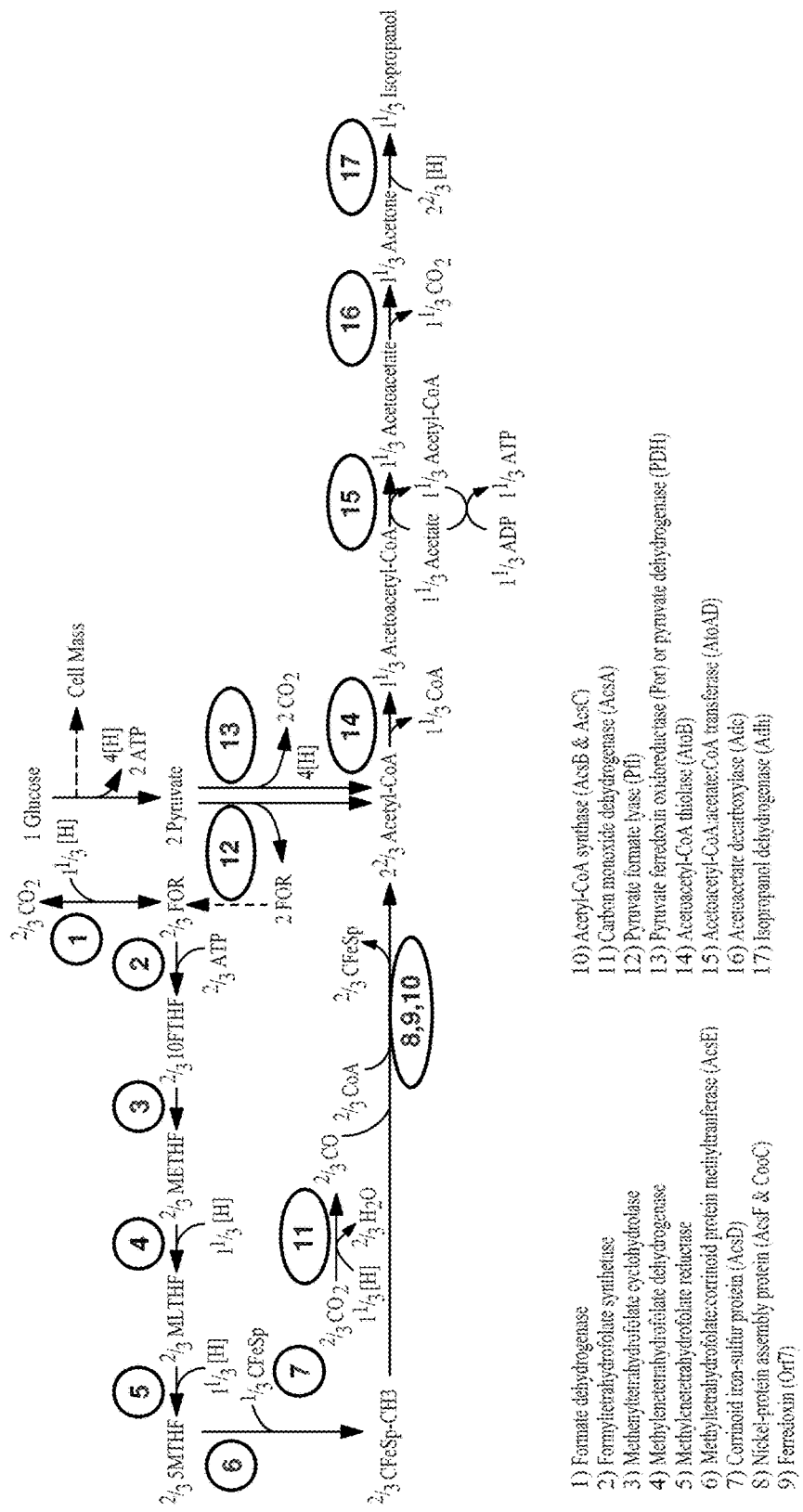
FIG. 6a shows the flux distribution with an enhanced maximum theoretical yield of isopropanol from glucose when carbon fixation via the Wood-Ljungdahl pathway is employed in the absence of methanol; the enzymatic transformations shown are carried out by the following enzymes: 1) Formate dehydrogenase, 2) Formyltetrahydrofolate synthetase, 3) Methenyltetra-hydrofolate cyclohydrolase, 4) Methylenetetrahydrofolate dehydrogenase, 5) Methylenetetrahydrofolate reductase, 6) Methyltetrahydrofolate:corrinoid protein methyltransferase (AcsE), 7) Corrinoid iron-sulfur protein (AcsD), 8) Nickel-protein assembly protein (AcsF & CooC), 9) Ferredoxin (Orf7), 10) Acetyl-CoA synthase (AcsB & AcsC), 11) Carbon monoxide dehydrogenase (AcsA), 12) Pyruvate formate lyase (Pfl), 13) Pyruvate ferredoxin oxidoreductase (Por) or pyruvate dehydrogenase (PDH), 14) Acetoacetyl-CoA thiolase (AtoB), 15) Acetoacetyl-CoA:acetate:CoA transferase (AtoAD), 16) Acetoacetate decarboxylase (Adc), and 17) Isopropanol dehydrogenase (Adh).
Figure 6B:
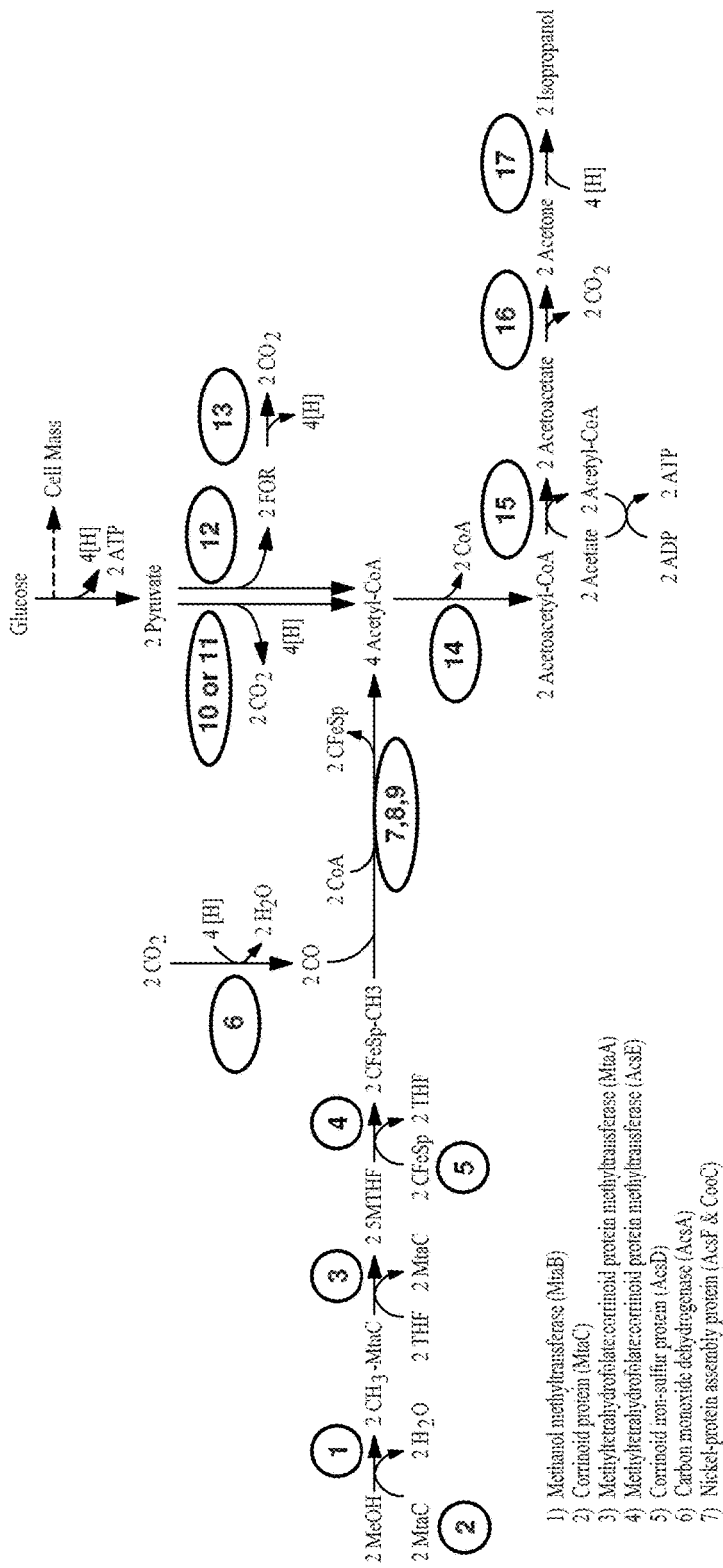
FIG. 6b shows the flux distribution with an enhanced maximum theoretical yield of isopropanol from glucose when carbon fixation via the methanol Wood-Ljungdahl pathway is employed using both syngas and methanol; the enzymatic transformations shown are carried out by the following enzymes: 1) Methanol methyltransferase (MtaB), 2) Corrinoid protein (MtaC), 3) Methyltetrahydrofolate.

$C_6H_{12}O_6 \rightarrow 1.091 C_4H_{10}O_2 + 1.636 CO_2 + 0.545 H_2O$   1,3-Butanediol:

$C_6H_{12}O_6 \rightarrow 1.333 C_3H_8O + 2 CO_2 + 0.667 H_2O$   Isopropanol:

$C_6H_{12}O_6 \rightarrow 1.333 C_4H_8O_3 + 0.667 CO_2 + 0.667 H_2O$   4-Hydroxybutyate:

$C_6H_{12}O_6 \rightarrow 1.091 C_4H_{10}O_2 + 1.636 CO_2 + 0.545 H_2O$   1,4-Butanediol:

The maximum theoretical yields of isopropanol, 4-hydroxybutyrate, and 1,4-butanediol from synthesis gases or carbohydrates can be further enhanced by the addition of methanol in different ratios of methanol to glucose. This is shown in the equations below:

$CH_4O + C_6H_{12}O_6 \rightarrow 1.364 C_4H_{10}O_2 + 1.545 CO_2 + 1.182 H_2O$   1,3-Butanediol:

$CH_4O + C_6H_{12}O_6 \rightarrow 1.667 C_3H_8O + 2 CO_2 + 1.333 H_2O$   Isopropanol:

$CH_4O + C_6H_{12}O_6 \rightarrow 1.667 C_4H_8O_3 + 0.333 CO_2 + 1.333 H_2O$   4-Hydroxybutyate:

$CH_4O + C_6H_{12}O_6 \rightarrow 1.364 C_4H_{10}O_2 + 1.545 CO_2 + 1.182 H_2O$   1,4-Butanediol:

$2 CH_4O + C_6H_{12}O_6 \rightarrow 1.636 C_4H_{10}O_2 + 1.455 CO_2 + 1.818 H_2O$   1,3-Butanediol:

$2 CH_4O + C_6H_{12}O_6 \rightarrow 2 C_3H_8O + 2 CO_2 + 2 H_2O$   Isopropanol:

$2 CH_4O + C_6H_{12}O_6 \rightarrow 2 C_4H_8O_3 + 2 H_2O$   4-Hydroxybutyate:

$2 CH_4O + C_6H_{12}O_6 \rightarrow 1.636 C_4H_{10}O_2 + 1.455 CO_2 + 1.818 H_2O$   1,4-Butanediol:

Exemplary flux distributions showing improvements in yields of 1,3-butanediol and isopropanol via carbohydrate-based carbon feedstock when carbon can be fixed via the Wood-Ljungdahl pathway using syngas components with and without methanol are shown in FIGS. 5 and 6, respectively.

Thus, the non-naturally occurring microbial organisms and conversion routes described herein provide an efficient means of converting carbohydrates to products such as isopropanol, 4-hydroxybutyrate, or 1,4-butanediol. Additional product molecules that can be produced by the teachings of this invention include but are not limited to ethanol, butanol, isobutanol, isopropanol, 1,4-butanediol, succinic acid, fumaric acid, malic acid, 4-hydroxybutyric acid, 3-hydroxypropionic acid, lactic acid, adipic acid, 6-aminocaproic acid, hexamethylenediamine, caprolactam, 3-hydoxyisobutyric acid, 2-hydroxyisobutyric acid, methacrylic acid, acrylic acid, glycerol, 1,3-propanediol, and long chain hydrocarbons, alcohols, acids, and esters.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a 1,4-butanediol, 4-hydroxybutyrate, 1,3-butanediol, isopropanol, 6-aminocaproic acid, hexamethylene diamine, caprolactam, glycerol, or 1,3-propanediol biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having 1,4-butanediol, 4-hydroxybutyrate, 1,3-butanediol, isopropanol, 6-aminocaproic acid, hexamethylene diamine, caprolactam, glycerol, or 1,3-propanediol biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the present invention provides a non-naturally occurring microbial organism that includes a microbial organism having a reductive TCA pathway in which at least one exogenous nucleic acid encoding a reductive TCA pathway enzyme is expressed in a sufficient amount to enhance carbon flux through acetyl-CoA. At least one exogenous nucleic acid is selected from an ATP-citrate lyase, citrate lyase, a fumarate reductase, and an alpha-ketoglutarate:ferredoxin oxidoreductase.

In some embodiments, the non-naturally occurring microbial organism includes two exogenous nucleic acids each encoding a reductive TCA pathway enzyme.

In some embodiments, the non-naturally occurring microbial organism includes three exogenous nucleic acids each encoding a reductive TCA pathway enzyme.

In some embodiments, the non-naturally occurring microbial organism includes three exogenous nucleic acids encoding an ATP-citrate lyase, a fumarate reductase, and an alpha-ketoglutarate:ferredoxin oxidoreductase.

In some embodiments, the non-naturally occurring microbial organism includes three exogenous nucleic acids encoding a citrate lyase, a fumarate reductase, and an alpha-ketoglutarate:ferredoxin oxidoreductase.

In some embodiments, the non-naturally occurring microbial organism includes at least one exogenous nucleic acid that is a heterologous nucleic acid.

In some embodiments, the non-naturally occurring microbial organism is in a substantially anaerobic culture medium.

In some embodiments, the non-naturally occurring microbial organism further includes an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, and combinations thereof.

In some embodiments, the non-naturally occurring microbial organism further induces an isopropanol pathway, the isopropanol pathway converting acetyl-CoA to isopropanol, wherein the isopropanol pathway includes 1) an acetoacetyl-CoA thiolase, 2) an acetoacetyl-CoA transferase, an acetoacetyl-CoA hydrolase, an acetoacetyl-CoA synthetase, or a phosphotransacetoacetylase/acetoacetate kinase, 3) an acetoacetate decarboxylase, and 4) an isopropanol dehydrogenase.

In some embodiments, the non-naturally occurring microbial organism includes at least one enzyme of the isopropanol pathway which is encoded by an exogenous nucleic acid.

In some embodiments, the non-naturally occurring microbial organism includes at least two enzymes of the isopropanol pathway which are encoded by exogenous nucleic acids.

In some embodiments, the non-naturally occurring microbial organism includes at least three enzymes of the isopropanol pathway which are encoded by exogenous nucleic acids.

In some embodiments, the non-naturally occurring microbial organism includes four enzymes of the isopropanol pathway which are encoded by exogenous nucleic acids.

In some embodiments, the non-naturally occurring microbial organism further includes a 1,3-butanediol pathway; said 1,3-butanediol pathway converting acetyl-CoA to 1,3-butanediol, wherein said 1,3-butanediol pathway comprises at least three enzymes selected from 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy, 2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

In some embodiments, the non-naturally occurring microbial organism includes at least one enzyme of the 1,3-butanediol pathway which is encoded by an exogenous nucleic acid.

In some embodiments, the non-naturally occurring microbial organism includes at least two enzymes of the 1,3-butanediol pathway are encoded by exogenous nucleic acids.

In some embodiments, the non-naturally occurring microbial organism includes at least three enzymes of the 1,3-butanediol pathway which are encoded by exogenous nucleic acids.

In some embodiments, the non-naturally occurring microbial organism further includes a 1,4-butanediol pathway, the 1,4-butanediol pathway converting acetyl-CoA to 1,4-butanediol, wherein the 1,4-butanediol pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

In some embodiments, the non-naturally occurring microbial organism includes at least one enzyme of the 1,4-butanediol pathway which is encoded by an exogenous nucleic acid.

In some embodiments, the non-naturally occurring microbial organism includes at least two enzymes of the 1,4-butanediol pathway which are encoded by exogenous nucleic acids.

In some embodiments, the non-naturally occurring microbial organism includes at least three enzymes of the 1,4-butanediol pathway which are encoded by exogenous nucleic acids.

In some embodiments, the non-naturally occurring microbial organism includes at least four enzymes of the 1,4-butanediol pathway which are encoded by exogenous nucleic acids.

In some embodiments, the non-naturally occurring microbial organism includes at least five enzymes of said 1,4-butanediol pathway which are encoded by exogenous nucleic acids.

In some embodiments, the non-naturally occurring microbial organism further includes a 4-hydroxybutyrate pathway, the 4-hydroxybutyrate pathway converting acetyl-CoA to 4-hydroxybutyrate, wherein the 4-hydroxybutyrate pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

In some embodiments, the non-naturally occurring microbial organism includes at least one enzyme of the 4-hydroxybutyrate pathway which is encoded by an exogenous nucleic acid.

In some embodiments, the non-naturally occurring microbial organism includes at least two enzymes of the 4-hydroxybutyrate pathway which are encoded by exogenous nucleic acids.

In some embodiments, the non-naturally occurring microbial organism includes at least three enzymes of the 4-hydroxybutyrate pathway which are encoded by exogenous nucleic acids.

In some embodiments, the non-naturally occurring microbial organism includes at least four enzymes of the 4-hydroxybutyrate pathway which are encoded by exogenous nucleic acids.

In some embodiments, the non-naturally occurring microbial organism includes at least five enzymes of the 4-hydroxybutyrate pathway which are encoded by exogenous nucleic acids.

In some embodiments, the non-naturally occurring microbial organism further includes an exogenous nucleic acid encoding an enzyme selected from carbon monoxide dehydrogenase, acetyl-CoA synthase, ferredoxin, NAD(P)H:ferredoxin oxidoreductase and combinations thereof.

In some embodiments, the non-naturally occurring microbial organism utilizes a carbon feedstock selected from CO, $CO_2$, $CO_2$ and $H_2$, synthesis gas comprising CO and $H_2$, and synthesis gas comprising CO, $CO_2$, and $H_2$.

In some embodiments, a non-naturally occurring microbial organism includes a microbial organism having a Wood-Ljungdahl pathway that includes at least one exogenous nucleic acid encoding a Wood-Ljungdahl pathway enzyme expressed in a sufficient amount to enhance carbon flux through acetyl-CoA. The at least one exogenous nucleic acid is selected from a) Formate dehydrogenase, b) Formyltetrahydrofolate synthetase, c) Methenyltetrahydrofolate cyclohydrolase, d) Methylenetetrahydrofolate dehydrogenase, e) Methylenetetrahydrofolate reductase, f) Methyltetrahydrofolate:corrinoid protein methyltransferase (AcsE), g) Corrinoid iron-sulfur protein (AcsD), h) Nickel-protein assembly protein (AcsF & CooC), i) Ferredoxin (Orf7), j) Acetyl-CoA synthase (AcsB & AcsC), k) Carbon monoxide dehydrogenase (AcsA), l) Pyruvate ferredoxin oxidoreductase or pyruvate dehydrogenase, m) Pyruvate formate lyase In some embodiments, the non-naturally occurring microbial organism includes two exogenous nucleic acids each encoding a Wood-Ljungdahl pathway enzyme.

In some embodiments, the non-naturally occurring microbial organism includes three exogenous nucleic acids each encoding a Wood-Ljungdahl pathway enzyme.

In some embodiments, the non-naturally occurring microbial organism includes four exogenous nucleic acids each encoding a Wood-Ljungdahl pathway enzyme.

In some embodiments, the non-naturally occurring microbial organism includes five exogenous nucleic acids each encoding a Wood-Ljungdahl pathway enzyme.

In some embodiments, the non-naturally occurring microbial organism includes six exogenous nucleic acids each encoding a Wood-Ljungdahl pathway enzyme.

In some embodiments, the non-naturally occurring microbial organism includes seven exogenous nucleic acids each encoding a Wood-Ljungdahl pathway enzyme.

In some embodiments, the non-naturally occurring microbial organism includes eight exogenous nucleic acids each encoding a Wood-Ljungdahl pathway enzyme.

In some embodiments, the non-naturally occurring microbial organism includes nine exogenous nucleic acids each encoding a Wood-Ljungdahl pathway enzyme.

In some embodiments, the non-naturally occurring microbial organism includes ten exogenous nucleic acids each encoding a Wood-Ljungdahl pathway enzyme.

In some embodiments, the non-naturally occurring microbial organism includes eleven exogenous nucleic acids each encoding a Wood-Ljungdahl pathway enzyme.

In some embodiments, the non-naturally occurring microbial organism includes twelve exogenous nucleic acids each encoding a Wood-Ljungdahl pathway enzyme.

In some embodiments, the non-naturally occurring microbial organism includes at least one exogenous nucleic acid that is a heterologous nucleic acid.

In some embodiments, the non-naturally occurring microbial organism includes is in a substantially anaerobic culture medium.

In some embodiments, the non-naturally occurring microbial organism further includes an isopropanol pathway, the isopropanol pathway converting acetyl-CoA to isopropanol. The isopropanol pathway includes 1) an acetoacetyl-CoA thiolase, 2) an acetoacetyl-CoA transferase, an acetoacetyl-CoA hydrolase, an acetoacetyl-CoA synthetase, or a phosphotransacetoacetylase/acetoacetate kinase, 3) an acetoacetate decarboxylase, and 4) an isopropanol dehydrogenase.

In some embodiments, the non-naturally occurring microbial organism includes at least one enzyme of the isopropanol pathway that is encoded by an exogenous nucleic acid.

In some embodiments, the non-naturally occurring microbial organism includes at least two enzymes of the isopropanol pathway which are encoded by exogenous nucleic acids.

In some embodiments, the non-naturally occurring microbial organism includes at least three enzymes of the isopropanol pathway which are encoded by exogenous nucleic acids.

In some embodiments, the non-naturally occurring microbial organism includes the four enzymes of the isopropanol pathway which are encoded by exogenous nucleic acids.

In some embodiments, the non-naturally occurring microbial organism further includes a 1,3-butanediol pathway; the 1,3-butanediol pathway converting acetyl-CoA to 1,3-butanediol. The 1,3-butanediol pathway includes at least three enzymes selected from 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy, 2-butanone reductase, 5) Acetoacetyl-CoA reductase (CoA-dependent, aldehyde forming), 6)

3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

In some embodiments, the non-naturally occurring microbial organism includes at least one enzyme of the 1,3-butanediol pathway that is encoded by an exogenous nucleic acid.

In some embodiments, the non-naturally occurring microbial organism includes at least two enzymes of the 1,3-butanediol pathway which are encoded by exogenous nucleic acids.

In some embodiments, the non-naturally occurring microbial organism includes at least three enzymes of the 1,3-butanediol pathway which are encoded by exogenous nucleic acids.

In some embodiments, the non-naturally occurring microbial organism further includes a 1,4-butanediol pathway, the 1,4-butanediol pathway converting acetyl-CoA to 1,4-butanediol. The 1,4-butanediol pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

In some embodiments, the non-naturally occurring microbial organism includes at least one enzyme of the 1,4-butanediol pathway that is encoded by an exogenous nucleic acid.

In some embodiments, the non-naturally occurring microbial organism includes at least two enzymes of the 1,4-butanediol pathway which are encoded by exogenous nucleic acids.

In some embodiments, the non-naturally occurring microbial organism includes at least three enzymes of the 1,4-butanediol pathway which are encoded by exogenous nucleic acids.

In some embodiments, the non-naturally occurring microbial organism includes at least four enzymes of the 1,4-butanediol pathway which are encoded by exogenous nucleic acids.

In some embodiments, the non-naturally occurring microbial organism includes at least five enzymes of the 1,4-butanediol pathway which are encoded by exogenous nucleic acids.

In some embodiments, the non-naturally occurring microbial organism further includes a 4-hydroxybutyrate pathway, the 4-hydroxybutyrate pathway converting acetyl-CoA to 4-hydroxybutyrate. The 4-hydroxybutyrate pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

In some embodiments, the non-naturally occurring microbial organism includes at least one enzyme of the 4-hydroxybutyrate pathway that is encoded by an exogenous nucleic acid.

In some embodiments, the non-naturally occurring microbial organism includes at least two enzymes of the 4-hydroxybutyrate pathway which are encoded by exogenous nucleic acids.

In some embodiments, the non-naturally occurring microbial organism includes at least three enzymes of the 4-hydroxybutyrate pathway which are encoded by exogenous nucleic acids.

In some embodiments, the non-naturally occurring microbial organism includes at least four enzymes of the 4-hydroxybutyrate pathway which are encoded by exogenous nucleic acids.

In some embodiments, the non-naturally occurring microbial organism includes at least five enzymes of the 4-hydroxybutyrate pathway which are encoded by exogenous nucleic acids.

In some embodiments, a non-naturally occurring microbial organism includes a microbial organism having a methanol Wood-Ljungdahl pathway that includes at least one exogenous nucleic acid encoding a Wood-Ljungdahl pathway enzyme expressed in a sufficient amount to enhance carbon flux through acetyl-CoA. The at least one exogenous nucleic acid is selected from a) Methanol methyltransferase (MtaB), b) Corrinoid protein (MtaC), c) Methyltetrahydrofolate:corrinoid protein methyltransferase (MtaA), d) Methyltetrahydrofolate:corrinoid protein methyltransferase (AcsE), e) Corrinoid iron-sulfur protein (AcsD), f) Nickel-protein assembly protein (AcsF & CooC), g) Ferredoxin (Orf7), h) Acetyl-CoA synthase (AcsB & AcsC), i) Carbon monoxide dehydrogenase (AcsA), j) Pyruvate ferredoxin oxidoreductase, k) NAD(P)H:ferredoxin oxidoreductase, l) Pyruvate dehydrogenase, m) Pyruvate formate lyase, n) Formate dehydrogenase.

In some embodiments, the non-naturally occurring microbial organism includes two exogenous nucleic acids each encoding a methanol Wood-Ljungdahl pathway enzyme.

In some embodiments, the non-naturally occurring microbial organism includes three exogenous nucleic acids each encoding a methanol Wood-Ljungdahl pathway enzyme.

In some embodiments, the non-naturally occurring microbial organism includes four exogenous nucleic acids each encoding a methanol Wood-Ljungdahl pathway enzyme.

In some embodiments, the non-naturally occurring microbial organism includes five exogenous nucleic acids each encoding a methanol Wood-Ljungdahl pathway enzyme.

In some embodiments, the non-naturally occurring microbial organism includes six exogenous nucleic acids each encoding a methanol Wood-Ljungdahl pathway enzyme.

In some embodiments, the non-naturally occurring microbial organism includes seven exogenous nucleic acids each encoding a methanol Wood-Ljungdahl pathway enzyme.

In some embodiments, the non-naturally occurring microbial organism includes eight exogenous nucleic acids each encoding a methanol Wood-Ljungdahl pathway enzyme.

In some embodiments, the non-naturally occurring microbial organism includes nine exogenous nucleic acids each encoding a methanol Wood-Ljungdahl pathway enzyme.

In some embodiments, the non-naturally occurring microbial organism includes ten exogenous nucleic acids each encoding a methanol Wood-Ljungdahl pathway enzyme.

In some embodiments, the non-naturally occurring microbial organism includes eleven exogenous nucleic acids each encoding a methanol Wood-Ljungdahl pathway enzyme.

In some embodiments, the non-naturally occurring microbial organism includes at least one exogenous nucleic acid that is a heterologous nucleic acid.

In some embodiments, the non-naturally occurring microbial organism is in a substantially anaerobic culture medium.

In some embodiments, the non-naturally occurring microbial organism further includes an isopropanol pathway, the isopropanol pathway converting acetyl-CoA to isopropanol. The isopropanol pathway includes 1) an acetoacetyl-CoA thiolase, 2) an acetoacetyl-CoA transferase, an acetoacetyl-CoA hydrolase, an acetoacetyl-CoA synthetase, or a phosphotransacetoacetylase/acetoacetate kinase, 3) an acetoacetate decarboxylase, and 4) an isopropanol dehydrogenase.

In some embodiments, the non-naturally occurring microbial organism includes at least one enzyme of the isopropanol pathway that is encoded by an exogenous nucleic acid.

In some embodiments, the non-naturally occurring microbial organism includes at least two enzymes of the isopropanol pathway which are encoded by exogenous nucleic acids.

In some embodiments, the non-naturally occurring microbial organism includes at least three enzymes of the isopropanol pathway which are encoded by exogenous nucleic acids.

In some embodiments, the non-naturally occurring microbial organism includes four enzymes of the isopropanol pathway which are encoded by exogenous nucleic acids.

In some embodiments, the non-naturally occurring microbial organism further includes a 1,3-butanediol pathway, the 1,3-butanediol pathway converting acetyl-CoA to 1,3-butanediol. The 1,3-butanediol pathway includes at least three enzymes selected from 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy, 2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

In some embodiments, the non-naturally occurring microbial organism includes at least one enzyme of the 1,3-butanediol pathway that is encoded by an exogenous nucleic acid.

In some embodiments, the non-naturally occurring microbial organism includes at least two enzymes of the 1,3-butanediol pathway which are encoded by exogenous nucleic acids.

In some embodiments, the non-naturally occurring microbial organism includes at least three enzymes of the 1,3-butanediol pathway which are encoded by exogenous nucleic acids.

In some embodiments, the non-naturally occurring microbial organism further includes a 1,4-butanediol pathway, the 1,4-butanediol pathway converting acetyl-CoA to 1,4-butanediol. The 1,4-butanediol pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

In some embodiments, the non-naturally occurring microbial organism includes at least one enzyme of the 1,4-butanediol pathway that is encoded by an exogenous nucleic acid.

In some embodiments, the non-naturally occurring microbial organism includes at least two enzymes of the 1,4-butanediol pathway which are encoded by exogenous nucleic acids.

In some embodiments, the non-naturally occurring microbial organism includes at least three enzymes of the 1,4-butanediol pathway which are encoded by exogenous nucleic acids.

In some embodiments, the non-naturally occurring microbial organism includes at least four enzymes of the 1,4-butanediol pathway which are encoded by exogenous nucleic acids.

In some embodiments, the non-naturally occurring microbial organism includes at least five enzymes of the 1,4-butanediol pathway which are encoded by exogenous nucleic acids.

In some embodiments, the non-naturally occurring microbial organism further includes a 4-hydroxybutyrate pathway, the 4-hydroxybutyrate pathway converting acetyl-CoA to 4-hydroxybutyrate. The 4-hydroxybutyrate pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

In some embodiments, the non-naturally occurring microbial organism includes at least one enzyme of the 4-hydroxybutyrate pathway that is encoded by an exogenous nucleic acid.

In some embodiments, the non-naturally occurring microbial organism includes at least two enzymes of the 4-hydroxybutyrate pathway which are encoded by exogenous nucleic acids.

In some embodiments, the non-naturally occurring microbial organism includes at least three enzymes of the 4-hydroxybutyrate pathway which are encoded by exogenous nucleic acids.

In some embodiments, the non-naturally occurring microbial organism includes at least four enzymes of the 4-hydroxybutyrate pathway which are encoded by exogenous nucleic acids.

In some embodiments, the non-naturally occurring microbial organism includes at least five enzymes of the 4-hydroxybutyrate pathway which are encoded by exogenous nucleic acids.

In some embodiments, the present invention provides a non-naturally occurring microbial organism that includes at least one exogenous nucleic acid encoding an enzyme expressed in a sufficient amount to enhance the availability of reducing equivalents in the presence of carbon monoxide or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H: ferredoxin oxidoreductase, and a ferredoxin.

In some embodiments, the non-naturally occurring microbial organism includes two exogenous nucleic acids.

In some embodiments, the non-naturally occurring microbial organism includes three exogenous nucleic acids.

In some embodiments, the non-naturally occurring microbial organism includes four exogenous nucleic acids.

In some embodiments, the non-naturally occurring microbial organism includes four exogenous nucleic acids encoding a carbon monoxide dehydrogenase, a hydrogenase, an NAD(P)H:ferredoxin oxidoreductase, and a ferredoxin.

In some embodiments, the non-naturally occurring microbial organism includes at least one exogenous nucleic acid that is a heterologous nucleic acid.

In some embodiments, the non-naturally occurring microbial organism is in a substantially anaerobic culture medium.

In some embodiments, the non-naturally occurring microbial organism further includes one or more nucleic acids encoding an enzyme selected from a phosphoenolpyruvate carboxylase, a phosphoenolpyruvate carboxykinase, a pyruvate carboxylase, and a malic enzyme.

In some embodiments, the non-naturally occurring microbial organism further includes one or more nucleic acids encoding an enzyme selected from a malate dehydrogenase, a fumarase, a fumarate reductase, a succinyl-CoA synthetase, and a succinyl-CoA transferase.

In some embodiments, the non-naturally occurring microbial organism includes a 1,4-butanediol pathway that includes at least one exogenous nucleic acid encoding an enzyme selected from 1) Hydrogenase, 2) Carbon monoxide dehydrogenase, 3) Succinyl-CoA transferase, Succinyl-CoA hydrolase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA reductase (aldehyde forming), 9) 1,4-butanediol dehydrogenase, 10) Succinate reductase, 11) Succinyl-CoA reductase (alcohol forming), 12) 4-Hydroxybutyryl-CoA transferase, 4-Hydroxybutyryl-CoA hydrolase, or 4-Hydroxybutyryl-CoA synthetase, 13) 4-Hydroxybutyrate reductase, 14) 4-Hydroxybutyryl-phosphate reductase, and 15) 4-Hydroxybutyryl-CoA reductase (alcohol forming).

In some embodiments, the non-naturally occurring microbial organism further includes a 1,3-butanediol pathway comprising at least one exogenous nucleic acid encoding an enzyme selected from: 1) Hydrogenase, 2) Carbon monoxide dehydrogenase, 3) Succinyl-CoA transferase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA dehydratase, 9) Crotonase, 10) 3-Hydroxybutyryl-CoA reductase (aldehyde forming), 11) 3-Hydroxybutyraldehyde reductase, 12) Succinate reductase, 13) Succinyl-CoA reductase (alcohol forming), 14) 4-Hydroxybutyryl-CoA transferase, or 4-Hydroxybutyryl-CoA synthetase, 15) 3-Hydroxybutyryl-CoA reductase (alcohol forming), 16) 3-Hydroxybutyryl-CoA hydrolase, or 3-Hydroxybutyryl-CoA synthetase, or 3-Hydroxybutyryl-CoA transferase, 17) 3-Hydroxybutyrate reductase In some embodiments, the non-naturally occurring microbial organism includes a butanol pathway that includes at least one exogenous nucleic acid encoding an enzyme selected from 1) Hydrogenase, 2) Carbon monoxide dehydrogenase, 3) Succinyl-CoA transferase, or Succinyl-CoA synthetase (or succinyl-CoA ligase), 4) Succinyl-CoA reductase (aldehyde forming), 5) 4-Hydroxybutyrate dehydrogenase, 6) 4-Hydroxybutyrate kinase, 7) Phosphotrans-4-hydroxybutyrylase, 8) 4-Hydroxybutyryl-CoA dehydratase, 9) butyryl-CoA dehydrogenase, 10) Butyryl-CoA reductase (aldehyde forming), 11) Butyraldehyde reductase, 12) Succinate reductase, 13) Succinyl-CoA reductase (alcohol forming), 14) 4-Hydroxybutyryl-CoA transferase, or 4-Hydroxybutyryl-CoA synthetase, 15) Butyryl-CoA reductase (alcohol forming), 16) Butyryl-CoA hydrolase, or Butyryl-CoA synthetase, or Butyryl-CoA transferase, 17) Butyrate reductase.

In some embodiments, the non-naturally occurring microbial organism further includes a 6-aminocaproic acid pathway that includes at least one exogenous nucleic acid encoding an enzyme selected from 1) Hydrogenase, 2) Carbon monoxide dehydrogenase, 3) 3-Oxoadipyl-CoA thiolase, 4) 3-Oxoadipyl-CoA reductase, 5) 3-Hydroxyadipyl-CoA dehydratase, 6) 5-Carboxy-2-pentenoyl-CoA reductase, 7) Adipyl-CoA reductase (aldehyde forming), and 8) 6-Aminocaproate transaminase, or 6-Aminocaproate dehydrogenase.

In some embodiments, the non-naturally occurring microbial organism further includes a hexamethylenediamine pathway comprising at least one exogenous nucleic acid encoding an enzyme selected from 1) Hydrogenase, 2) Carbon monoxide dehydrogenase, 3) 3-Oxoadipyl-CoA thiolase, 4) 3-Oxoadipyl-CoA reductase, 5) 3-Hydroxyadipyl-CoA dehydratase, 6) 5-Carboxy-2-pentenoyl-CoA reductase, 7) Adipyl-CoA reductase (aldehyde forming), 8) 6-Aminocaproate transaminase, or 6-Aminocaproate dehydrogenase, 9) 6-Aminocaproyl-CoA/acyl-CoA transferase, or 6-Aminocaproyl-CoA synthase, 10) 6-Aminocaproyl-CoA reductase (aldehyde forming), and 11) HMDA transaminase, or HMDA dehydrogenase.

In some embodiments, the non-naturally occurring microbial organism includes an adipic acid pathway.

In some embodiments, the non-naturally occurring microbial organism further includes a caprolactam pathway that includes at least one exogenous nucleic acid encoding an enzyme selected from 1) Hydrogenase, 2) Carbon monoxide dehydrogenase, 3) 3-Oxoadipyl-CoA thiolase, 4) 3-Oxoadipyl-CoA reductase, 5) 3-Hydroxyadipyl-CoA dehydratase, 6) 5-Carboxy-2-pentenoyl-CoA reductase, 7) Adipyl-CoA reductase (aldehyde forming), 8) 6-Aminocaproate transaminase, or 6-Aminocaproate dehydrogenase, 9) 6-Aminocaproyl-CoA/acyl-CoA transferase, or 6-Aminocaproyl-CoA synthase, 10) amidohydrolase, and 11) Spontaneous cyclization.

In some embodiments, the non-naturally occurring microbial organism further includes a glycerol pathway that includes at least one exogenous nucleic acid encoding an enzyme selected from 1) Hydrogenase, 2) Carbon monoxide dehydrogenase, 3) Dihydroxyacetone kinase, and 4) Glycerol dehydrogenase.

In some embodiments, the non-naturally occurring microbial organism includes a 1,3-propanediol pathway that at least one exogenous nucleic acid encoding an enzyme selected from 1) Hydrogenase, 2) Carbon monoxide dehydrogenase, 3) Dihydroxyacetone kinase, 4) Glycerol dehydrogenase, 5) Glycerol dehydratase, and 6) 1,3-Propanediol dehydrogenase.

In some embodiments, the non-naturally occurring microbial organism includes a microbial organism having: a reductive TCA pathway that includes at least one exogenous nucleic acid encoding a reductive TCA pathway enzyme; the at least one exogenous nucleic acid is selected from an ATP-citrate lyase, a citrate lyase, a fumarate reductase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of 1) CO, 2) $CO_2$ and $H_2$, 3) CO and $CO_2$, 4) synthesis gas comprising CO and $H_2$, and 5) synthesis gas comprising CO, $CO_2$, and $H_2$.

In some embodiments, the non-naturally occurring microbial organism further includes at least one exogenous nucleic acid encoding a citrate lyase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, and a ferredoxin.

In some embodiments, the non-naturally occurring microbial organism further includes an isopropanol pathway, the isopropanol pathway converting acetyl-CoA to isopropanol, The isopropanol pathway includes 1) an acetoacetyl-CoA thiolase, 2) an acetoacetyl-CoA transferase, an acetoacetyl-CoA hydrolase, an acetoacetyl-CoA synthetase, or a phosphotransacetoacetylase/acetoacetate kinase, 3) an acetoacetate decarboxylase, and 4) an isopropanol dehydrogenase.

In some embodiments, the non-naturally occurring microbial organism includes at least one enzyme of the isopropanol pathway that is encoded by an exogenous nucleic acid.

In some embodiments, the non-naturally occurring microbial organism includes at least two enzymes of the isopropanol pathway which are encoded by exogenous nucleic acids.

In some embodiments, the non-naturally occurring microbial organism includes at least three enzymes of the isopropanol pathway which are encoded by exogenous nucleic acids.

In some embodiments, the non-naturally occurring microbial organism includes four enzymes of the isopropanol pathway which are encoded by exogenous nucleic acids.

In some embodiments, the non-naturally occurring microbial organism further includes a 1,3-butanediol pathway, the 1,3-butanediol pathway converting acetyl-CoA to 1,3-butanediol. The 1,3-butanediol pathway includes at least three enzymes selected from 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy, 2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.

In some embodiments, the non-naturally occurring microbial organism includes at least one enzyme of the 1,3-butanediol pathway that is encoded by an exogenous nucleic acid.

In some embodiments, the non-naturally occurring microbial organism includes at least two enzymes of the 1,3-butanediol pathway which are encoded by exogenous nucleic acids.

In some embodiments, the non-naturally occurring microbial organism includes at least three enzymes of the 1,3-butanediol pathway which are encoded by exogenous nucleic acids.

In some embodiments, the non-naturally occurring microbial organism further includes a 1,4-butanediol pathway, the 1,4-butanediol pathway converting acetyl-CoA to 1,4-butanediol. The 1,4-butanediol pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

In some embodiments, the non-naturally occurring microbial organism includes at least one enzyme of the 1,4-butanediol pathway that is encoded by an exogenous nucleic acid.

In some embodiments, the non-naturally occurring microbial organism includes at least two enzymes of the 1,4-butanediol pathway which are encoded by exogenous nucleic acids.

In some embodiments, the non-naturally occurring microbial organism includes at least three enzymes of the 1,4-butanediol pathway which are encoded by exogenous nucleic acids.

In some embodiments, the non-naturally occurring microbial organism includes at least four enzymes of the 1,4-butanediol pathway which are encoded by exogenous nucleic acids.

In some embodiments, the non-naturally occurring microbial organism includes at least five enzymes of the 1,4-butanediol pathway which are encoded by exogenous nucleic acids.

In some embodiments, the non-naturally occurring microbial organism further includes a 4-hydroxybutyrate pathway, the 4-hydroxybutyrate pathway converting acetyl-CoA to 4-hydroxybutyrate. The 4-hydroxybutyrate pathway includes at least five enzymes selected from 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.

In some embodiments, the non-naturally occurring microbial organism includes at least one enzyme of the 4-hydroxybutyrate pathway that is encoded by an exogenous nucleic acid.

In some embodiments, the non-naturally occurring microbial organism includes at least two enzymes of the 4-hydroxybutyrate pathway which are encoded by exogenous nucleic acids.

In some embodiments, the non-naturally occurring microbial organism includes at least three enzymes of the 4-hydroxybutyrate pathway which are encoded by exogenous nucleic acids.

In some embodiments, the non-naturally occurring microbial organism includes at least four enzymes of the 4-hydroxybutyrate pathway which are encoded by exogenous nucleic acids.

In some embodiments, the non-naturally occurring microbial organism includes at least five enzymes of the 4-hydroxybutyrate pathway which are encoded by exogenous nucleic acids.

Enzymes of the reductive TCA cycle useful in the non-naturally occurring microbial organisms of the present invention include one or more of ATP-citrate lyase and three CO2-fixing enzymes: isocitrate dehydrogenase, alpha-ketoglutarate:ferredoxin oxidoreductase, pyruvate:ferredoxin oxidoreductase. The presence of ATP-citrate lyase or citrate lyase and alpha-ketoglutarate:ferredoxin oxidoreductase indicates the presence of an active reductive TCA cycle in an organism. Enzymes for each of these steps are shown below.

ATP citrate lyase (ACL, EC 2.3.3.8), also called ATP citrate synthase, catalyzes the ATP-dependent cleavage of citrate to oxaloacetate and acetyl-CoA. ACL is an enzyme of the RTCA cycle that has been studied in green sulfur bacteria *Chlorobium limicola* and *Chlorobium tepidum*. The alpha (4)beta(4) heteromeric enzyme from *Chlorobium limicola* was cloned and characterized in *E. coli* (Kanao et al., *Eur. J. Biochem.* 269:3409-3416 (2002). The *C. limicola* enzyme, encoded by aclAB, is irreversible and activity of the enzyme is regulated by the ratio of ADP/ATP. The *Chlorobium tepidum* a recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188:6544-6552 (2006). ACL enzymes have also been identified in *Balnearium lithotrophicum, Sulfurihydrogenibium subterraneum* and other members of the bacterial phylum Aquificae (Hugler et al., *Environ. Microbiol.* 9:81-92 (2007)). This activity has been reported in some fungi as well. Exemplary organisms include *Sordaria macrospora* (Nowrousian et al., *Curr. Genet.* 37:189-93 (2000), *Aspergillus nidulans* and *Yarrowia lipolytica* (Hynes and Murray, *Eukaryotic Cell*, July: 1039-1048, (2010), and *Aspergillus niger* (Meijer et al. *J. Ind. Microbiol. Biotechnol.* 36:1275-1280 (2009). Other candidates can be found based on sequence homology. Information related to these enzymes is tabulated below:

| Protein | GenBank ID | GI Number | Organism |
|---|---|---|---|
| aclA | BAB21376.1 | 12407237 | *Chlorobium limicola* |
| aclB | BAB21375.1 | 12407235 | *Chlorobium limicola* |
| aclA | AAM72321.1 | 21647054 | *Chlorobium tepidum* |
| aclB | AAM72322.1 | 21647055 | *Chlorobium tepidum* |
| aclA | ABI50076.1 | 114054981 | *Balnearium lithotrophicum* |
| aclB | ABI50075.1 | 114054980 | *Balnearium lithotrophicum* |
| aclA | ABI50085.1 | 114055040 | *Sulfurihydrogenibium subterraneum* |
| aclB | ABI50084.1 | 114055039 | *Sulfurihydrogenibium subterraneum* |
| aclA | AAX76834.1 | 62199504 | *Sulfurimonas denitrificans* |
| aclB | AAX76835.1 | 62199506 | *Sulfurimonas denitrificans* |
| acl1 | XP_504787.1 | 50554757 | *Yarrowia lipolytica* |
| acl2 | XP_503231.1 | 50551515 | *Yarrowia lipolytica* |
| SPBC1703.07 | NP_596202.1 | 19112994 | *Schizosaccharomyces pombe* |
| SPAC22A12.16 | NP_593246.1 | 19114158 | *Schizosaccharomyces pombe* |
| acl1 | CAB76165.1 | 7160185 | *Sordaria macrospora* |
| acl2 | CAB76164.1 | 7160184 | *Sordaria macrospora* |
| aclA | CBF86850.1 | 259487849 | *Aspergillus nidulans* |
| aclB | CBF86848 | 259487848 | *Aspergillus nidulans* |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., *Appl. Microbiol. Biotechnol.* 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., *Mol. Micrbiol.* 52:751-761 (2004)). The citryl-CoA synthetase of *Aquifex aeolicus* is composed of alpha and beta subunits encoded by sucC1 and sucD1 (Hugler et al., *Environ. Microbiol.* 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., *Mol. Microbiol.* 52:763-770 (2004)) and aq_150 in *Aquifex aeolicus* (Hugler et al., supra (2007)). The genes for this mechanism of converting citrate to oxaloacetate and citryl-CoA have also been reported recently in *Chlorobium tepidum* (Eisen et al., *PNAS* 99(14): 9509-14 (2002).

| Protein | GenBank ID | GI Number | Organism |
|---|---|---|---|
| ccsA | BAD17844.1 | 46849514 | *Hydrogenobacter thermophilus* |
| ccsB | BAD17846.1 | 46849517 | *Hydrogenobacter thermophilus* |
| sucC1 | AAC07285 | 2983723 | *Aquifex aeolicus* |
| sucD1 | AAC07686 | 2984152 | *Aquifex aeolicus* |
| ccl | BAD17841.1 | 46849510 | *Hydrogenobacter thermophilus* |
| aq_150 | AAC06486 | 2982866 | *Aquifex aeolicus* |
| CT0380 | NP_661284 | 21673219 | *Chlorobium tepidum* |
| CT0269 | NP_661173.1 | 21673108 | *Chlorobium tepidum* |
| CT1834 | AAM73055.1 | 21647851 | *Chlorobium tepidum* |

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278:25628-25636 (2003)), and MDH3 (Steffan and McAlister-Henn, *J. Biol. Chem.* 267:24708-24715 (1992)), which localize to the mitochondrion, cytosol, and peroxisome, respectively. *E. coli* is known to have an active malate dehydrogenase encoded by mdh.

| Protein | GenBank ID | GI Number | Organism |
|---|---|---|---|
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| Mdh | NP_417703.1 | 16131126 | *Escherichia coli* |

Fumarate hydratase (EC 4.2.1.2) catalyzes the reversible hydration of fumarate to malate. The three fumarases of *E. coli*, encoded byfumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., *J. Bacteriol.* 183:461-467 (2001); Woods et al., *Biochim. Biophys. Acta* 954:14-26 (1988); Guest et al., *J. Gen. Microbiol.* 131:2971-2984 (1985)). *S. cerevisiae* contains one copy of a fumarase-encoding gene, FUM1, whose product localizes to both the cytosol and mitochondrion (Sass et al., *J. Biol. Chem.* 278:45109-45116 (2003)). Additional fumarase enzymes are found in *Campylobacter jejuni* (Smith et al., *Int. J. Biochem. Cell. Biol.* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol. Lett.* 270:207-213 (2007)).

| Protein | GenBank ID | GI Number | Organism |
|---|---|---|---|
| fumA | NP_416129.1 | 16129570 | *Escherichia coli* |
| fumB | NP_418546.1 | 16131948 | *Escherichia coli* |

| Protein | GenBank ID | GI Number | Organism |
|---|---|---|---|
| fumC | NP_416128.1 | 16129569 | Escherichia coli |
| FUM1 | NP_015061 | 6324993 | Saccharomyces cerevisiae |
| fumC | Q8NRN8.1 | 39931596 | Corynebacterium glutamicum |
| fumC | O69294.1 | 9789756 | Campylobacter jejuni |
| fumC | P84127 | 75427690 | Thermus thermophilus |
| fumH | P14408.1 | 120605 | Rattus norvegicus |
| MmcB | YP_001211906 | 147677691 | Pelotomaculum thermopropionicum |
| MmcC | YP_001211907 | 147677692 | Pelotomaculum thermopropionicum |

Fumarate reductase catalyzes the reduction of fumarate to succinate. The fumarate reductase of E. coli, composed of four subunits encoded by frdABCD, is membrane-bound and active under anaerobic conditions. The electron donor for this reaction is menaquinone and the two protons produced in this reaction do not contribute to the proton gradient (Iverson et al., Science 284:1961-1966 (1999)). The yeast genome encodes two soluble fumarate reductase isozymes encoded by FRDS1 (Enomoto et al., DNA Res. 3:263-267 (1996)) and FRDS2 (Muratsubaki et al., Arch. Biochem. Biophys. 352:175-181 (1998)), which localize to the cytosol and promitochondrion, respectively, and are used for anaerobic growth on glucose (Arikawa et al., FEMS Microbiol. Lett. 165:111-116 (1998)).

| Protein | GenBank ID | GI Number | Organism |
|---|---|---|---|
| FRDS1 | P32614 | 418423 | Saccharomyces cerevisiae |
| FRDS2 | NP_012585 | 6322511 | Saccharomyces cerevisiae |
| frdA | NP_418578.1 | 16131979 | Escherichia coli |
| frdB | NP_418577.1 | 16131978 | Escherichia coli |
| frdC | NP_418576.1 | 16131977 | Escherichia coli |
| frdD | NP_418475.1 | 16131877 | Escherichia coli |

The ATP-dependent acylation of succinate to succinyl-CoA is catalyzed by succinyl-CoA synthetase (EC 6.2.1.5). The product of the LSC1 and LSC2 genes of S. cerevisiae and the sucC and sucD genes of E. coli naturally form a succinyl-CoA synthetase complex that catalyzes the formation of succinyl-CoA from succinate with the concomitant consumption of one ATP, a reaction which is reversible in vivo (Buck et al., Biochemistry 24:6245-6252 (1985)). These proteins are identified below:

| Protein | GenBank ID | GI Number | Organism |
|---|---|---|---|
| LSC1 | NP_014785 | 6324716 | Saccharomyces cerevisiae |
| LSC2 | NP_011760 | 6321683 | Saccharomyces cerevisiae |
| sucC | NP_415256.1 | 16128703 | Escherichia coli |
| sucD | AAC73823.1 | 1786949 | Escherichia coli |

Alpha-ketoglutarate:ferredoxin oxidoreductase (EC 1.2.7.3), also known as 2-oxoglutarate synthase or 2-oxoglutarate:ferredoxin oxidoreductase (OFOR), forms alpha-ketoglutarate from $CO_2$ and succinyl-CoA with concurrent consumption of two reduced ferredoxin equivalents. OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., Archaea. Adv. Protein Chem. 48:101-180 (1996)). Enzymes in this class are reversible and function in the carboxylation direction in organisms that fix carbon by the RTCA cycle such as Hydrogenobacter thermophilus, Desulfobacter hydrogenophilus and Chlorobium species (Shiba et al. 1985; Evans et al., Proc. Natl. Acad. Sci. U.S.A. 55:92934 (1966); Buchanan, 1971). The two-subunit enzyme from H. thermophilus enzyme, encoded by korAB, has been cloned and expressed in E. coli (Yun et al., Biochem. Biophys. Res. Commun. 282:589-594 (2001)). A five subunit OFOR from the same organism with strict substrate specificity for succinyl-CoA, encoded by for DABGE, was recently identified and expressed in E. coli (Yun et al. 2002). The kinetics of CO2 fixation of both H. thermophilus OFOR enzymes have been characterized (Yamamoto et al., Extremophiles 14:79-85 (2010)). A CO2-fixing OFOR from Chlorobium thiosulfatophilum has been purified and characterized but the genes encoding this enzyme have not been identified to date. Enzyme candidates in Chlorobium species can be inferred by sequence similarity to the H. thermophilus genes. For example, the Chlorobium limicola genome encodes two similar proteins. Acetogenic bacteria such as Moorella thermoacetica are predicted to encode two OFOR enzymes. The enzyme encoded by Moth_0034 is predicted to function in the CO2-assimilating direction. The genes associated with this enzyme, Moth_0034 have not been experimentally validated to date but can be inferred by sequence similarity to known OFOR enzymes.

OFOR enzymes that function in the decarboxylation direction under physiological conditions can also catalyze the reverse reaction. The OFOR from the thermoacidophilic archaeon Sulfolobus sp. strain 7, encoded by ST2300, has been extensively studied (Zhang et al. 1996. A plasmid-based expression system has been developed for efficiently expressing this protein in E. coli (Fukuda et al., Eur. J. Biochem. 268:5639-5646 (2001)) and residues involved in substrate specificity were determined (Fukuda and Wakagi, Biochim. Biophys. Acta 1597:74-80 (2002)). The OFOR encoded by Ape1472/Ape1473 from Aeropyrum pernix str. K1 was recently cloned into E. coli, characterized, and found to react with 2-oxoglutarate and a broad range of 2-oxoacids (Nishizawa et al., FEBS Lett. 579:2319-2322 (2005)). Another exemplary OFOR is encoded by oorDABC in Helicobacter pylori (Hughes et al. 1998). An enzyme very specific to alpha-ketoglutarate has been reported in Thauera aromatics (Dorner and Boll, J, Bacteriol. 184 (14), 3975-83 (2002). A similar enzyme can be found in Rhodospirillum rubrum by sequence homology. A two subunit enzyme has also been identified in Chlorobium tepidum (Eisen et al., PNAS 99(14): 9509-14 (2002)).

| Protein | GenBank ID | GI Number | Organism |
|---|---|---|---|
| korA | BAB21494 | 12583691 | Hydrogenobacter thermophilus |
| korB | BAB21495 | 12583692 | Hydrogenobacter thermophilus |
| forD | BAB62132.1 | 14970994 | Hydrogenobacter thermophilus |
| forA | BAB62133.1 | 14970995 | Hydrogenobacter thermophilus |
| forB | BAB62134.1 | 14970996 | Hydrogenobacter thermophilus |
| forG | BAB62135.1 | 14970997 | Hydrogenobacter thermophilus |
| forE | BAB62136.1 | 14970998 | Hydrogenobacter thermophilus |
| Clim_0204 | ACD89303.1 | 189339900 | Chlorobium limicola |
| Clim_0205 | ACD89302.1 | 189339899 | Chlorobium limicola |
| Clim_1123 | ACD90192.1 | 189340789 | Chlorobium limicola |
| Clim_1124 | ACD90193.1 | 189340790 | Chlorobium limicola |
| Moth_1984 | YP_430825.1 | 83590816 | Moorella thermoacetica |
| Moth_1985 | YP_430826.1 | 83590817 | Moorella thermoacetica |
| Moth_0034 | YP_428917.1 | 83588908 | Moorella thermoacetica |
| ST2300 | NP_378302.1 | 15922633 | Sulfolobus sp. strain 7 |
| Ape1472 | BAA80470.1 | 5105156 | Aeropyrum pernix |

| Protein | GenBank ID | GI Number | Organism |
|---|---|---|---|
| Ape1473 | BAA80471.2 | 116062794 | Aeropyrum pernix |
| oorD | AAC38210.1 | 2935178 | Helicobacter pylori |
| oorA | AAC38211.1 | 2935179 | Helicobacter pylori |
| oorB | AAC38212.1 | 2935180 | Helicobacter pylori |
| oorC | AAC38213.1 | 2935181 | Helicobacter pylori |
| CT0163 | NP_661069.1 | 21673004 | Chlorobium tepidum |
| CT0162 | NP_661068.1 | 21673003 | Chlorobium tepidum |
| korA | CAA12243.2 | 19571179 | Thauera aromatics |
| korB | CAD27440.1 | 19571178 | Thauera aromatics |
| Rru_A2721 | YP_427805.1 | 83594053 | Rhodospirillum rubrum |
| Rru_A2722 | YP_427806.1 | 83594054 | Rhodospirillum rubrum |

Isocitrate dehydrogenase catalyzes the reversible decarboxylation of isocitrate to 2-oxoglutarate coupled to the reduction of $NAD(P)^+$. IDH enzymes in Saccharomyces cerevisiae and Escherichia coli are encoded by IDP1 and icd, respectively (Haselbeck and McAlister-Henn, J. Biol. Chem. 266:2339-2345 (1991); Nimmo, H. G., Biochem. J. 234:317-2332 (1986)). The reverse reaction in the reductive TCA cycle, the reductive carboxylation of 2-oxoglutarate to isocitrate, is favored by the NADPH-dependent $CO_2$-fixing IDH from Chlorobium limicola and was functionally expressed in E. coli (Kanao et al., Eur. J. Biochem. 269: 1926-1931 (2002)). A similar enzyme with 95% sequence identity is found in the C. tepidum genome in addition to some other candidates listed below.

| Protein | GenBank ID | GI Number | Organism |
|---|---|---|---|
| Icd | ACI84720.1 | 209772816 | Escherichia coli |
| IDP1 | AAA34703.1 | 171749 | Saccharomyces cerevisiae |
| Idh | BAC00856.1 | 21396513 | Chlorobium limicola |
| Icd | AAM71597.1 | 21646271 | Chlorobium tepidum |
| icd | NP_952516.1 | 39996565 | Geobacter sulfurreducens |
| icd | YP_393560. | 78777245 | Sulfurimonas denitrificans |

In H. thermophilus the reductive carboxylation of 2-oxoglutarate is catalyzed by two enzymes: 2-oxoglutarate carboxylase and oxalosuccinate reductase. 2-Oxoglutarate carboxylase (EC 6.4.1.7) catalyzes the ATP-dependent carboxylation of alpha-ketoglutarate to oxalosuccinate (Aoshima and Igarashi, Mol. Microbiol. 62:748-759 (2006)). This enzyme is a large complex composed of two subunits. Biotinylation of the large (A) subunit is required for enzyme function (Aoshima et al., Mol. Microbiol. 51:791-798 (2004)). Oxalosuccinate reductase (EC 1.1.1.-) catalyzes the NAD-dependent conversion of oxalosuccinate to D-threo-isocitrate. The enzyme is a homodimer encoded by icd in H. thermophilus. The kinetic parameters of this enzyme indicate that the enzyme only operates in the reductive carboxylation direction in vivo, in contrast to isocitrate dehydrogenase enzymes in other organisms (Aoshima and Igarashi, J. Bacteriol. 190:2050-2055 (2008)). Based on sequence homology, gene candidates have also been found in Thiobacillus denitrificans and Thermocrinis albus.

| Protein | GenBank ID | GI Number | Organism |
|---|---|---|---|
| cfiA | BAF34932.1 | 116234991 | Hydrogenobacter thermophilus |
| cifB | BAF34931.1 | 116234990 | Hydrogenobacter thermophilus |
| Icd | BAD02487.1 | 38602676 | Hydrogenobacter thermophilus |
| Tbd_1556 | YP_315314 | 74317574 | Thiobacillus denitrificans |
| Tbd_1555 | YP_315313 | 74317573 | Thiobacillus denitrificans |
| Tbd_0854 | YP_314612 | 74316872 | Thiobacillus denitrificans |
| Thal_0268 | YP_003473030 | 289548042 | Thermocrinis albus |
| Thal_0267 | YP_003473029 | 289548041 | Thermocrinis albus |
| Thal_0646 | YP_003473406 | 289548418 | Thermocrinis albus |

Aconitase (EC 4.2.1.3) is an iron-sulfur-containing protein catalyzing the reversible isomerization of citrate and iso-citrate via the intermediate cis-aconitate. Two aconitase enzymes are encoded in the E. coli genome by acnA and acnB. AcnB is the main catabolic enzyme, while AcnA is more stable and appears to be active under conditions of oxidative or acid stress (Cunningham et al., Microbiology 143 (Pt 12):3795-3805 (1997)). Two isozymes of aconitase in Salmonella typhimurium are encoded by acnA and acnB (Horswill and Escalante-Semerena, Biochemistry 40:4703-4713 (2001)). The S. cerevisiae aconitase, encoded by ACO1, is localized to the mitochondria where it participates in the TCA cycle (Gangloff et al., Mol. Cell. Biol. 10:3551-3561 (1990)) and the cytosol where it participates in the glyoxylate shunt (Regev-Rudzki et al., Mol. Biol. Cell. 16:4163-4171 (2005)).

| Protein | GenBank ID | GI Number | Organism |
|---|---|---|---|
| acnA | AAC7438.1 | 1787531 | Escherichia coli |
| acnB | AAC73229.1 | 2367097 | Escherichia coli |
| acnA | NP_460671.1 | 16765056 | Salmonella typhimurium |
| acnB | NP_459163.1 | 16763548 | Salmonella typhimurium |
| ACO1 | AAA34389.1 | 170982 | Saccharomyces cerevisiae |

Pyruvate ferredoxin oxidoreductase (PFOR) catalyzes the oxidation of pyruvate to form acetyl-CoA. The PFOR from Desulfovibrio africanus has been cloned and expressed in E. coli resulting in an active recombinant enzyme that was stable for several days in the presence of oxygen (Pieulle et al., J. Bacteriol. 179:5684-5692 (1997)). Oxygen stability is relatively uncommon in PFORs and is believed to be conferred by a 60 residue extension in the polypeptide chain of the D. africanus enzyme. Two cysteine residues in this enzyme form a disulfide bond that protects it against inactivation in the form of oxygen. This disulfide bond and the stability in the presence of oxygen has been found in other Desulfovibrio species also (Vita et al., Biochemistry, 47: 957-64 (2008)). The M. thermoacetica PFOR is also well characterized (Menon and Ragsdale, Biochemistry 36:8484-8494 (1997)) and was shown to have high activity in the direction of pyruvate synthesis during autotrophic growth (Furdui and Ragsdale, J. Biol. Chem. 275:28494-28499 (2000)). Further, E. coli possesses an uncharacterized open reading frame, ydbK, that encodes a protein that is 51% identical to the M. thermoacetica PFOR. Evidence for pyruvate oxidoreductase activity in E. coli has been described (Blaschkowski et al., Eur. J. Biochem. 123:563-569 (1982)). PFORs have also been described in other organisms, including, Rhodobacter capsulatas (Yakunin and Hallenbeck, Biochimica et Biophysica Acta 1409 (1998) 39-49 (1998)) and Choloboum tepidum (Eisen et al., PNAS 99(14): 9509-14 (2002)). The five subunit PFOR from H. thermophilus, encoded by porEDABG, was cloned into E. coli and shown to function in both the decarboxylating and $CO_2$-assimilating directions (Ikeda et al. 2006; Yamamoto et al., Extremophiles 14:79-85 (2010)). Homologs also exist in C. carboxidivorans P7. The protein sequences of these exemplary PFOR enzymes can be identified by the following GenBank accession numbers. Several additional PFOR enzymes are described in the following review (Ragsdale, S. W., Chem. Rev. 103:2333-2346 (2003)). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR. These proteins are identified below.

| Protein | GenBank ID | GI Number | Organism |
|---|---|---|---|
| Por | CAA70873.1 | 1770208 | *Desulfovibrio africanus* |
| por | YP_012236.1 | 46581428 | *Desulfovibrio vulgaris* str. Hildenborough |
| Dde_3237 | ABB40031.1 | 78220682 | *DesulfoVibrio desulfuricans* G20 |
| Ddes_0298 | YP_002478891.1 | 220903579 | *Desulfovibrio desulfuricans* subsp. *desulfuricans* str. ATCC 27774 |
| Por | YP_428946.1 | 83588937 | *Moorella thermoacetica* |
| YdbK | NP_415896.1 | 16129339 | *Escherichia coli* |
| nifJ (CT1628) | NP_662511.1 | 21674446 | *Chlorobium tepidum* |
| CJE1649 | YP_179630.1 | 57238499 | *Campylobacter jejuni* |
| nifJ | ADE85473.1 | 294476085 | *Rhodobacter capsulatus* |
| porE | BAA95603.1 | 7768912 | *Hydrogenobacter thermophilus* |
| porD | BAA95604.1 | 7768913 | *Hydrogenobacter thermophilus* |
| porA | BAA95605.1 | 7768914 | *Hydrogenobacter thermophilus* |
| porB | BAA95606.1 | 776891 | *Hydrogenobacter thermophilus* |
| porG | BAA95607.1 | 7768916 | *Hydrogenobacter thermophilus* |
| FqrB | YP_001482096.1 | 157414840 | *Campylobacter jejuni* |
| HP1164 | NP_207955.1 | 15645778 | *Helicobacter pylori* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoamide dehydrogenase (E3). This enzyme is naturally present in several organisms, including *E. coli* and *S. cerevisiae*. In the *E. coli* enzyme, specific residues in the E1 component are responsible for substrate specificity (Bisswanger, H., *J. Biol. Chem.* 256:815-82 (1981); Bremer, J., Eur. J. Biochem. 8:535-540 (1969); Gong et al., *J. Biol. Chem.* 275:13645-13653 (2000)). Enzyme engineering efforts have improved the *E. coli* PDH enzyme activity under anaerobic conditions (Kim et al., *J. Bacteriol.* 190: 3851-3858 (2008); Kim et al., *Appl. Environ. Microbiol.* 73:1766-1771 (2007); Zhou et al., *Biotechnol. Lett.* 30:335-342 (2008)). In contrast to the *E. coli* PDH, the *B. subtilis* complex is active and required for growth under anaerobic conditions (Nakano et al., *J. Bacteriol.* 179:6749-6755 (1997)). The *Klebsiella pneumoniae* PDH, characterized during growth on glycerol, is also active under anaerobic conditions (5). Crystal structures of the enzyme complex from bovine kidney (18) and the E2 catalytic domain from *Azotobacter vinelandii* are available (4). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in *Escherichia coli* encoded by pflB (Knappe and Sawers, FEMS. Microbiol Rev. 6:383-398 (1990)), *Lactococcus lactis* (Melchiorsen et al., Appl Microbiol Biotechnol 58:338-344 (2002)), and *Streptococcus mutans* (Takahashi-Abbe et al., Oral. Microbiol Immunol. 18:293-297 (2003)). *E. coli* possesses an additional pyruvate formate lyase, encoded by tdcE, that catalyzes the conversion of pyruvate or 2-oxobutanoate to acetyl-CoA or propionyl-CoA, respectively (Hesslinger et al., Mol. Microbiol 27:477-492 (1998)). Both pflB and tdcE from *E. coli* require the presence of pyruvate formate lyase activating enzyme, encoded by pflA. Further, a short protein encoded by yfiD in *E. coli* can associate with and restore activity to oxygen-cleaved pyruvate formate lyase (Vey et al., Proc. Natl. Acad. Sci. U.S.A. 105:16137-16141 (2008). Note that pflA and pflB from *E. coli* were expressed in *S. cerevisiae* as a means to increase cytosolic acetyl-CoA for butanol production as described in WO/2008/080124]. Additional pyruvate formate lyase and activating enzyme candidates, encoded by pfl and act, respectively, are found in *Clostridium pasteurianum* (Weidner et al., J Bacteriol. 178:2440-2444 (1996)).

Further, different enzymes can be used in combination to convert pyruvate into acetyl-CoA. For example, in *S. cerevisiae*, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including *E. coli* (Kumari et al., J. Bacteriol. 177:2878-2886 (1995)), *Salmonella enterica* (Starai et al., *Microbiology* 151:3793-3801 (2005); Starai et al., J. Biol. Chem. 280:26200-26205 (2005)), and *Moorella thermoacetica* (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetlyase are well-studied enzymes in several *Clostridia* and *Methanosarcina thermophile*.

Yet another way of converting pyruvate to acetyl-CoA is via pyruvate oxidase. Pyruvate oxidase converts pyruvate into acetate, using ubiquione as the electron acceptor. In *E. coli*, this activity is encoded by poxB. PoxB has similarity to pyruvate decarboxylase of *S. cerevisiae* and *Zymomonas mobilis*. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

For enzymes that use reducing equivalents in the form of NADH or NADPH, these reduced carriers can be generated by transferring electrons from reduced ferredoxin. Two enzymes catalyze the reversible transfer of electrons from reduced ferredoxins to $NAD(P)^+$, ferredoxin:$NAD^+$ oxidoreductase (EC 1.18.1.3) and ferredoxin:$NADP^+$ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., *Eur. J. Biochem.* 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St et al. 2007). A ferredoxin:NADP+ oxidoreductase enzyme is encoded in the *E. coli* genome by fpr (Bianchi et al. 1993). Ferredoxin:NAD+ oxidoreductase utilizes reduced ferredoxin to generate NADH from NAD+. In several organisms, including *E. coli*, this enzyme is a component of multifunctional dioxygenase enzyme complexes. The ferredoxin:NAD+ oxidoreductase of *E. coli*, encoded by hcaD, is a component of the 3-phenylproppionate dioxygenase system involved in involved in aromatic acid utilization (Diaz et al. 1998). NADH:ferredoxin reductase activity was detected in cell extracts of *Hydrogenobacter thermophilus* strain TK-6, although a gene with this activity has not yet been indicated (Yoon et al. 2006). Finally, the energy-conserving membrane-associated Rnf-type proteins (Seedorf et al., Proc. Natl. Acad. Sci. U.S.A. 105:2128-2133 (2008); Herrmann et al., J. Bacteriol. 190: 784-791 (2008)) provide a means to generate NADH or NADPH from reduced ferredoxin. Additional ferredoxin: NAD(P)+ oxidoreductases have been annotated in *Clostridium carboxydivorans* P7.

| Protein | GenBank ID | GI Number | Organism |
|---|---|---|---|
| HP1164 | NP_207955.1 | 15645778 | *Helicobacter pylori* |
| CJE0663 | AAW35824.1 | 57167045 | *Campylobacter jejuni* |
| fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |

Ferredoxins are small acidic proteins containing one or more iron-sulfur clusters that function as intracellular electron carriers with a low reduction potential. Reduced ferredoxins donate electrons to Fe-dependent enzymes such as ferredoxin-NADP+ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica*, *Clostridium carboxidivorans* P7 and *Rhodospirillum rubrum* are predicted to encode several ferredoxins, listed in the table below.

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| CcarbDRAFT_4383 | ZP_05394383.1 | 255527515 | *Clostridium carboxidivorans* P7 |
| CcarbDRAFT_2958 | ZP_05392958.1 | 255526034 | *Clostridium carboxidivorans* P7 |
| CcarbDRAFT_2281 | ZP_05392281.1 | 255525342 | *Clostridium carboxidivorans* P7 |
| CcarbDRAFT_5296 | ZP_05395295.1 | 255528511 | *Clostridium carboxidivorans* P7 |
| CcarbDRAFT_1615 | ZP_05391615.1 | 255524662 | *Clostridium carboxidivorans* P7 |
| CcarbDRAFT_1304 | ZP_05391304.1 | 255524347 | *Clostridium carboxidivorans* P7 |
| Rru_A2264 | ABC23064.1 | 83576513 | *Rhodospirillum rubrum* |
| Rru_A1916 | ABC22716.1 | 83576165 | *Rhodospirillum rubrum* |
| Rru_A2026 | ABC22826.1 | 83576275 | *Rhodospirillum rubrum* |

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of *Clostridium kluyveri* has been shown to exhibit succinyl-CoA: acetyl-CoA transferase activity (Sohling and Gottschalk, J. Bacteriol. 178:871-880 (1996)). In addition, the activity is present in *Trichomonas vaginalis* (van Grinsven et al. 2008) and *Trypanosoma brucei* (Riviere et al. 2004). The succinyl-CoA:acetate CoA-transferase from *Acetobacter aceti*, encoded by aarC, replaces succinyl-CoA synthetase in a variant TCA cycle (Mullins et al. 2008). Similar succinyl-CoA transferase activities are also present in *Trichomonas vaginalis* (van Grinsven et al. 2008), *Try-* panosoma brucei (Riviere et al. 2004) and *Clostridium kluyveri* (Sohling and Gottschalk, 1996c). The beta-ketoadipate:succinyl-CoA transferase encoded by pcaI and pcaJ in *Pseudomonas putida* is yet another candidate (Kaschabek et al. 2002). The aforementioned proteins are identified below.

| Protein | GenBank ID | GI Number | Organism |
| --- | --- | --- | --- |
| cat1 | P38946.1 | 729048 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| pcaI | AAN69545.1 | 24985644 | *Pseudomonas putida* |
| pcaJ | NP_746082.1 | 26990657 | *Pseudomonas putida* |
| aarC | ACD85596.1 | 189233555 | *Acetobacter aceti* |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in *Helicobacter pylori* (Corthesy-Theulaz et al. 1997), *Bacillus subtilis*, and *Homo sapiens* (Fukao et al. 2000; Tanaka et al. 2002). The aforementioned proteins are identified below.

| Protein | GenBank ID | GI Number | Organism |
| --- | --- | --- | --- |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Converting succinate to succinyl-CoA by succinyl-CoA: 3:ketoacid-CoA transferase requires the simultaneous conversion of a 3-ketoacyl-CoA such as acetoacetyl-CoA to a 3-ketoacid such as acetoacetate. Conversion of a 3-ketoacid back to a 3-ketoacyl-CoA can be catalyzed by an acetoacetyl-CoA: acetate: CoA transferase. Acetoacetyl-CoA: acetate: CoA transferase converts acetoacetyl-CoA and acetate to acetoacetate and acetyl-CoA, or vice versa. Exemplary enzymes include the gene products of atoAD from *E. coli* (Hanai et al., Appl Environ Microbiol 73:7814-7818 (2007), ctfAB from *C. acetobutylicum* (Jojima et al., Appl Microbiol Biotechnol 77:1219-1224 (2008), and ctfAB from *Clostridium saccharoperbutylacetonicum* (Kosaka et al., Biosci. Biotechnol Biochem. 71:58-68 (2007)) are shown below.

| Protein | GenBank ID | GI Number | Organism |
| --- | --- | --- | --- |
| AtoA | NP_416726.1 | 2492994 | *Escherichia coli* |
| AtoD | NP_416725.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatics* (Leutwein and Heider, *J. Bact.* 183(14) 4288-4295 (2001)). Homologs can be found in *Azoarcus* sp. T, *Aromatoleum aromaticum* EbN1, and *Geobacter metallireducens* GS-15. The aforementioned proteins are identified below.

| Protein | GenBank ID | GI Number | Organism |
| --- | --- | --- | --- |
| bbsE | AAF89840 | 9622535 | *Thauera aromatic* |
| Bbsf | AAF89841 | 9622536 | *Thauera aromatic* |
| bbsE | AAU45405.1 | 52421824 | *Azoarcus* sp. T |
| bbsF | AAU45406.1 | 52421825 | *Azoarcus* sp. T |
| bbsE | YP_158075.1 | 56476486 | *Aromatoleum aromaticum* EbN1 |
| bbsF | YP_158074.1 | 56476485 | *Aromatoleum aromaticum* EbN1 |
| Gmet_1521 | YP_384480.1 | 78222733 | *Geobacter metallireducens* GS-15 |
| Gmet_1522 | YP_384481.1 | 78222734 | *Geobacter metallireducens* GS-15 |

Additionally, ygfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. The aforementioned proteins are identified below.

| Protein | GenBank ID | GI Number | Organism |
| --- | --- | --- | --- |
| ygfH | NP_417395.1 | 16130821 | *Escherichia coli* str. K-12 substr. MG1655 |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae serovar* |
| yinte0001_14430 | ZP_04635364.1 | 238791727 | *Yersinia intermedia* ATCC 29909 |

Finally, although specific gene sequences were not provided for butyryl-CoA:acetoacetate CoA-transferase in these references, the genes FNO272 and FNO273 have been annotated as a butyrate-acetoacetate CoA-transferase (Kapatral et al., *J. Bacteriol.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional genes from *Porphyrmonas gingivalis* and *Thermoanaerobacter tengcongensis* can be identified in a similar fashion (Kreimeyer, et al., *J. Biol. Chem.* 282 (10) 7191-7197 (2007)). The aforementioned proteins are identified below.

| Protein | GenBank ID | GI Number | Organism |
| --- | --- | --- | --- |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Citrate lyase (EC 4.1.3.6) catalyzes a series of reactions resulting in the cleavage of citrate to acetate and oxaloacetate. The enzyme is active under anaerobic conditions and is composed of three subunits: an acyl-carrier protein (ACP, gamma), an ACP transferase (alpha), and a acyl lyase (beta). Enzyme activation uses covalent binding and acetylation of an unusual prosthetic group, 2'-(5"-phosphoribosyl)-3-'-dephospho-CoA, which is similar in structure to acetyl-CoA. Acylation is catalyzed by CitC, a citrate lyase synthetase.

Two additional proteins, CitG and CitX, are used to convert the apo enzyme into the active holo enzyme (Schneider et al., *Biochemistry* 39:9438-9450 (2000)). Wild type *E. coli* does not have citrate lyase activity; however, mutants deficient in molybdenum cofactor synthesis have an active citrate lyase (Clark, *FEMS Microbiol. Lett.* 55:245-249 (1990)). The *E. coli* enzyme is encoded by citEFD and the citrate lyase synthetase is encoded by citC (Nilekani and SivaRaman, *Biochemistry* 22:4657-4663 (1983)). The *Leuconostoc mesenteroides* citrate lyase has been cloned, characterized and expressed in *E. coli* (Bekal et al., *J. Bacteriol.* 180:647-654 (1998)). Citrate lyase enzymes have also been identified in enterobacteria that utilize citrate as a carbon and energy source, including *Salmonella typhimurium* and *Klebsiella pneumoniae* (Bott, *Arch. Microbiol.* 167: 78-88 (1997); Bott and Dimroth, *Mol. Microbiol.* 14:347-356 (1994)). The aforementioned proteins are tabulated below.

| Protein | GenBank ID | GI Number | Organism |
|---|---|---|---|
| citF | AAC73716.1 | 1786832 | *Escherichia coli* |
| citE | AAC73717.2 | 87081764 | *Escherichia coli* |
| citD | AAC73718.1 | 1786834 | *Escherichia coli* |
| citC | AAC73719.2 | 87081765 | *Escherichia coli* |
| citG | AAC73714.1 | 1786830 | |
| citX | AAC73715.1 | 1786831 | |
| citF | CAA71633.1 | 2842397 | *Leuconostoc mesenteroides* |
| citE | CAA71632.1 | 2842396 | *Leuconostoc mesenteroides* |
| citD | CAA71635.1 | 2842395 | *Leuconostoc mesenteroides* |
| citC | CAA71636.1 | 3413797 | *Leuconostoc mesenteroides* |
| citG | CAA71634.1 | 2842398 | *Leuconostoc mesenteroides* |
| citX | CAA71634.1 | 2842398 | *Leuconostoc mesenteroides* |
| citF | NP_459613.1 | 16763998 | *Salmonella typhimurium* |
| citE | AAL19573.1 | 16419133 | *Salmonella typhimurium* |
| citD | NP_459064.1 | 16763449 | *Salmonella typhimurium* |
| citC | NP_459616.1 | 16764001 | *Salmonella typhimurium* |
| citG | NP_459611.1 | 16763996 | *Salmonella typhimurium* |
| citX | NP_459612.1 | 16763997 | *Salmonella typhimurium* |
| citF | CAA56217.1 | 565619 | *Klebsiella pneumoniae* |
| citE | CAA56216.1 | 565618 | *Klebsiella pneumoniae* |
| citD | CAA56215.1 | 565617 | *Klebsiella pneumoniae* |
| citC | BAH66541.1 | 238774045 | *Klebsiella pneumoniae* |
| citG | CAA56218.1 | 565620 | *Klebsiella pneumoniae* |
| citX | AAL60463.1 | 18140907 | *Klebsiella pneumoniae* |

Acetate kinase (EC 2.7.2.1) catalyzes the reversible ATP-dependent phosphorylation of acetate to acetylphosphate. Exemplary acetate kinase enzymes have been characterized in many organisms including *E. coli, Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbiology* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)).

| Protein | GenBank ID | GI Number | Organism |
|---|---|---|---|
| ackA | NP_416799.1 | 16130231 | *Escherichia coli* |
| Ack | AAB18301.1 | 1491790 | *Clostridium acetobutylicum* |
| Ack | AAA72042.1 | 349834 | *Methanosarcina thermophila* |
| purT | AAC74919.1 | 1788155 | *Escherichia coli* |
| buk1 | NP_349675 | 15896326 | *Clostridium acetobutylicum* |
| buk2 | Q97II1 | 20137415 | *Clostridium acetobutylicum* |

The formation of acetyl-CoA from acetylphosphate is catalyzed by phosphotransacetylase (EC 2.3.1.8). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction is also catalyzed by some phosphotranbutyrylase enzymes (EC 2.3.1.19) including the ptb gene products from *Clostridium acetobutylicum* (Wiesenborn et al., *App. Environ. Microbiol.* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001).

| Protein | GenBank ID | GI Number | Organism |
|---|---|---|---|
| Pta | NP_416800.1 | 71152910 | *Escherichia coli* |
| Pta | P39646 | 730415 | *Bacillus subtilis* |
| Pta | A5N801 | 146346896 | *Clostridium kluyveri* |
| Pta | Q9X0L4 | 6685776 | *Thermotoga maritima* |
| Ptb | NP_349676 | 34540484 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, *J. Bacteriol.* 184:636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida*

(Fernandez-Valverde et al., *Appl. Environ. Microbiol.* 59:1149-1154 (1993)). The aforementioned proteins are tabulated below.

| Protein | GenBank ID | GI Number | Organism |
|---|---|---|---|
| acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |

Formate dehydrogenase is a two subunit selenocysteine-containing protein that catalyzes the incorporation of $CO_2$ into formate in *Moorella thermoacetica* (Andreesen and Ljungdahl, *J. Bacteriol.* 116:867-873 (1973); Li et al., *J. Bacteriol.* 92:4-50412 (1966); Yamamoto et al., *J. Biol. Chem.* 258:1826-1832 (1983)). The loci, Moth_2312 and Moth_2313 are actually one gene that is responsible for encoding the alpha subunit of formate dehydrogenase while the beta subunit is encoded by Moth_2314 (Pierce et al., *Environ. Microbiol.* 10:2550-2573 (2008)). Another set of genes encoding formate dehydrogenase activity with a propensity for $CO_2$ reduction is encoded by Sfum_2703 through Sfum_2706 in *Syntrophobacter fumaroxidans* (Reda et al., *Proc. Natl. Acad. Sci. U.S.A.* 105:10654-10658 (2008); de Bok et al., *Eur. J. Biochem.* 270:2476-2485 (2003). Similar to their *M. thermoacetica* counterparts, Sfum_2705 and Sfum_2706 are actually one gene. A similar set of genes that have been indicated to carry out the same function are encoded by CHY_0731, CHY_0732, and CHY_0733 in *C. hydrogenoformans* (Wu et al., *PLoS Genet.* 1:e65 (2005)). Homologs are also found in *C. carboxidivorans* P7.

| Protein | GenBank ID | GI Number | Organism |
|---|---|---|---|
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |

Formyltetrahydrofolate synthetase ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); Whitehead and Rabinowitz, *J. Bacteriol.* 170:3255-3261 (1988), and CHY_2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
|---|---|---|---|
| Moth_0109 | YP_428991.1 | 83588982 | *Moorella thermoacetica* |
| CHY_2385 | YP_361182.1 | 78045024 | *Carboxydothermus hydrogenoformans* |
| FHS | P13419.1 | 120562 | *Clostridium acidurici* |
| CcarbDRAFT_1913 | ZP_05391913.1 | 255524966 | *Clostridium carboxidivorans* P7 |
| CcarbDRAFT_2946 | ZP_05392946.1 | 255526022 | *Clostridium carboxidivorans* P7 |
| Dhaf_0555 | ACL18622.1 | 219536883 | *Desulfitobacterium hafniense* |
| fhs | YP_001393842.1 | 153953077 | *Clostridium kluyveri* DSM 555 |
| fhs | YP_003781893.1 | 300856909 | *Clostridium ljungdahlii* DSM 13528 |

In *M. thermoacetica*, *E. coli*, and *C. hydrogenoformans*, methenyltetrahydrofolate cyclohydrolase and methylenetetrahydrofolate dehydrogenase are carried out by the bifunctional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
|---|---|---|---|
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |
| folD | ADK16789.1 | 300437022 | *Clostridium ljungdahlii* DSM 13528 |
| folD-2 | NP_951919.1 | 39995968 | *Geobacter sulfurreducens* PCA |
| folD | YP_725874.1 | 113867385 | *Ralstonia eutropha* H16 |
| folD | NP_348702.1 | 15895353 | *Clostridium acetobutylicum* ATCC 824 |
| folD | YP_696506.1 | 110800457 | *Clostridium perfringens* |

The final step of the methyl branch of the Wood-Ljungdahl pathway is catalyzed by methylenetetrahydrofolate reductase. In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below.

| Protein | GenBank ID | GI number | Organism |
|---|---|---|---|
| Moth_1191 | YP_430048.1 | 83590039 | Moorella thermoacetica |
| metF | NP_418376.1 | 16131779 | Escherichia coli |
| CHY_1233 | YP_360071.1 | 78044792 | Carboxydothermus hydrogenoformans |
| CLJU_c37610 | YP_003781889.1 | 300856905 | Clostridium ljungdahlii DSM 13528 |
| DesfrDRAFT_3717 | ZP_07335241.1 | 303248996 | Desulfovibrio fructosovorans JJ |
| CcarbDRAFT_2950 | ZP_05392950.1 | 255526026 | Clostridium carboxidivorans P7 |
| Ccel74_010100023124 | ZP_07633513.1 | 307691067 | Clostridium cellulovorans 743B |
| Cphy_3110 | YP_001560205.1 | 160881237 | Clostridium phytofermentans ISDg |

ACS/CODH is the central enzyme of the carbonyl branch of the Wood-Ljungdahl pathway. It catalyzes the reversible reduction of carbon dioxide to carbon monoxide and also the synthesis of acetyl-CoA from carbon monoxide, Coenzyme A, and the methyl group from a methylated corrinoid-iron-sulfur protein. The corrinoid-iron-sulfur-protein is methylated by methyltetrahydrofolate via a methyltransferase. Expression of ACS/CODH in a foreign host entails introducing one or more of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes used for carbon-monoxide dehydrogenase/ acetyl-CoA synthase activity typically reside in a limited region of the native genome that can be an extended operon (Ragsdale, S. W., Crit. Rev. Biochem. Mol. Biol. 39:165-195 (2004); Morton et al., J. Biol. Chem. 266:23824-23828 (1991); Roberts et al., Proc. Natl. Acad. Sci. U.S.A. 86:32-36 (1989). Each of the genes in this operon from the acetogen, M. thermoacetica, has already been cloned and expressed actively in E. coli (Morton et al. supra; Roberts et al. supra; Lu et al., J. Biol. Chem. 268:5605-5614 (1993). The protein sequences of these genes can be identified by the following GenBank accession numbers.

| Protein | GenBank ID | GI number | Organism |
|---|---|---|---|
| AcsE | YP_430054 | 83590045 | Moorella thermoacetica |
| AcsD | YP_430055 | 83590046 | Moorella thermoacetica |
| AcsF | YP_430056 | 83590047 | Moorella thermoacetica |
| Orf7 | YP_430057 | 83590048 | Moorella thermoacetica |
| AcsC | YP_430058 | 83590049 | Moorella thermoacetica |
| AcsB | YP_430059 | 83590050 | Moorella thermoacetica |
| AcsA | YP_430060 | 83590051 | Moorella thermoacetica |
| CooC | YP_430061 | 83590052 | Moorella thermoacetica |

The hydrogenic bacterium, Carboxydothermus hydrogenoformans, can utilize carbon monoxide as a growth substrate by means of acetyl-CoA synthase (Wu et al., PLoS Genet. 1:e65 (2005)). In strain Z-2901, the acetyl-CoA synthase enzyme complex lacks carbon monoxide dehydrogenase due to a frameshift mutation (Wu et al. supra (2005)), whereas in strain DSM 6008, a functional unframeshifted full-length version of this protein has been purified (Svetlitchnyi et al., Proc. Natl. Acad. Sci. U.S.A. 101:446-451 (2004)). The protein sequences of the C. hydrogenoformans genes from strain Z-2901 can be identified by the following GenBank accession numbers.

| Protein | GenBank ID | GI number | Organism |
|---|---|---|---|
| AcsE | YP_360065 | 78044202 | Carboxydothermus hydrogenoformans |
| AcsD | YP_360064 | 78042962 | Carboxydothermus hydrogenoformans |
| AcsF | YP_360063 | 78044060 | Carboxydothermus hydrogenoformans |
| Orf7 | YP_360062 | 78044449 | Carboxydothermus hydrogenoformans |
| AcsC | YP_360061 | 78043584 | Carboxydothermus hydrogenoformans |
| AcsB | YP_360060 | 78042742 | Carboxydothermus hydrogenoformans |
| CooC | YP_360059 | 78044249 | Carboxydothermus hydrogenoformans |

Homologous ACS/CODH genes can also be found in the draft genome assembly of Clostridium carboxidivorans P7.

| Protein | GenBank ID | GI Number | Organism |
|---|---|---|---|
| AcsA | ZP_05392944.1 | 255526020 | Clostridium carboxidivorans P7 |
| CooC | ZP_05392945.1 | 255526021 | Clostridium carboxidivorans P7 |
| AcsF | ZP_05392952.1 | 255526028 | Clostridium carboxidivorans P7 |
| AcsD | ZP_05392953.1 | 255526029 | Clostridium carboxidivorans P7 |
| AcsC | ZP_05392954.1 | 255526030 | Clostridium carboxidivorans P7 |
| AcsE | ZP_05392955.1 | 255526031 | Clostridium carboxidivorans P7 |
| AcsB | ZP_05392956.1 | 255526032 | Clostridium carboxidivorans P7 |
| Orf7 | ZP_05392958.1 | 255526034 | Clostridium carboxidivorans P7 |

The methanogenic archaeon, Methanosarcina acetivorans, can also grow on carbon monoxide, exhibits acetyl-CoA synthase/carbon monoxide dehydrogenase activity, and produces both acetate and formate (Lessner et al., Proc. Natl. Acad. Sci. U.S.A. 103:17921-17926 (2006)). This organism contains two sets of genes that encode ACS/CODH activity (Rother and Metcalf, Proc. Natl. Acad. Sci. U.S.A. 101:16929-16934 (2004)). The protein sequences of both sets of M. acetivorans genes are identified by the following GenBank accession numbers.

| Protein | GenBank ID | GI number | Organism |
|---|---|---|---|
| AcsC | NP_618736 | 20092661 | Methanosarcina acetivorans |
| AcsD | NP_618735 | 20092660 | Methanosarcina acetivorans |
| AcsF, CooC | NP_618734 | 20092659 | Methanosarcina acetivorans |
| AcsB | NP_618733 | 20092658 | Methanosarcina acetivorans |
| AcsEps | NP_618732 | 20092657 | Methanosarcina acetivorans |
| AcsA | NP_618731 | 20092656 | Methanosarcina acetivorans |
| AcsC | NP_615961 | 20089886 | Methanosarcina acetivorans |
| AcsD | NP_615962 | 20089887 | Methanosarcina acetivorans |
| AcsF, CooC | NP_615963 | 20089888 | Methanosarcina acetivorans |
| AcsB | NP_615964 | 20089889 | Methanosarcina acetivorans |
| AcsEps | NP_615965 | 20089890 | Methanosarcina acetivorans |
| AcsA | NP_615966 | 20089891 | Methanosarcina acetivorans |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenogenic bacteria such as *C. hydrogenoformans*. Hypotheses for the existence of two active CODH/ACS operons in *M. acetivorans* include catalytic properties (i.e., $K_m$, $V_{max}$, $k_{cat}$) that favor carboxidotrophic or aceticlastic growth or differential gene regulation enabling various stimuli to induce CODH/ACS expression (Rother et al., *Arch. Microbiol.* 188:463-472 (2007)).

Expression of the modified Wood-Ljungdahl (i.e., methanol Wood-Ljungdahl pathway) in a foreign host (see FIG. 3B) requires introducing a set of methyltransferases to utilize the carbon and hydrogen provided by methanol and the carbon provided by CO and/or $CO_2$. A complex of 3-methyltransferase proteins, denoted MtaA, MtaB, and MtaC, perform the desired methanol methyltransferase activity (Sauer et al., *Eur. J. Biochem.* 243:670-677 (1997); Naidu and Ragsdale, *J. Bacteriol.* 183:3276-3281 (2001); Tallant and Krzycki, *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996); Ragsdale, S. W., *Crit. Rev. Biochem. Mol. Biol.* 39:165-195 (2004)).

MtaB is a zinc protein that catalyzes the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* (Das et al., *Proteins* 67:167-176 (2007). In general, the MtaB and MtaC genes are adjacent to one another on the chromosome as their activities are tightly interdependent. The protein sequences of various MtaB and MtaC encoding genes in *M. barkeri*, *M. acetivorans*, and *M. thermoaceticum* can be identified by their following GenBank accession numbers.

| Protein | GenBank ID | GI number | Organism |
|---|---|---|---|
| MtaB1 | YP_304299 | 73668284 | *Methanosarcina barkeri* |
| MtaC1 | YP_304298 | 73668283 | *Methanosarcina barkeri* |
| MtaB2 | YP_307082 | 73671067 | *Methanosarcina barkeri* |
| MtaC2 | YP_307081 | 73671066 | *Methanosarcina barkeri* |
| MtaB3 | YP_304612 | 73668597 | *Methanosarcina barkeri* |
| MtaC3 | YP_304611 | 73668596 | *Methanosarcina barkeri* |
| MtaB1 | NP_615421 | 20089346 | *Methanosarcina acetivorans* |
| MtaB1 | NP_615422 | 20089347 | *Methanosarcina acetivorans* |
| MtaB2 | NP_619254 | 20093179 | *Methanosarcina acetivorans* |
| MtaC2 | NP_619253 | 20093178 | *Methanosarcina acetivorans* |
| MtaB3 | NP_616549 | 20090474 | *Methanosarcina acetivorans* |
| MtaC3 | NP_616550 | 20090475 | *Methanosarcina acetivorans* |
| MtaB | YP_430066 | 83590057 | *Moorella thermoacetica* |
| MtaC | YP_430065 | 83590056 | *Moorella thermoacetica* |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. U.S.A.* 103:18917-18922 (2006)). The MtaB genes, YP_307082 and YP_304612, in *M. barkeri* were identified by sequence homology to YP_304299. In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. The MtaC genes, YP_307081 and YP_304611, were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F. Struct. Biol. Cyrst. Commun.* 61:537-540 (2005) and further characterized by Northern hybridization and Western Blotting ((Das et al., *Proteins* 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | GI number | Organism |
|---|---|---|---|
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). It is also important to note that there are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$-MtaC to Coenzyme M, an *M. thermoacetica* MtaA is likely to transfer the methyl group to methyltetrahydrofolate given the similar roles of methyltetrahydrofolate and Coenzyme M in methanogens and acetogens, respectively. The protein sequences of putative MtaA encoding genes from *M. thermoacetica* can be identified by the following GenBank accession numbers.

| Protein | GenBank ID | GI number | Organism |
|---------|------------|-----------|----------|
| MtaA | YP_430937 | 83590928 | *Moorella thermoacetica* |
| MtaA | YP_431175 | 83591166 | *Moorella thermoacetica* |
| MtaA | YP_430935 | 83590926 | *Moorella thermoacetica* |

Anaerobic growth on synthesis gas and methanol in the absence of an external electron acceptor is conferred upon the host organism with MTR and ACS/CODH activity by enabling pyruvate synthesis via pyruvate ferredoxin oxidoreductase (PFOR). The gene candidates for PFOR and other methods for converting pyruvate to acetyl-CoA are described herein elsewhere.

The product yields per C-mol of substrate of microbial cells synthesizing reduced fermentation products such as ethanol, butanol, isobutanol, 2-butanol, isopropanol, 1,4-butanediol, succinic acid, fumaric acid, malic acid, 4-hydroxybutyric acid, adipic acid, 6-aminocaproic acid, hexamethylenediamine, caprolactam, 3-hydroxyisobutyric acid, 2-hydroxyisobutyric acid, methacrylic acid, acrylic acid, 1,3-propanediol, glycerol, etc., are limited by insufficient reducing equivalents in the carbohydrate feedstock. Reducing equivalents, or electrons, can be extracted from synthesis gas components such as CO and $H_2$ using carbon monoxide dehydrogenase (CODH) and hydrogenase enzymes, respectively. The reducing equivalents are then passed to acceptors such as oxidized ferredoxins, oxidized quinones, oxidized cytochromes, NADP+, water, or hydrogen peroxide to form reduced ferredoxin, reduced quinones, reduced cytochromes, NAD(P)H, $H_2$, or water, respectively. Reduced ferredoxin and NAD(P)H are particularly useful as they can serve as redox carriers for various Wood-Ljungdahl pathway and reductive TCA cycle enzymes.

Here, we show specific examples of how additional redox availability from CO and/or $H_2$ can improve the yields of reduced products such as 1,4-BDO, 1,3-BDO, butanol, 6-aminocaproic acid, hexamethylene diamine, caprolactam, glycerol and 1,3-propanediol.

Figure 1A:
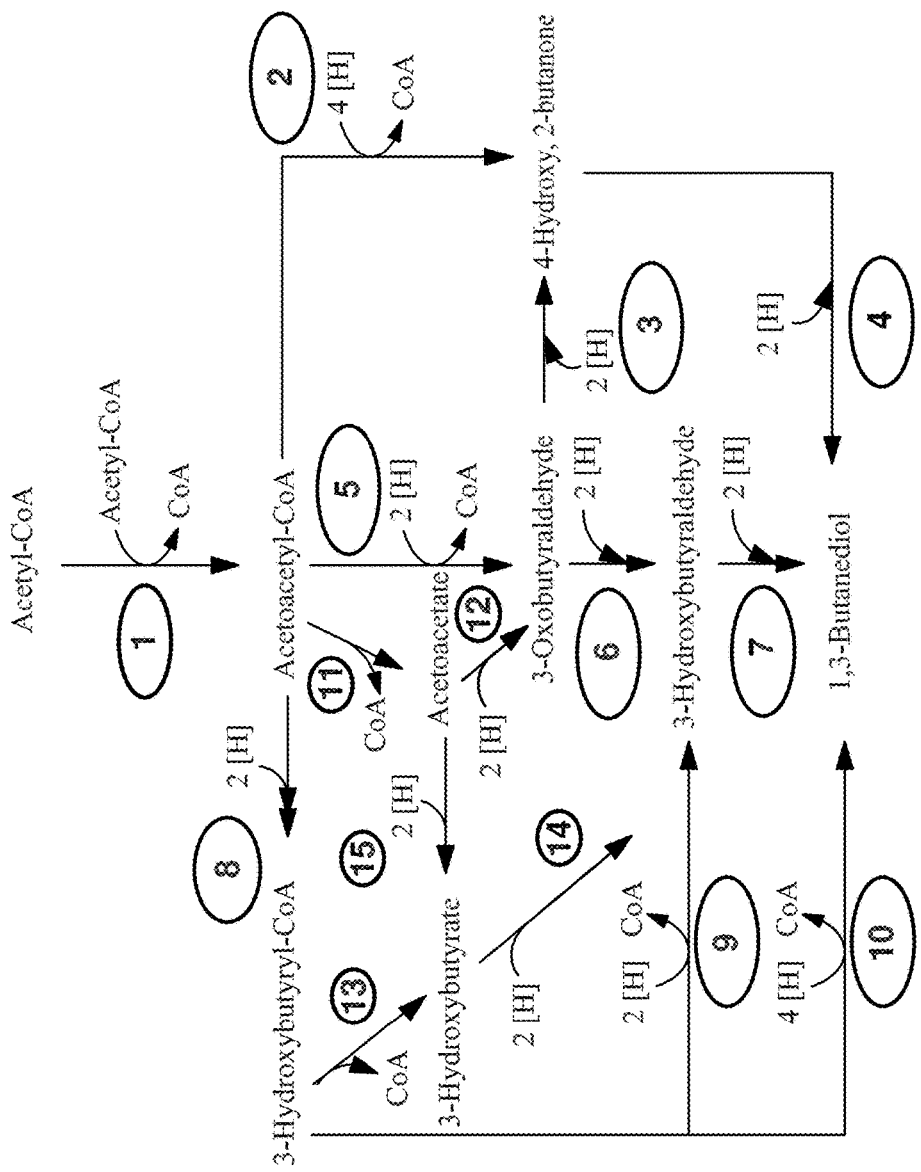
FIG. 1a shows the pathways for the biosynthesis of 1,3-butanediol from acetyl-CoA; the enzymatic transformations shown are carried out by the following enzymes: 1) Acetoacetyl-CoA thiolase (AtoB), 2) Acetoacetyl-CoA reductase (CoA-dependent, alcohol forming), 3) 3-oxobutyraldehyde reductase (aldehyde reducing), 4) 4-hydroxy, 2-butanone reductase, 5) Acetoacetyl-CoA reductase (CoA-dependent, aldehyde forming), 6) 3-oxobutyraldehyde reductase (ketone reducing), 7) 3-hydroxybutyraldehyde reductase, 8) Acetoacetyl-CoA reductase (ketone reducing), 9) 3-hydroxybutyryl-CoA reductase (aldehyde forming), 10) 3-hydroxybutyryl-CoA reductase (alcohol forming), 11) an acetoacetyl-CoA transferase, an acetoacetyl-CoA hydrolase, an acetoacetyl-CoA synthetase, or a phosphotransacetoacetylase/acetoacetate kinase, 12) Acetoacetate reductase, 13) 3-hydroxybutyryl-CoA transferase, hydrolase, or synthetase, 14) 3-hydroxybutyrate reductase, and 15) 3-hydroxybutyrate dehydrogenase.
Figure 1B:
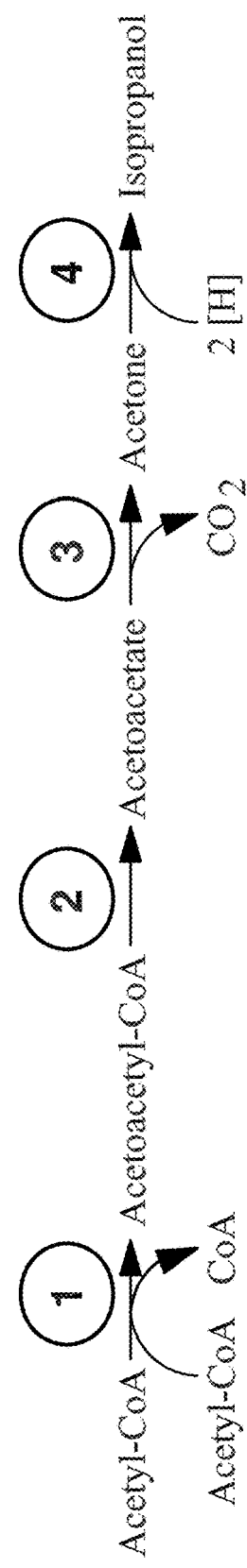
FIG. 1b shows the pathways for the biosynthesis of isopropanol from acetyl-CoA; the enzymatic transformations shown are carried out by the following enzymes: 1) Acetoacetyl-CoA thiolase (AtoB), 2) Acetoacetyl-CoA transferase, acetoacetyl-CoA hydrolase, acetoacetyl-CoA synthetase, or phosphotransacetoacetylase/acetoacetate kinase, 3) Acetoacetate decarboxylase (Adc), and 4) Isopropanol dehydrogenase (Adh)
Figure 1C:
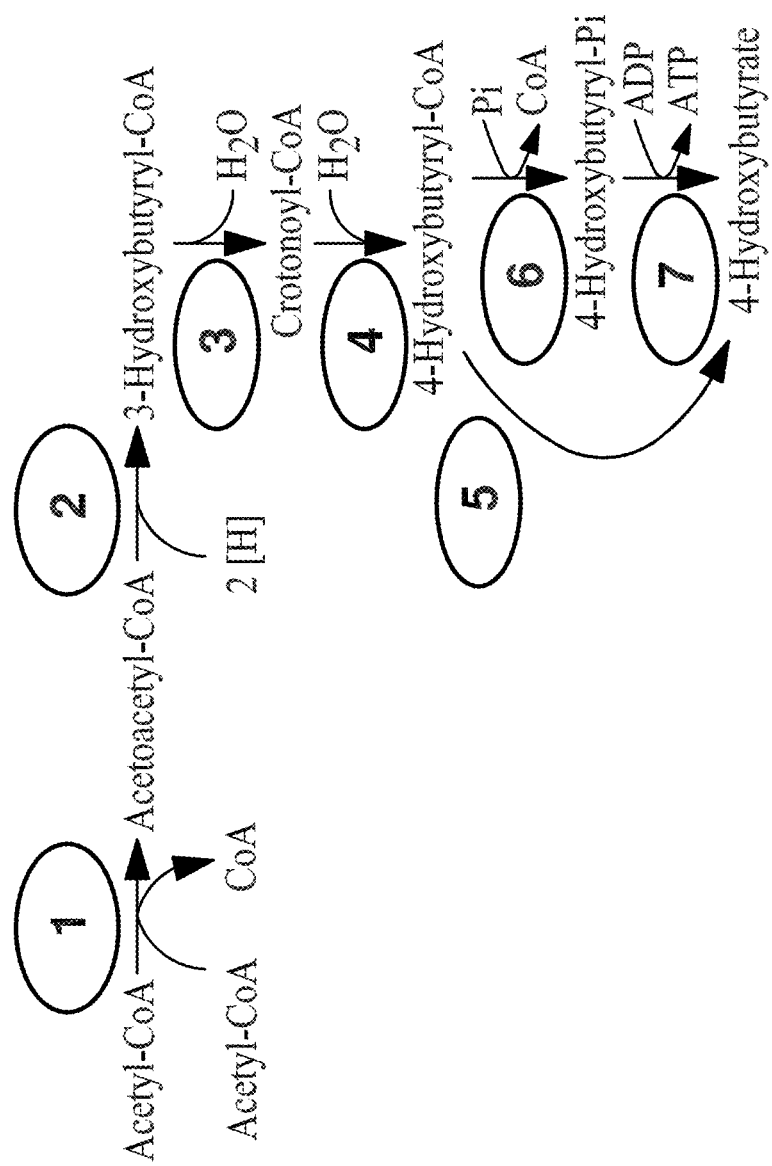
FIG. 1c shows the pathways for the biosynthesis of 4-hydroxybutyrate (4-HB); the enzymatic transformations shown are carried out by the following enzymes: 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-Hydroxybutyryl-CoA transferase, hydrolase or synthetase, 6) Phosphotrans-4-hydroxybutyrylase, and 7) 4-Hydroxybutyrate kinase.
Figure 1D:
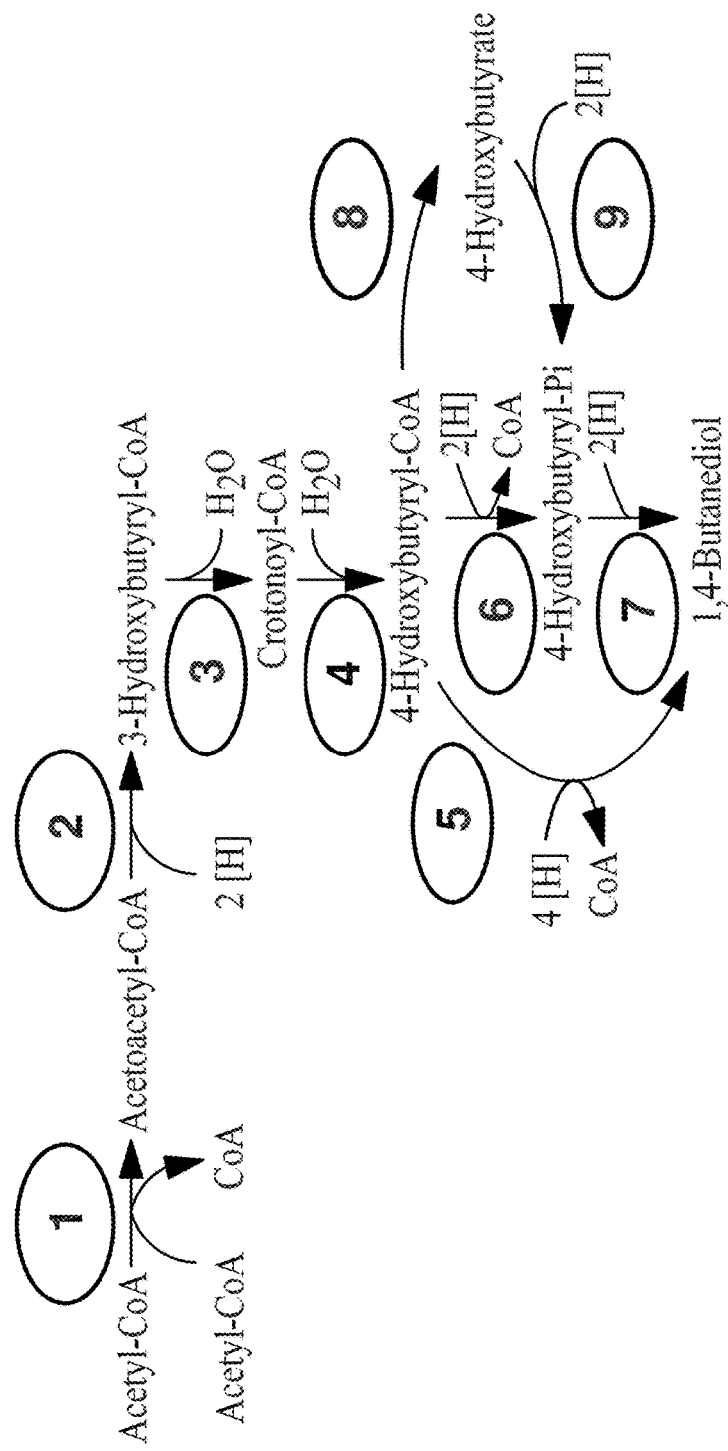
FIG. 1d shows the pathways for the biosynthesis of 1,4-butanediol; the enzymatic transformations shown are carried out by the following enzymes: 1) Acetoacetyl-CoA thiolase (AtoB), 2) 3-Hydroxybutyryl-CoA dehydrogenase (Hbd), 3) Crotonase (Crt), 4) Crotonyl-CoA hydratase (4-Budh), 5) 4-hydroxybutyryl-CoA reductase (alcohol forming), 6) 4-hydroxybutyryl-CoA reductase (aldehyde forming), 7) 1,4-butanediol dehydrogenase, 8) 4-Hydroxybutyryl-CoA transferase, 4-Hydroxybutyryl-CoA synthetase, 4-Hydroxybutyryl-CoA hydrolase, or Phosphotrans-4-hydroxybutyrylase/4-Hydroxybutyrate kinase, and 9) 4-Hydroxybutyrate reductase.

The maximum theoretical yield to produce 1,4-BDO from glucose is 1.0 mole 1,4-BDO per mole of glucose under aerobic conditions via the pathways shown in FIG. 1D:

$$1C_6H_{12}O_6 + \tfrac{1}{2}O_2 \rightarrow 1C_4H_{10}O_2 + 2CO_2 + 1H_2O$$

Or 1.09 mol 1,4-BDO per mol of glucose under anaerobic conditions:

$$1C_6H_{12}O_6 \rightarrow 1.09C_4H_{10}O_2 + 1.64CO_2 + 0.55H_2O$$

When both feedstocks of sugar and syngas are available, the syngas components CO and $H_2$ can be utilized to generate reducing equivalents by employing the hydrogenase and CO dehydrogenase. The reducing equivalents generated from syngas components will be utilized to power the glucose to BDO production pathways. Theoretically, all carbons in glucose will be conserved, thus resulting in a maximal theoretical yield to produce 1,4-BDO from glucose at 2 mol 1,4-BDO per mol of glucose under either aerobic or anaerobic conditions as shown in FIG. 7A:

$$1C_6H_{12}O_6 + 2CO + 8H_2 \rightarrow 2C_4H_{10}O_2 + 4H_2O$$

In a similar manner, the maximum theoretical yield of 1,3-butanediol can be improved further to 2 mol/mol glucose. An exemplary flux distribution with the improved yields is shown in FIG. 7B.

$$1C_6H_{12}O_6 + 2CO + 8H_2 \rightarrow 2C_4H_{10}O_2 + 4H_2O$$

Butanol is yet another example of a reduced product. The production of butanol through fermentation has a theoretical yield of 1 mol butanol per mol of glucose. It is currently manufactured from propylene and usually used close to the point of manufacture. Butanol is largely used as an industrial intermediate, particularly for the manufacture of butyl acrylate, butyl acetate, dibutyl phthalate, dibutyl sebacate and other butyl esters. Other industrial uses include the manufacture of pharmaceuticals, polymers, plastics, and herbicide. It can also be used as a solvent for the extraction of essential oils, antibiotics, hormones, and vitamins, or as a solvent for paints, coatings, natural resins, gums, synthetic resins, dyes, alkaloids, and camphor. Butanol has also been proposed as the next generation biofuel to substitute for diesel fuel and gasoline. It is also used in a wide range of consumer products.

$$1C_6H_{12}O_6 \rightarrow 1C_4H_{10}O + 2CO_2 + 1H_2O$$

When the combined feedstocks strategy is applied to butanol production, the reducing equivalents generated from syngas can increase the butanol theoretical yield from glucose to 2 mol butanol per mol of glucose with the pathways detailed in FIG. 7C.

$$1C_6H_{12}O_6 + 2CO + 10H_2 \rightarrow 2C_4H_{10}O + 6H_2O$$

Hexamethylenediamine (HMDA) can be used to produce nylon 6,6, a linear polyamide made by condensing hexamethylenediamine with adipic acid. This is employed for manufacturing different kinds of fibers. In addition to HMDA being used in the production of nylon-6,6, it is also utilized to make hexamethylene diisocyanate, a monomer feedstock used in the production of polyurethane. The diamine also serves as a cross-linking agent in epoxy resins. HMDA is presently produced by the hydrogenation of adiponitrile.

The production of HMDA through fermentation has a theoretical yield of 0.7059 mol HMDA per mol of glucose.

$$17C_6H_{12}O_6 + 24NH_3 \rightarrow 12C_6H_{16}N_2 + 30CO_2 + 42H_2O$$

When the combined feedstocks strategy is applied to the HMDA production, the reducing equivalents generated from syngas can increase the HMDA theoretical yield from glucose to 1 mol HMDA per mol of glucose with the pathways detailed in FIG. 7D.

$$1C_6H_{12}O_6 + 2NH_3 + 5H_2 \rightarrow 1C_6H_{16}N_2 + 6H_2O$$

or $$1C_6H_{12}O_6 + 2NH_3 + 5CO \rightarrow 1C_6H_{16}N_2 + H_2O + 5CO_2$$

or $$1C_6H_{12}O_6 + 2NH_3 + 2CO + 3H_2 \rightarrow 1C_6H_{16}N_2 + 4H_2O + 2CO_2$$

Caprolactam is an organic compound which is a lactam of 6-aminohexanoic acid (8-aminohexanoic acid, 6-aminocaproic acid). It can alternatively be considered a cyclic amide of caproic acid. One use of caprolactam is as a monomer in the production of nylon-6. Caprolactam can be synthesized from cyclohexanone via an oximation process using hydroxylammonium sulfate followed by catalytic rearrangement using the Beckmann rearrangement process step. The production of caprolactam through fermentation has a theoretical yield of 0.8 mol caprolactam per mol of glucose.

$$5C_6H_{12}O_6 + 4NH_3 \rightarrow 4C_6H_{13}NO_2 + 6CO_2 + 10H_2O$$

When the combined feedstocks strategy is applied to caprolactam production, the reducing equivalents generated from syngas can increase the caprolactam theoretical yield from glucose to 1 mol caprolactam per mol of glucose with the pathways detailed in FIG. 7D.

$1C_6H_{12}O_6+1NH_3+3H_2 \rightarrow 1C_6H_{13}NO_2+4H_2O$ or $1C_6H_{12}O_6+1NH_3+3CO \rightarrow 1C_6H_{13}NO_2+1H_2O+3CO_2$ or $1C_6H_{12}O_6+1NH_3+1CO+2H_2 \rightarrow 1C_6H_{13}NO_2+3H_2O+1CO_2$ Other exemplary products for which the yields on carbohydrates can be improved by providing additional reducing equivalents are 1,3-propanediol (1,3-PDO) and glycerol. 1,3-PDO is mainly used as a building block in the production of polymers. It can be formulated into a variety of industrial products including composites, adhesives, laminates, coatings, moldings, aliphatic polyesters, copolyesters. It is also a solvent and used as an antifreeze and wood paint.

1,3-PDO can be chemically synthesized via the hydration of acrolein or by the hydroformylation of ethylene oxide to afford 3-hydroxypropionaldehyde. The resultant aldehyde is hydrogenated to give 1,3-PDO. Additionally, 1,3-PDO can be produced biologically. The production of 1,3-PDO through fermentation has a theoretical yield of 1.5 mol 1,3-PDO per mol of glucose.

$2C_6H_{12}O_6 \rightarrow 3C_3H_8O_2+3CO_2$

When the combined feedstock strategy is applied to 1,3-PDO production, the reducing equivalents generated from syngas can increase the 1,3-PDO theoretical yield based on glucose to 2 mol 1,3-PDO per mol of glucose by the pathways shown in FIG. 7E.

$1C_6H_{12}O_6+4H_2 \rightarrow 2C_3H_8O_2+2H_2O$ or $1C_6H_{12}O_6+4CO+2H_2O \rightarrow 2C_3H_8O_2+4CO_2$ or $1C_6H_{12}O_6+2CO+2H_2 \rightarrow 2C_3H_8O_2+2CO_2$ Similarly, the production of glycerol through fermentation can be improved by the combined feedstock strategy. The production of glycerol through fermentation has a theoretical yield of 1.71 mol glycerol per mol of glucose.

$7C_6H_{12}O_6+6H_2O \rightarrow 12C_3H_8O_3+6CO_2$

When the combined feedstocks strategy is applied to glycerol production, the reducing equivalents generated from syngas can increase the glycerol theoretical yield from glucose to 2 mol glycerol per mol of glucose with the pathways detailed in FIG. 7E.

$1C_6H_{12}O_6+2H_2 \rightarrow 2C_3H_8O_3$ or $1C_6H_{12}O_6+2CO+2H_2O \rightarrow 2C_3H_8O_3+2CO_2$ or $1C_6H_{12}O_6+1CO+1H_2+1H_2O \rightarrow 2C_3H_8O_3+1CO_2$ As shown in above three examples, a combined feedstock strategy where syngas is combined with a sugar-based feedstock or other carbon substrate can greatly improve the theoretical yields. In this co-feeding approach, syngas components $H_2$ and CO can be utilized by the hydrogenase and CO dehydrogenase to generate reducing equivalents, that can be used to power chemical production pathways in which the carbons from sugar or other carbon substrates will be maximally conserved and the theoretical yields improved. In case of 1,4-BDO, 1,3-BDO and butanol productions from glucose or sugar, the theoretical yields improve from 1 mol or 1.09 mol products per mol of glucose to 2 mol products per mol of glucose. Such improvements provide environmental and economic benefits and greatly enhance sustainable chemical production.

Herein below the enzymes and the corresponding genes used for extracting redox from synags components are described. CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicotinamide adenine dinucleotide phosphate (NAD(P)H) carriers or ferredoxin-dependent cellular processes (Ragsdale, *Annals of the New York Academy of Sciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, and *Campylobacter curvus* 525.92.

| Protein | GenBank ID | GI Number | Organism |
| --- | --- | --- | --- |
| CODH (putative) | YP_430813 | 83590804 | *Moorella thermoacetica* |
| CODH-II (CooS-II) | YP_358957 | 78044574 | *Carboxydothermus hydrogenoformans* |
| CooF | YP_358958 | 78045112 | *Carboxydothermus hydrogenoformans* |

| Protein | GenBank ID | GI Number | Organism |
|---|---|---|---|
| CODH (putative) | ZP_05390164.1 | 255523193 | Clostridium carboxidivorans P7 |
| | ZP_05390341.1 | 255523371 | Clostridium carboxidivorans P7 |
| | ZP_05391756.1 | 255524806 | Clostridium carboxidivorans P7 |
| | ZP_05392944.1 | 255526020 | Clostridium carboxidivorans P7 |
| CODH | YP_384856.1 | 78223109 | Geobacter metallireducens GS-15 |
| Cpha266_0148 (cytochrome c) | YP_910642.1 | 119355998 | Chlorobium phaeobacteroides DSM 266 |
| Cpha266_0149 (CODH) | YP_910643.1 | 119355999 | Chlorobium phaeobacteroides DSM 266 |
| Ccel_0438 | YP_002504800.1 | 220927891 | Clostridium cellulolyticum H10 |
| Ddes_0382 (CODH) | YP_002478973.1 | 220903661 | Desulfovibrio desulfuricans subsp. desulfuricans str. ATCC 27774 |
| Ddes_0381 (CooC) | YP_002478972.1 | 220903660 | Desulfovibrio desulfuricans subsp. desulfuricans str. ATCC 27774 |
| Pcar_0057 (CODH) | YP_355490.1 | 7791767 | Pelobacter carbinolicus DSM 2380 |
| Pcar_0058 (CooC) | YP_355491.1 | 7791766 | Pelobacter carbinolicus DSM 2380 |
| Pcar_0058 (HypA) | YP_355492.1 | 7791765 | Pelobacter carbinolicus DSM 2380 |
| CooS (CODH) | YP_001407343.1 | 154175407 | Campylobacter curvus 525.92 |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)). The protein sequences of exemplary CODH and hydrogenase genes can be identified by the following GenBank accession numbers.

| Protein | GenBank ID | GI Number | Organism |
|---|---|---|---|
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |

Native to *E. coli* and other enteric bacteria are multiple genes encoding up to four hydrogenases (Sawers, G., *Antonie Van Leeuwenhoek* 66:57-88 (1994); Sawers et al., *J Bacteriol.* 164:1324-1331 (1985); Sawers and Boxer, *Eur. J Biochem.* 156:265-275 (1986); Sawers et al., *J Bacteriol.* 168:398-404 (1986)). Given the multiplicity of enzyme activities, *E. coli* or another host organism can provide sufficient hydrogenase activity to split incoming molecular hydrogen and reduce the corresponding acceptor. *E. coli* possesses two uptake hydrogenases, Hyd-1 and Hyd-2, encoded by the hyaABCDEF and hybOABCDEFG gene clusters, respectively (Lukey et al., How *E. coli* is equipped to oxidize hydrogen under different redox conditions, *J Biol Chem* published online Nov. 16, 2009). Hyd-1 is oxygen-tolerant, irreversible, and is coupled to quinone reduction via the hyaC cytochrome. Hyd-2 is sensitive to $O_2$, reversible, and transfers electrons to the periplasmic ferredoxin hybA which, in turn, reduces a quinone via the hybB integral membrane protein. Reduced quinones can serve as the source of electrons for fumarate reductase in the reductive branch of the TCA cycle. Reduced ferredoxins can be used by enzymes such as NAD(P)H:ferredoxin oxidoreductases to generate NADPH or NADH. They can alternatively be used as the electron donor for reactions such as pyruvate ferredoxin oxidoreductase, AKG ferredoxin oxidoreductase, and 5,10-methylene-H4folate reductase.

| Protein | GenBank ID | GI Number | Organism |
|---|---|---|---|
| HyaA | AAC74057.1 | 1787206 | Escherichia coli |
| HyaB | AAC74058.1 | 1787207 | Escherichia coli |
| HyaC | AAC74059.1 | 1787208 | Escherichia coli |
| HyaD | AAC74060.1 | 1787209 | Escherichia coli |
| HyaE | AAC74061.1 | 1787210 | Escherichia coli |

-continued

| Protein | GenBank ID | GI Number | Organism |
|---|---|---|---|
| HyaF | AAC74062.1 | 1787211 | Escherichia coli |
| HybO | AAC76033.1 | 1789371 | Escherichia coli |
| HybA | AAC76032.1 | 1789370 | Escherichia coli |
| HybB | AAC76031.1 | 2367183 | Escherichia coli |
| HybC | AAC76030.1 | 1789368 | Escherichia coli |
| HybD | AAC76029.1 | 1789367 | Escherichia coli |
| HybE | AAC76028.1 | 1789366 | Escherichia coli |
| HybF | AAC76027.1 | 1789365 | Escherichia coli |
| HybG | AAC76026.1 | 1789364 | Escherichia coli |

The hydrogen-lyase systems of E. coli include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase 3 has been shown to be a reversible enzyme (Maeda et al., Appl Microbiol Biotechnol 76(5):1035-42 (2007)). Hydrogenase activity in E. coli is also dependent upon the expression of the hyp genes whose corresponding proteins are involved in the assembly of the hydrogenase complexes (Jacobi et al., Arch. Microbiol 158:444-451 (1992); Rangarajan et al., J. Bacteriol, 190:1447-1458 (2008)).

| Protein | GenBank ID | GI Number | Organism |
|---|---|---|---|
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |

| Protein | GenBank ID | GI Number | Organism |
|---|---|---|---|
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |

The M. thermoacetica hydrogenases are suitable for a host that lacks sufficient endogenous hydrogenase activity. M. thermoacetica can grow with $CO_2$ as the exclusive carbon source indicating that reducing equivalents are extracted from $H_2$ to enable acetyl-CoA synthesis via the Wood-Ljungdahl pathway (Drake, H. L., J. Bacteriol. 150: 702-709 (1982); Drake and Daniel, Res. Microbiol. 155: 869-883 (2004); Kellum and Drake, J. Bacteriol. 160:466-469 (1984)) (see FIG. 2A). M. thermoacetica has homologs to several hyp, hyc, and hyf genes from E. coli. The protein sequences encoded for by these genes are identified by the following GenBank accession numbers.

Proteins in M. thermoacetica whose genes are homologous to the E. coli hyp genes are shown below.

| Protein | GenBank ID | GI Number | Organism |
|---|---|---|---|
| Moth_2175 | YP_431007 | 83590998 | Moorella thermoacetica |
| Moth_2176 | YP_431008 | 83590999 | Moorella thermoacetica |
| Moth_2177 | YP_431009 | 83591000 | Moorella thermoacetica |
| Moth_2178 | YP_431010 | 83591001 | Moorella thermoacetica |
| Moth_2179 | YP_431011 | 83591002 | Moorella thermoacetica |
| Moth_2180 | YP_431012 | 83591003 | Moorella thermoacetica |
| Moth_2181 | YP_431013 | 83591004 | Moorella thermoacetica |

Proteins in M. thermoacetica that are homologous to the E. coli Hydrogenase 3 and/or 4 proteins are listed in the following table.

| Protein | GenBank ID | GI Number | Organism |
|---|---|---|---|
| Moth_2182 | YP_431014 | 83591005 | Moorella thermoacetica |
| Moth_2183 | YP_431015 | 83591006 | Moorella thermoacetica |
| Moth_2184 | YP_431016 | 83591007 | Moorella thermoacetica |
| Moth_2185 | YP_431017 | 83591008 | Moorella thermoacetica |
| Moth_2186 | YP_431018 | 83591009 | Moorella thermoacetica |
| Moth_2187 | YP_431019 | 83591010 | Moorella thermoacetica |
| Moth_2188 | YP_431020 | 83591011 | Moorella thermoacetica |
| Moth_2189 | YP_431021 | 83591012 | Moorella thermoacetica |
| Moth_2190 | YP_431022 | 83591013 | Moorella thermoacetica |
| Moth_2191 | YP_431023 | 83591014 | Moorella thermoacetica |
| Moth_2192 | YP_431024 | 83591015 | Moorella thermoacetica |

In addition, several gene clusters encoding hydrogenase functionality are present in M. thermoacetica and their corresponding protein sequences are provided below.

| Protein | GenBank ID | GI Number | Organism |
|---|---|---|---|
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

Ralstonia eutropha H16 uses hydrogen as an energy source with oxygen as a terminal electron acceptor. Its membrane-bound uptake [NiFe]-hydrogenase is an "02-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, Biochim. Biophys. Acta, 567, 315-324 (1979); Bernhard et al., Eur. J. Biochem. 248, 179-186 (1997)). *R. eutropha* also contains an O$_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | GenBank ID | GI Number | Organism |
| --- | --- | --- | --- |
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |
| Hox1F | AAP50520.1 | 37787352 | *Thiocapsa roseopersicina* |
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

Several enzymes and the corresponding genes used for fixing carbon dioxide to either pyruvate or phosphoenolpyruvate to form the TCA cycle intermediates, oxaloacetate or malate are described below.

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
| --- | --- | --- | --- |
| Ppc | NP_418391 | 16131794 | *Escherichia coli* |
| ppcA | AAB58883 | 28572162 | *Methylobacterium extorquens* |
| Ppc | ABB53270 | 80973080 | *Corynebacterium glutamicum* |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCKJ, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high NaHCO$_3$ concentrations. Mutant strains of *E. coli* can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEP carboxykinase enzyme encoded by *Haemophilus influenza* is effective at forming oxaloacetate from PEP.

| Protein | GenBank ID | GI Number | Organism |
| --- | --- | --- | --- |
| PCK1 | NP_013023 | 6322950 | *Saccharomyces cerevisiae* |
| pck | NP_417862.1 | 16131280 | *Escherichia coli* |
| pckA | YP_089485.1 | 52426348 | *Mannheimia succiniciproducens* |
| pckA | O09460.1 | 3122621 | *Anaerobiospirillum succiniciproducens* |
| pckA | Q6W6X5 | 75440571 | *Actinobacillus succinogenes* |
| pckA | P43923.1 | 1172573 | *Haemophilus influenza* |

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
| --- | --- | --- | --- |
| PYC1 | NP_011453 | 6321376 | *Saccharomyces cerevisiae* |
| PYC2 | NP_009777 | 6319695 | *Saccharomyces cerevisiae* |
| Pyc | YP_890857.1 | 118470447 | *Mycobacterium smegmatis* |

Malic enzyme can be applied to convert CO$_2$ and pyruvate to malate at the expense of one reducing equivalent. Malic enzymes for this purpose can include, without limitation, malic enzyme (NAD-dependent) and malic enzyme (NADP-dependent). For example, one of the *E. coli* malic enzymes (Takeo, *J. Biochem.* 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in *E. coli* while restoring the lethal ΔpflΔldhA phenotype under anaerobic conditions by operating in the carbon-fixing direction (Stols and Donnelly, *Appl. Environ. Microbiol.* 63(7) 2695-2701 (1997)). A similar observation was made upon overexpressing the malic enzyme from *Ascaris suum* in *E. coli* (Stols et al., *Appl. Biochem. Biotechnol.* 63-65(1), 153-158 (1997)). The second *E. coli* malic enzyme, encoded by maeB, is NADP-dependent and also decarboxylates oxaloacetate and other alpha-keto acids (Iwakura et al., *J. Biochem.* 85(5):1355-65 (1979)).

| Protein | GenBank ID | GI Number | Organism |
|---|---|---|---|
| maeA | NP_415996 | 90111281 | *Escherichia coli* |
| maeB | NP_416958 | 16130388 | *Escherichia coli* |
| NAD-ME | P27443 | 126732 | *Ascaris suum* |

The enzymes used for converting oxaloacetate (formed from, for example, PEP carboxylase, PEP carboxykinase, or pyruvate carboxylase) or malate (formed from, for example, malic enzyme or malate dehydrogenase) to succinyl-CoA via the reductive branch of the TCA cycle are malate dehydrogenase, fumarate dehydratase (fumarase), fumarate reductase, and succinyl-CoA transferase. The genes for each of the enzymes are described herein above.

Enzymes, genes and methods for engineering pathways from succinyl-CoA to various products into a microorganism are now known in the art. The additional reducing equivalents obtained from CO and $H_2$, as disclosed herein, improve the yields of all these products when utilizing carbohydrate-based feedstock. For example, 1,4-butanediol can be produced from succinyl-CoA via previously disclosed pathways (see for example, Burk et al., WO 2008/115840). Exemplary enzymes for the conversion succinyl-CoA to 1,4-butanediol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA reductase (aldehyde forming), 1,4-butanediol dehydrogenase, succinyl-CoA reductase (alcohol forming), 4-hydroxybutyryl-CoA transferase, 4-hydroxybutyryl-CoA synthetase, 4-hydroxybutyryl-phosphate reductase, 4-hydroxybutyrate reductase, and 4-hydroxybutyryl-CoA reductase (alcohol forming). Succinate reductase can be additionally useful in converting succinate directly to the 1,4-butanediol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

1,3-butanediol can be produced from succinyl-CoA via the pathways have been described. Exemplary enzymes for the conversion succinyl-CoA to 1,3-butanediol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA dehydratase, crotonase, 3-hydroxybutyryl-CoA reductase (aldehyde forming), 3-hydroxybutyraldehyde reductase, succinyl-CoA reductase (alcohol forming), 4-hydroxybutyryl-CoA transferase, 4-hydroxybutyryl-CoA synthetase, 3-hydroxybutyryl-CoA hydrolase, 3-hydroxybutyryl-CoA synthetase, 3-hydroxybutyryl-CoA transferase, 3-hydroxybutyrate reductase, 3-hydroxybutyryl-CoA reductase (alcohol forming). Succinate reductase can be additionally useful by converting succinate directly to the 1,3-butanediol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

n-butanol can be produced from succinyl-CoA via known pathways. Exemplary enzymes for the conversion succinyl-CoA to butanol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA dehydratase, butyryl-CoA dehydrogenase, butyryl-CoA hydrolase, butyryl-coA synthetase, butyryl-coA transferase, butyrate reductase, butyryl-CoA reductase (aldehyde forming), butyraldehyde reductase, butyryl-CoA reductase (alcohol forming), succinyl-CoA reductase (alcohol forming), 4-hydroxybutyryl-CoA transferase, 4-hydroxybutyryl-CoA synthetase. Succinate reductase can be additionally useful by converting succinate directly to the butanol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

Isobutanol can be produced from succinyl-CoA via known pathways. Exemplary enzymes for the conversion succinyl-CoA to isobutanol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA dehydratase, butyryl-CoA dehydrogenase, isobutyryl-CoA mutase, isobutyryl-CoA hydrolase, isobutyryl-coA synthetase, isobutyryl-coA transferase, isobutyrate reductase, isobutyryl-CoA reductase (aldehyde forming), isobutyraldehyde reductase, isobutyryl-CoA reductase (alcohol forming), succinyl-CoA reductase (alcohol forming), 4-hydroxybutyryl-CoA transferase, 4-hydroxybutyryl-CoA synthetase. Succinate reductase can be additionally useful by converting succinate directly to the isobutanol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

Isopropanol can be produced from succinyl-CoA via known pathways. Exemplary enzymes for the conversion succinyl-CoA to isopropanol include succinyl-CoA reductase (aldehyde forming), 4-hydroxybutyrate dehydrogenase, 4-hydroxybutyrate kinase, phosphotrans-4-hydroxybutyrylase, 4-hydroxybutyryl-CoA dehydratase, crotonase, 3-hydroxybutyryl-CoA dehydrogenase, acetoacetyl-CoA synthetase, acetoacetate-CoA transferase, acetoacetyl-CoA hydrolase, acetoacetate decarboxylase, acetone reductase, succinyl-CoA reductase (alcohol forming), 4-hydroxybutyryl-CoA transferase, and 4-hydroxybutyryl-CoA synthetase. Succinate reductase can be additionally useful by converting succinate directly to the isopropanol pathway intermediate, succinate semialdehyde. Finally, succinyl-CoA can be converted by alpha-ketoglutarate:ferredoxin oxidoreductase to alpha-ketoglutarate whose decarboxylation by alpha-ketoglutarate decarboxylase leads to the formation of succinate semialdehyde.

n-propanol can be produced from succinyl-CoA via known pathways. Exemplary enzymes for the conversion succinyl-CoA to n-propanol include propionaldehyde dehydrogenase, propanol dehydrogenase, propionyl-CoA:phosphate propanoyltransferase, propionyl-CoA hydrolase, propionyl-CoA transferase, propionyl-CoA synthetase, propionate kinase, propionate reductase, propionyl phosphate reductase, methylmalonyl-CoA mutase, methylmalonyl-CoA epimerase, methylmalonyl-CoA decarboxylase, and methylmalonyl-CoA carboxytransferase.

Adipate can be produced from succinyl-CoA via known pathways (see for example, Burgard et al., (WO/2009/151728A2). Exemplary enzymes for the conversion of succinyl-CoA to adipate include succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, adipyl-CoA synthetase, phosphotransadipylase, adipate kinase, adipyl-CoA:acetyl-CoA transferase, adipyl-CoA hydrolase, 3-oxoadipyl-CoA transferase, 3-oxoadipate reductase, 3-hydroxyadipate dehydratase, and 2-enoate reductase.

6-aminocaproate can be produced from succinyl-CoA via known pathways. Exemplary enzymes for the conversion of succinyl-CoA to 6-aminocaproate include succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, adipyl-CoA synthetase, phosphotransadipylase, adipate kinase, adipyl-CoA:acetyl-CoA transferase, adipyl-CoA hydrolase, adipate reductase, adipyl-CoA reductase, CoA-dependent aldehyde dehydrogenase (e.g., adipyl-CoA reductase (aldehyde forming), transaminase (e.g., 6-aminocaproate transaminase), 6-aminocaproate dehydrogenase, 3-oxoadipyl-CoA transferase, 3-oxoadipate reductase, 3-hydroxyadipate dehydratase, and 2-enoate reductase.

Hexamethylenediamine can be produced from succinyl-CoA via known pathways. Exemplary enzymes for the conversion of succinyl-CoA to adipate include succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, adipyl-CoA synthetase, phosphotransadipylase, adipate kinase, adipyl-CoA:acetyl-CoA transferase, adipyl-CoA hydrolase, adipate reductase, adipyl-CoA reductase, CoA-dependent aldehyde dehydrogenase (e.g., adipyl-CoA reductase (aldehyde forming), transaminase (e.g., 6-aminocaproate transaminase), 6-aminocaproate dehydrogenase, 3-oxoadipyl-CoA transferase, 3-oxoadipate reductase, 3-hydroxyadipate dehydratase, 2-enoate reductase, 6-aminocaproyl-CoA/acyl-CoA transferase, 6-aminocaproyl-CoA synthase, 6-aminocaproyl-CoA reductase (aldehyde forming), hexamethylenediamine transaminase, and hexamethylenediamine dehydrogenase.

Enzymes, genes and methods for engineering pathways from glycolysis intermediates to various products into a microorganism are known in the art. The additional reducing equivalents obtained from CO and $H_2$, as described herein, improve the yields of all these products on carbohydrates. For example, glycerol and 1,3-propanediol can be produced from the glycolysis intermediate, dihydroxyacetone phosphate, via the pathways described in (Nakamura and Whited, Curr. Opin. Biotechnol. 14(5) 454-459 (2003)). Exemplary enzymes for the conversion of dihydroxyacetone phosphate to glycerol include glycerol-3-phosphate dehydrogenase and glycerol-3-phosphate phosphatase. Exemplary enzymes for the conversion of dihydroxyacetone phosphate to 1,3-propanediol include glycerol-3-phosphate dehydrogenase, glycerol-3-phosphate phosphatase, glycerol dehydratase, and 1,3-propanediol oxidoreductase.

In some embodiments, the reductive TCA cycle, coupled with carbon monoxide and hydrogenase enzymes, can be employed to allow syngas utilization by microorganisms. Synthesis gas (syngas) is a mixture of primarily $H_2$ and CO that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1$H_2$/CO mixture. In addition to coal, biomass of many types has been used for syngas production and represents an inexpensive and flexible feedstock for the biological production of renewable chemicals and fuels.

The $CO_2$-fixing reductive tricarboxylic acid (RTCA) cycle is an endergenic anabolic pathway of $CO_2$ assimilation, requiring reducing equivalents and ATP. The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophillic Knallgas bacteria) and sulfur-dependent archaea (Hugler et al., *J. Bacteriol.* 187:3020-3027 (2005; Hugler et al., *Environ. Microbiol.* 9:81-92 (2007). In some cases, reductive and oxidative (Krebs) TCA cycles are present in the same organism (Hugler et al., supra (2007); Siebers et al., *J. Bacteriol.* 186:2179-2194 (2004)). Some methanogens and obligate anaerobes possess incomplete oxidative or reductive TCA cycles that may function to synthesize biosynthetic intermediates (Ekiel et al., *J. Bacteriol.* 162:905-908 (1985); Wood et al., *FEMS Microbiol. Rev.* 28:335-352 (2004)).

The components of synthesis gas can provide sufficient $CO_2$, reducing equivalents, and ATP for the reductive TCA cycle to operate. One turn of the RTCA cycle assimilates two moles of $CO_2$ into one mole of acetyl-CoA and requires 2 ATP and 4 reducing equivalents. CO and $H_2$ can provide reducing equivalents by means of carbon monoxide dehydrogenase and hydrogenase enzymes, respectively. Reducing equivalents can come in the form of NADH, NADPH, FADH, reduced quinones, reduced ferredoxins, and reduced flavodoxins. The reducing equivalents, particularly NADH, NADPH, and reduced ferredoxin, can serve as cofactors for the RTCA cycle enzymes (e.g., malate dehydrogenase, fumarate reductase, alpha-ketoglutarate:ferredoxin oxidoreductase (alternatively known as 2-oxoglutarate:ferredoxin oxidoreductase, alpha-ketoglutarate synthase, or 2-oxoglutarate synthase), and isocitrate dehydrogenase). The electrons from these reducing equivalents can alternatively pass through an ion-gradient producing electron transport chain where they are passed to an acceptor such as oxygen, nitrate, oxidized metal ions, protons, or an electrode. The ion-gradient can then be used for ATP generation via an ATP synthase or similar enzyme.

Many of the enzymes in the TCA cycle are reversible and can catalyze reactions in the reductive and oxidative directions. However, some TCA cycle reactions are irreversible in vivo and thus different enzymes are used to catalyze these reactions in the directions required for the reverse TCA cycle. These reactions are: 1. conversion of citrate to oxaloacetate and acetyl-CoA, 2. conversion of fumarate to succinate, 3. conversion of succinyl-CoA to alpha-ketoglutarate. In the TCA cycle, citrate is formed from the condensation of oxaloacetate and acetyl-CoA. The reverse reaction, cleavage of citrate to oxaloacetate and acetyl-CoA, is ATP-dependent and catalyzed by ATP citrate lyase or citryl-CoA synthetase and citryl-CoA lyase. Alternatively, citrate lyase can be coupled to acetyl-CoA synthetase, an acetyl-CoA transferase, or phosphotransacetylase and acetate kinase to form acetyl-CoA and oxaloacetate from citrate. The conversion of succinate to fumarate is catalyzed by succinate dehydrogenase while the reverse reaction is catalyzed by fumarate reductase. In the TCA cycle succinyl-CoA is formed from the NAD(P)$^+$ dependent decarboxylation of oxaloacetate by the alpha-ketoglutarate dehydrogenase complex. The reverse reaction is catalyzed by alpha-ketoglutarate:ferredoxin oxidoreductase.

An organism capable of utilizing the reverse tricarboxylic acid cycle to enable production of acetyl-CoA-derived products on 1) CO, 2) $CO_2$ and $H_2$, 3) CO and $CO_2$, 4) synthesis gas comprising CO and $H_2$, and 5) synthesis gas comprising CO, $CO_2$, and $H_2$ can include any of the following enzyme activities: ATP-citrate lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, acetate kinase, phosphotransacetylase, acetyl-CoA synthetase, NAD(P)H:ferredoxin oxidoreductase, carbon monoxide dehydrogenase, hydrogenase, and ferredoxin (see FIG. 8). Enzyme enzymes and the corresponding genes required for these activities are described herein above.

Carbon from syngas can be fixed via the reverse TCA cycle and components thereof. Specifically, the combination of certain syngas-utilization pathway components with the pathways for formation of isopropanol, butanol, 4-hydroxybutyrate, 1,3-butanediol, or 1,4-butanediol from acetyl-CoA results in high yields of these products by providing an efficient mechanism for fixing the carbon present in carbon dioxide, fed exogenously or produced endogenously from CO, into acetyl-CoA (see below).

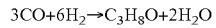
$$3CO+6H_2 \rightarrow C_3H_8O+2H_2O$$

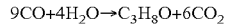
$$9CO+4H_2O \rightarrow C_3H_8O+6CO_2$$

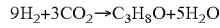
$$9H_2+3CO_2 \rightarrow C_3H_8O+5H_2O \quad \text{Isopropanol:}$$

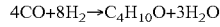
$$4CO+8H_2 \rightarrow C_4H_{10}O+3H_2O$$

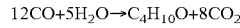
$$12CO+5H_2O \rightarrow C_4H_{10}O+8CO_2$$

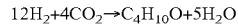
$$12H_2+4CO_2 \rightarrow C_4H_{10}O+5H_2O \quad \text{Butanol:}$$

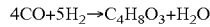
$$4CO+5H_2 \rightarrow C_4H_8O_3+H_2O$$

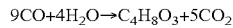
$$9CO+4H_2O \rightarrow C_4H_8O_3+5CO_2$$

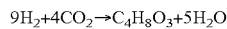
$$9H_2+4CO_2 \rightarrow C_4H_8O_3+5H_2O \quad \text{4-Hydroxybutyrate:}$$

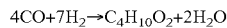
$$4CO+7H_2 \rightarrow C_4H_{10}O_2+2H_2O$$

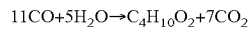
$$11CO+5H_2O \rightarrow C_4H_{10}O_2+7CO_2$$

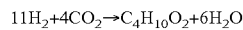
$$11H_2+4CO_2 \rightarrow C_4H_{10}O_2+6H_2O \quad \text{1,3 or 1,4-butanediol:}$$

The organisms and conversion routes described herein provide an efficient means of converting synthesis gas and its components to products such as isopropanol, butanol, 4-hydroxybutyrate, 1,3-butanediol or 1,4-butanediol. Additional product molecules that can be produced by the teachings of this invention include but are not limited to ethanol, n-propanol, isobutanol, succinic acid, fumaric acid, malic acid, 3-hydroxypropionic acid, lactic acid, adipic acid, 6-aminocaproic acid, hexamethylenediamine, 3-hydoxyisobutyric acid, 2-hydroxyisobutyric acid, methacrylic acid, acrylic acid, and long chain hydrocarbons, alcohols, acids, and esters.

While generally described herein as a microbial organism that contains a 1,4-butanediol, 4-hydroxybutyrate, 1,3-butanediol, isopropanol pathway, or other product, it is understood that the invention additionally provides a non-naturally occurring microbial organism comprising at least one exogenous nucleic acid encoding a 1,4-butanediol, 4-hydroxybutyrate, 1,3-butanediol, or isopropanol pathway enzyme expressed in a sufficient amount to produce an intermediate of a 1,4-butanediol, 4-hydroxybutyrate, 1,3-butanediol, or isopropanol pathway, or other product intermediate. For example, as disclosed herein, a 1,4-butanediol, 4-hydroxybutyrate, 1,3-butanediol, or isopropanol pathway are exemplified in FIGS. 1-4. Therefore, in addition to a microbial organism containing a 1,4-butanediol, 4-hydroxybutyrate, 1,3-butanediol, or isopropanol pathway that produces 1,4-butanediol, 4-hydroxybutyrate, 1,3-butanediol, or isopropanol, the invention additionally provides a non-naturally occurring microbial organism comprising at least one exogenous nucleic acid encoding a 1,4-butanediol, 4-hydroxybutyrate, 1,3-butanediol, or isopropanol pathway enzyme, where the microbial organism produces a 1,4-butanediol, 4-hydroxybutyrate, 1,3-butanediol, or isopropanol pathway intermediate.

It is understood that any of the pathways disclosed herein, as described in the Examples and exemplified in the Figures, including the pathways of FIGS. 1-8, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a 1,4-butanediol, 4-hydroxybutyrate, 1,3-butanediol, or isopropanol pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more 1,4-butanediol, 4-hydroxybutyrate, 1,3-butanediol, or isopropanol biosynthetic pathways. Depending on the host microbial organism chosen for biosynthesis, nucleic acids for some or all of a particular 1,4-butanediol, 4-hydroxybutyrate, 1,3-butanediol, or isopropanol biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve 1,4-butanediol, 4-hydroxybutyrate, 1,3-butanediol, or isopropanol biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as 1,4-butanediol, 4-hydroxybutyrate, 1,3-butanediol, or isopropanol.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae,* and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the 1,4-butanediol, 4-hydroxybutyrate, 1,3-butanediol, or isopropanol biosynthetic pathway constituents of a selected host microbial organism, the non-naturally occurring microbial organisms of the invention will include at least one exogenously expressed 1,4-butanediol, 4-hydroxybutyrate, 1,3-butanediol, or isopropanol pathway-encoding nucleic acid and up to all encoding nucleic acids for one or more 1,4-butanediol, 4-hydroxybutyrate, 1,3-butanediol, or isopropanol biosynthetic pathways. For example, 1,4-butanediol, 4-hydroxybutyrate, 1,3-butanediol, or isopropanol biosynthesis can be established in a host deficient in a pathway enzyme or protein through exogenous expression of the corresponding encoding nucleic acid. In a host deficient in all enzymes or proteins of a 1,4-butanediol, 4-hydroxybutyrate, 1,3-butanediol, or isopropanol pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of 1,4-butanediol, 4-hydroxybutyrate, 1,3-butanediol, or isopropanol can be included.

Given the teachings and guidance provided herein, those skilled in the art will understand that the number of encoding nucleic acids to introduce in an expressible form will, at least, parallel the 1,4-butanediol, 4-hydroxybutyrate, 1,3-butanediol, or isopropanol pathway deficiencies of the selected host microbial organism. Therefore, a non-naturally occurring microbial organism of the invention can have one, two, three, four, five, six, seven, eight, or up to all nucleic acids encoding the enzymes or proteins constituting a 1,4-butanediol, 4-hydroxybutyrate, 1,3-butanediol, or isopropanol biosynthetic pathway disclosed herein. In some embodiments, the non-naturally occurring microbial organisms also can include other genetic modifications that facilitate or optimize 1,4-butanediol, 4-hydroxybutyrate, 1,3-butanediol, or isopropanol biosynthesis or that confer other useful functions onto the host microbial organism. One such other functionality can include, for example, augmentation of the synthesis of one or more of the 1,4-butanediol, 4-hydroxybutyrate, 1,3-butanediol, or isopropanol pathway precursors.

Generally, a host microbial organism is selected such that it produces the precursor of a 1,4-butanediol, 4-hydroxybutyrate, 1,3-butanediol, or isopropanol pathway, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of a 1,4-butanediol, 4-hydroxybutyrate, 1,3-butanediol, or isopropanol pathway.

In some embodiments, a non-naturally occurring microbial organism of the invention is generated from a host that contains the enzymatic capability to synthesize 1,4-butanediol, 4-hydroxybutyrate, 1,3-butanediol, or isopropanol. In this specific embodiment it can be useful to increase the synthesis or accumulation of a 1,4-butanediol, 4-hydroxybutyrate, 1,3-butanediol, or isopropanol pathway product to, for example, drive 1,4-butanediol, 4-hydroxybutyrate, 1,3-butanediol, or isopropanol pathway reactions toward 1,4-butanediol, 4-hydroxybutyrate, 1,3-butanediol, or isopropanol production. Increased synthesis or accumulation can be accomplished by, for example, overexpression of nucleic acids encoding one or more of the above-described 1,4-butanediol, 4-hydroxybutyrate, 1,3-butanediol, or isopropanol pathway enzymes or proteins. Over expression the enzyme or enzymes and/or protein or proteins of the 1,4-butanediol, 4-hydroxybutyrate, 1,3-butanediol, or isopropanol pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing 1,4-butanediol, 4-hydroxybutyrate, 1,3-butanediol, or isopropanol, through overexpression of one, two, three, four, five, six, seven, eight, up to all nucleic acids encoding 1,4-butanediol, 4-hydroxybutyrate, 1,3-butanediol, or isopropanol biosynthetic pathway enzymes or proteins. In addition, a non-naturally occurring organism can be generated by mutagenesis of an endogenous gene that results in an increase in activity of an enzyme in the 1,4-butanediol, 4-hydroxybutyrate, 1,3-butanediol, or isopropanol biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a 1,4-butanediol, 4-hydroxybutyrate, 1,3-butanediol, or isopropanol biosynthetic pathway onto the microbial organism. Alternatively, encoding nucleic acids can be introduced to produce an intermediate microbial organism having the biosynthetic capability to catalyze some of the required reactions to confer 1,4-butanediol, 4-hydroxybutyrate, 1,3-butanediol, or isopropanol biosynthetic capability. For example, a non-naturally occurring microbial organism having a 1,4-butanediol, 4-hydroxybutyrate, 1,3-butanediol, or isopropanol biosynthetic pathway can comprise at least two exogenous nucleic acids encoding desired enzymes or proteins. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, as desired, so long as the combination of enzymes and/or proteins of the desired biosynthetic pathway results in production of the corresponding desired product. Similarly, any combination of four or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of 1,4-butanediol, 4-hydroxybutyrate, 1,3-butanediol, or isopropanol as described herein, the non-naturally occurring microbial organisms and methods of the invention also can be utilized in various combinations with each other and with other microbial organisms and methods well known in the art to achieve product biosynthesis by other routes. For example, one alternative to produce 1,4-butanediol, 4-hydroxybutyrate, 1,3-butanediol, or isopropanol other than use of the 1,4-butanediol, 4-hydroxybutyrate, 1,3-butanediol, or isopropanol producers is through addition of another microbial organism capable of converting a 1,4-butanediol, 4-hydroxybutyrate, 1,3-butanediol, or isopropanol pathway intermediate to 1,4-butanediol, 4-hydroxybutyrate, 1,3-butanediol, or isopropanol. One such procedure includes, for example, the fermentation of a microbial organism that produces a 1,4-butanediol, 4-hydroxybutyrate, 1,3-butanediol, or isopropanol pathway intermediate. The 1,4-butanediol, 4-hydroxybutyrate, 1,3-butanediol, or isopropanol pathway intermediate can then be used as a substrate for a second microbial organism that converts the 1,4-butanediol, 4-hydroxybutyrate, 1,3-butanediol, or isopropanol pathway intermediate to 1,4-butanediol, 4-hydroxybutyrate, 1,3-butanediol, or isopropanol. The 1,4-butanediol, 4-hydroxybutyrate, 1,3-butanediol, or isopropanol pathway intermediate can be added directly to another culture of the second organism or the original culture of the 1,4-butanediol, 4-hydroxybutyrate, 1,3-butanediol, or isopropanol pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, 1,4-butanediol, 4-hydroxybutyrate, 1,3-butanediol, or isopropanol. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of 1,4-butanediol, 4-hydroxybutyrate, 1,3-butanediol, or isopropanol can be accomplished by constructing a microbial organism that contains biosynthetic pathways for conversion of one pathway intermediate to another pathway intermediate or the product. Alternatively, 1,4-butanediol, 4-hydroxybutyrate, 1,3-butanediol, or isopropanol also can be biosynthetically produced from microbial organisms through co-culture or co-fermentation using two organisms in the same vessel, where the first microbial organism produces a 1,4-butanediol, 4-hydroxybutyrate, 1,3-butanediol, or isopropanol intermediate and the second microbial organism converts the intermediate to 1,4-butanediol, 4-hydroxybutyrate, 1,3-butanediol, or isopropanol.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 1,4-butanediol, 4-hydroxybutyrate, 1,3-butanediol, or isopropanol.

Sources of encoding nucleic acids for a 1,4-butanediol, 4-hydroxybutyrate, 1,3-butanediol, or isopropanol pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, *S. cerevisiae*, *B. subtilis*, *Candida boidinii*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 1,4-butanediol, 4-hydroxybutyrate, 1,3-butanediol, or isopropanol biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of 1,4-butanediol, 4-hydroxybutyrate, 1,3-butanediol, or isopropanol described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 1,4-butanediol, 4-hydroxybutyrate, 1,3-butanediol, or isopropanol biosynthetic pathway exists in an unrelated species, 1,4-butanediol, 4-hydroxybutyrate, 1,3-butanediol, or isopropanol biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 1,4-butanediol, 4-hydroxybutyrate, 1,3-butanediol, or isopropanol.

Methods for constructing and testing the expression levels of a non-naturally occurring 1,4-butanediol, 4-hydroxybutyrate, 1,3-butanediol, or isopropanol-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of 1,4-butanediol, 4-hydroxybutyrate, 1,3-butanediol, or isopropanol can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more 1,4-butanediol, 4-hydroxybutyrate, 1,3-butanediol, or isopropanol biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the present invention provides a method for enhancing carbon flux through acetyl-CoA that includes culturing the aforementioned non-naturally occurring microbial organisms under conditions and for a sufficient period of time to produce a product having acetyl-CoA as a building block. Such culturing can be in a substantially anaerobic culture medium and can include organisms having any number of exogenous nucleic acids as described herein above.

As described above, these cultured organisms can have an isopropanol pathway, a 1,3-butanediol pathway; a 1,4-butanediol pathway, a 4-hydroxybutrate pathway, or any other functional pathway that utilizes acetyl-CoA. The culturing of these microbial organism can be performed with a carbon feedstock selected from CO, $CO_2$, and $H_2$, synthesis gas comprising CO and $H_2$, and synthesis gas comprising CO, $CO_2$, and $H_2$.

Suitable purification and/or assays to test for the production of 1,4-butanediol, 4-hydroxybutyrate, 1,3-butanediol, or isopropanol can be performed using well known methods.

Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods well known in the art.

The 1,4-butanediol, 4-hydroxybutyrate, 1,3-butanediol, or isopropanol can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the 1,4-butanediol, 4-hydroxybutyrate, 1,3-butanediol, or isopropanol producers can be cultured for the biosynthetic production of 1,4-butanediol, 4-hydroxybutyrate, 1,3-butanediol, or isopropanol.

For the production of 1,4-butanediol, 4-hydroxybutyrate, 1,3-butanediol, or isopropanol, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 1,4-butanediol, 4-hydroxybutyrate, 1,3-butanediol, or isopropanol.

In addition to renewable feedstocks such as those exemplified above, the 1,4-butanediol, 4-hydroxybutyrate, 1,3-butanediol, or isopropanol microbial organisms of the invention also can be modified for growth on syngas as its source of carbon. In this specific embodiment, one or more proteins or enzymes are expressed in the 1,4-butanediol, 4-hydroxybutyrate, 1,3-butanediol, or isopropanol producing organisms to provide a metabolic pathway for utilization of syngas or other gaseous carbon source.

Given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, 1,4-butanediol, 4-hydroxybutyrate, 1,3-butanediol, or isopropanol and any of the intermediate metabolites in the 1,4-butanediol, 4-hydroxybutyrate, 1,3-butanediol, or isopropanol pathway. All that is required is to engineer in one or more of the required enzyme or protein activities to achieve biosynthesis of the desired compound or intermediate including, for example, inclusion of some or all of the 1,4-butanediol, 4-hydroxybutyrate, 1,3-butanediol, or isopropanol biosynthetic pathways. Accordingly, the invention provides a non-naturally occurring microbial organism that produces and/or secretes 1,4-butanediol, 4-hydroxybutyrate, 1,3-butanediol, or isopropanol when grown on a carbohydrate or other carbon source and produces and/or secretes any of the intermediate metabolites shown in the 1,4-butanediol, 4-hydroxybutyrate, 1,3-butanediol, or isopropanol pathway when grown on a carbohydrate or other carbon source. The 1,4-butanediol, 4-hydroxybutyrate, 1,3-butanediol, or isopropanol producing microbial organisms of the invention can initiate synthesis from an intermediate.

The non-naturally occurring microbial organisms of the invention are constructed using methods well known in the art as exemplified herein to exogenously express at least one nucleic acid encoding a 1,4-butanediol, 4-hydroxybutyrate, 1,3-butanediol, or isopropanol pathway enzyme or protein in sufficient amounts to produce 1,4-butanediol, 4-hydroxybutyrate, 1,3-butanediol, or isopropanol. It is understood that the microbial organisms of the invention are cultured under conditions sufficient to produce 1,4-butanediol, 4-hydroxybutyrate, 1,3-butanediol, or isopropanol. Following the teachings and guidance provided herein, the non-naturally occurring microbial organisms of the invention can achieve biosynthesis of 1,4-butanediol, 4-hydroxybutyrate, 1,3-butanediol, or isopropanol resulting in intracellular concentrations between about 0.1-200 mM or more. Generally, the intracellular concentration of 1,4-butanediol, 4-hydroxybutyrate, 1,3-butanediol, or isopropanol is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the 1,4-butanediol, 4-hydroxybutyrate, 1,3-butanediol, or isopropanol producers can synthesize 1,4-butanediol, 4-hydroxybutyrate, 1,3-butanediol, or isopropanol at intracellular concentrations of 5-10 mM or more as well as all other concentrations exemplified herein. It is understood that, even though the above description refers to intracellular concentrations, 1,4-butanediol, 4-hydroxybutyrate, 1,3-butanediol, or isopropanol producing microbial organisms can produce 1,4-butanediol, 4-hydroxybutyrate, 1,3-butanediol, or isopropanol intracellularly and/or secrete the product into the culture medium.

In addition to the culturing and fermentation conditions disclosed herein, growth condition for achieving biosynthesis of 1,4-butanediol, 4-hydroxybutyrate, 1,3-butanediol, or isopropanol can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopoprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 1,4-butanediol, 4-hydroxybutyrate, 1,3-butanediol, or isopropanol includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of 1,4-butanediol, 4-hydroxybutyrate, 1,3-butanediol, or isopropanol. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 1,4-butanediol, 4-hydroxybutyrate, 1,3-butanediol, or isopropanol. Generally, and as with non-continuous culture procedures, the continuous and/or near-continuous production of 1,4-butanediol, 4-hydroxybutyrate, 1,3-butanediol, or isopropanol will include culturing a non-naturally occurring 1,4-butanediol, 4-hydroxybutyrate, 1,3-butanediol, or isopropanol producing organism of the invention in sufficient nutrients and medium to sustain and/or nearly sustain growth in an exponential phase. Continuous culture under such conditions can be included, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 1,4-butanediol, 4-hydroxybutyrate, 1,3-butanediol, or isopropanol can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the 1,4-butanediol, 4-hydroxybutyrate, 1,3-butanediol, or isopropanol producers of the invention for continuous production of substantial quantities of 1,4-butanediol, 4-hydroxybutyrate, 1,3-butanediol, or isopropanol, the 1,4-butanediol, 4-hydroxybutyrate, 1,3-butanediol, or isopropanol producers also can be, for example, simultaneously subjected to chemical synthesis procedures to convert the product to other compounds or the product can be separated from the fermentation culture and sequentially subjected to chemical conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No.

7,127,379). Modeling analysis allows reliable predictions of the effects on cell growth of shifting the metabolism towards more efficient production of 1,4-butanediol, 4-hydroxybutyrate, 1,3-butanediol, or isopropanol.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a 1,4-butanediol, 4-hydroxybutyrate, 1,3-butanediol, or isopropanol pathway can be introduced into a host organism. In some cases, it can be desirable to modify an activity of a 1,4-butanediol, 4-hydroxybutyrate, 1,3-butanediol, or isopropanol pathway enzyme or protein to increase production of 1,4-butanediol, 4-hydroxybutyrate, 1,3-butanediol, or isopropanol. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng.* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng.* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a 1,4-butanediol, 4-hydroxybutyrate, 1,3-butanediol, or isopropanol pathway enzyme or protein. Such methods include, but are not limited to EpPCR, which introduces random point mutations by reducing the fidelity of DNA polymerase in PCR reactions (Pritchard et al., *J. Theon. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc. Natl. Acad. Sci. U.S.A.* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res.* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol.* 352:191-204 (2007); Bergquist et al., *Biomol. Eng.* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. U.S.A.* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res.* 29:E16 (2001)); SCRATCHY, which combines two methods for recombining genes, ITCHY and DNA shuffling (Lutz et al., *Proc. Natl. Acad. Sci. U.S.A.* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. U.S.A.* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. U.S.A.* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

It is understood that modifications which do not substantially affect the activity of the various embodiments of this invention are also included within the definition of the invention provided herein. Accordingly, the following examples are intended to illustrate but not limit the present invention.

EXAMPLES

Non-Naturally Occurring Organism to Produce 1,3-Butanediol, Isopropanol, 4-Hydroxybutyrate or 1,4-Butanediol from Acetyl-CoA In the following Examples, pathways for formation of 1,3-BDO (FIG. 1A), isopropanol (FIG. 1B), 4-HB (FIG. 1C), and 1,4-BDO (FIG. 1D) are described from the intermediate, acetyl-CoA. The maximum theoretical yield of each of these product molecules from glucose is 1 mole per mole using only the metabolic pathways proceeding from acetyl-CoA as described herein. Specifically, 2 moles of acetyl-CoA are derived per mole of glucose via glycolysis and 2 moles of acetyl-CoA are used per mole of 1,3-butanediol, isopropanol, 4-hydroxybutyrate, or 1,4-butanediol. The net conversions are described by the following stoichiometric equations:

$C_6H_{12}O_6 \rightarrow C_4H_{10}O_2 + CH_2O_2 + CO_2$   1,3-Butanediol:

$C_6H_{12}O_6 + 1.5O_2 \rightarrow C_3H_8O + 3CO_2 + 2H_2O$   Isopropanol:

$C_6H_{12}O_6 + 1.5O_2 \rightarrow C_4H_8O_3 + 2CO_2 + 2H_2O$   4-Hydroxybutyate:

$C_6H_{12}O_6 \rightarrow C_4H_{10}O_2 + CH_2O_2 + CO_2$   1,4-Butanediol:

Example I

1,3-Butanediol Synthesis Pathway 1,3-butanediol production can be achieved in recombinant E. coli by alternative pathways as described in FIG. 1A. All pathways first convert two molecules of acetyl-CoA into one molecule of acetoacetyl-CoA employing a thiolase.

Acetoacetyl-CoA thiolase converts two molecules of acetyl-CoA into one molecule each of acetoacetyl-CoA and CoA. Exemplary acetoacetyl-CoA thiolase enzymes include the gene products of atoB from E. coli (Martin et al., Nat. Biotechnol. 21:796-802 (2003), thlA and thlB from C. acetobutylicum (Hanai et al., Appl. Environ. Microbiol. 73:7814-7818 (2007); Winzer et al., J. Mol. Microbiol. Biotechnol. 2:531-541 (2000), and ERG10 from S. cerevisiae (Hiser et al., J. Biol. Chem. 269:31383-31389 (1994).

| Protein | GenBank ID | GI number | Organism |
|---------|------------|-----------|----------|
| AtoB | NP_416728 | 16130161 | Escherichia coli |
| ThlA | NP_349476.1 | 15896127 | Clostridium acetobutylicum |
| ThlB | NP_149242.1 | 15004782 | Clostridium acetobutylicum |
| ERG10 | NP_015297 | 6325229 | Saccharomyces cerevisiae |

Acetoacetyl-CoA can first be reduced to 3-hydroxybutyryl-CoA by acetoacetyl-CoA reductase (ketone reducing). This can subsequently be converted to 3-hydroxybutyraldehyde via a CoA-dependent aldehyde reductase called 3-hydroxybutyryl-CoA reductase. 3-hydroxybutyraldehyde can eventually be reduced to the product 1,3-BDO by 3-hydroxybutyraldehyde reductase. Alternatively, 3-hydroxybutyryl-CoA can be reduced directly to 1,3-BDO by an alcohol-forming CoA-dependent 3-hydroxybutyryl-CoA reductase. The gene candidates for each of the steps in the pathway are described below.

Acetoacetyl-CoA reductase catalyzing the reduction of acetoacetyl-CoA to 3-hydroxybutyryl-CoA participates in the acetyl-CoA fermentation pathway to butyrate in several species of Clostridia and has been studied in detail (Jones and Woods, Microbiol. Rev. 50:484-524 (1986)). The enzyme from Clostridium acetobutylicum, encoded by hbd, has been cloned and functionally expressed in E. coli (Youngleson et al., J. Bacteriol. 171:6800-6807 (1989)). Additionally, subunits of two fatty acid oxidation complexes in E. coli, encoded by fadB and fadJ, function as 3-hydroxyacyl-CoA dehydrogenases (Binstockand Schulz, Methods Enzymol. 71 Pt C:403-411 (1981)). Yet other gene candidates demonstrated to reduce acetoacetyl-CoA to 3-hydroxybutyryl-CoA are phbB from Zoogloea ramigera (Ploux et al., Eur. J. Biochem. 174:177-182 (1988) and phaB from Rhodobacter sphaeroides (Alber et al., Mol. Microbiol. 61:297-309 (2006). The former gene candidate is NADPH-dependent, its nucleotide sequence has been determined (Peoples and Sinskey, Mol. Microbiol. 3:349-357 (1989) and the gene has been expressed in E. coli. Substrate specificity studies on the gene led to the conclusion that it could accept 3-oxopropionyl-CoA as a substrate besides acetoacetyl-CoA (Ploux et al., Eur. J. Biochem. 174:177-182 (1988)). Additional gene candidates include Hbd1 (C-terminal domain) and Hbd2 (N-terminal domain) in Clostridium kluyveri (Hillmer and Gottschalk, Biochim. Biophys. Acta 3334:12-23 (1974)) and HSD17B10 in Bos taurus (Wakil et al., J. Biol. Chem. 207:631-638 (1954)).

| Protein | Genbank ID | GI number | Organism |
|---------|------------|-----------|----------|
| fadB | P21177.2 | 119811 | Escherichia coli |
| fadJ | P77399.1 | 3334437 | Escherichia coli |
| Hbd2 | EDK34807.1 | 146348271 | Clostridium kluyveri |
| Hbd1 | EDK32512.1 | 146345976 | Clostridium kluyveri |
| hbd | P52041.2 | | Clostridium acetobutylicum |
| HSD17B10 | O02691.3 | 3183024 | Bos Taurus |
| phbB | P23238.1 | 130017 | Zoogloea ramigera |
| phaB | YP_353825.1 | 77464321 | Rhodobacter sphaeroides |

A number of similar enzymes have been found in other species of Clostridia and in Metallosphaera sedula (Berg et al., Science 318:1782-1786 (2007).

| Protein | GenBank ID | GI number | Organism |
|---------|------------|-----------|----------|
| hbd | NP_349314.1 | NP_349314.1 | Clostridium acetobutylicum |

| Protein | GenBank ID | GI number | Organism |
|---|---|---|---|
| hbd | AAM14586.1 | AAM14586.1 | Clostridium beijerinckii |
| Msed_1423 | YP_001191505 | YP_001191505 | Metallosphaera sedula |
| Msed_0399 | YP_001190500 | YP_001190500 | Metallosphaera sedula |
| Msed_0389 | YP_001190490 | YP_001190490 | Metallosphaera sedula |
| Msed_1993 | YP_001192057 | YP_001192057 | Metallosphaera sedula |

Several acyl-CoA dehydrogenases are capable of reducing an acyl-CoA to its corresponding aldehyde. Exemplary genes that encode such enzymes include the *Acinetobacter calcoaceticus* acyl encoding a fatty acyl-CoA reductase (Reiser and Somerville, J. Bacteriol. 179:2969-2975 (1997), the *Acinetobacter* sp. M-1 fatty acyl-CoA reductase (Ishige et al., Appl. Environ. Microbiol. 68:1192-1195 (2002), and a CoA- and NADP-dependent succinate semialdehyde dehydrogenase encoded by the sucD gene in *Clostridium kluyveri* (Sohling and Gottschalk, *J. Bacteriol.* 178:871-880 (1996); Sohling and Gottschalk, *J. Bacteriol.* 1778:871-880 (1996)). SucD of *P. gingivalis* is another succinate semialdehyde dehydrogenase (Takahashi et al., *J. Bacteriol.* 182:4704-4710 (2000). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:45-55 (1972); Koo et al., *Biotechnol. Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol. Biochem.* 71:58-68 (2007)).

| Protein | GenBank ID | GI number | Organism |
|---|---|---|---|
| acr1 | YP_047869.1 | 50086359 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |
| adhE | AAV66076.1 | 55818563 | Leuconostoc mesenteroides |
| bld | AAP42563.1 | 31075383 | Clostridium saccharoperbutylacetonicum |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., *Science* 318:1782-1786 (2007); Thauer, *Science* 318:1732-1733 (2007)). The enzyme utilizes NADPH as a cofactor and has been characterized in *Metallosphaera* and *Sulfolobus* spp (Alber et al., *J. Bacteriol.* 188:8551-8559 (2006); Hugler et al., *J. Bacteriol.* 184:2404-2410 (2002)). The enzyme is encoded by Msed_0709 in *Metallosphaera sedula* (Alber et al., supra (2006); Berg et al., *Science* 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006)). This enzyme has also been shown to catalyze the conversion of methylmalonyl-CoA to its corresponding aldehyde (WO 2007/141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl. Environ. Microbiol.* 65:4973-4980 (1999). This enzyme has been reported to reduce acetyl-CoA and butyryl-CoA to their corresponding aldehydes. This gene is very similar to cutE that encodes acetaldehyde dehydrogenase of *Salmonella typhimurium* and *E. coli* (Toth et al., supra).

| Protein | GenBank ID | GI number | Organism |
|---|---|---|---|
| Msed_0709 | YP_001190808.1 | 146303492 | Metallosphaera sedula |
| mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 9473535 | Clostridium beijerinckii |
| eutE | AAA80209 | 687645 | Salmonella typhimurium |
| eutE | P77445 | 2498347 | Escherichia coli |

Enzymes exhibiting 3-hydroxybutyraldehyde reductase activity (EC 1.1.1.61) have been characterized in *Ralstonia eutropha* (Bravo et al., *J. Forensic Sci.* 49:379-387 (2004)), *Clostridium kluyveri* (Wolff and Kenealy, *Protein Expr. Pur* 6:206-212 (1995)) and *Arabidopsis thaliana* (Breitkreuz et al., *J. Biol. Chem.* 278:41552-41556 (2003). Yet another gene candidate is the alcohol dehydrogenase adhI from *Geobacillus thermoglucosidasius* (Jeon et al., *J. Biotechnol.* 135:127-133 (2008).

| Protein | GenBank ID | GI number | Organism |
|---|---|---|---|
| 4hbd | YP_726053.1 | 113867564 | Ralstonia eutropha H16 |
| 4hbd | L21902.1 | 146348486 | Clostridium kluyveri DSM 555 |
| 4hbd | Q94B07 | 75249805 | Arabidopsis thaliana |
| adhI | AAR91477.1 | 40795502 | Geobacillus thermoglucosidasius M10EXG |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J. Mol. Biol.* 352:905-917 (2005)). The reversibility of the human 3-hydroxyisobutyrate dehydrogenase was demonstrated using isotopically-labeled substrate (Manning and Pollitt, *Biochem. J.* 231:481-484 (1985)). Additional genes encoding this enzyme include 3hidh in *Homo sapiens* (Hawes et al., *Methods Enzymol.* 324:218-228 (2000) and *Oryctolagus cuniculus* (Hawes et al., supra; Chowdhury et al., *Biosci. Biotechnol.* 60:2043-2047 (1996), mmsb in *Pseudomonas aeruginosa*, and dhat in *Pseudomonas putida* (Aberhart and Hsu, *J. Chem. Soc.* [Perkin 1] 6:1404-1406 (1979); Chowdhury et al., supra; Chowdhury et al., *Biosci. Biotechnol. Biochem.* 67:438-441 (2003)).

| Protein | GenBank ID | GI number | Organism |
|---|---|---|---|
| P84067 | P84067 | 75345323 | *Thermus thermophilus* |
| mmsb | P28811.1 | 127211 | *Pseudomonas aeruginosa* |
| dhat | Q59477.1 | 2842618 | *Pseudomonas putida* |
| 3hidh | P31937.2 | 12643395 | *Homo sapiens* |
| 3hidh | P32185.1 | 416872 | *Oryctolagus cuniculus* |

Other exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *App. Environ. Microbiol.* 66:5231-5235 (2000), ADH2 from *Saccharomyces cerevisiae* (Atsumi et al., *Nature* 451:86-89 (2008)), yqhD from *E. coli* which has preference for molecules longer than C3 (Sulzenbacher et al., *J. Mol. Biol.* 342:489-502 (2004), and bdh I and bdh II from *C. acetobutylicum* which converts butyraldehyde into butanol (Walter et al., *J. Bacteriol.* 174:7149-7158 (1992)). The gene product of yqhD catalyzes the reduction of acetaldehyde, malondialdehyde, propionaldehyde, butyraldehyde, and acrolein using NADPH as the cofactor (Perez et al., *J. Biol. Chem.* 283:7346-7353 (2008)). ADH1 from *Zymomonas mobilis* has been demonstrated to have activity on a number of aldehydes including formaldehyde, acetaldehyde, propionaldehyde, butyraldehyde, and acrolein (Kinoshita et al., *Appl. Microbiol. Biotechnol.* 22:249-254 (1985)). The protein sequences for each of these exemplary gene products, if available, can be found using the following GenBank accession numbers:

| Protein | GenBank ID | GI number | Organism |
|---|---|---|---|
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Exemplary two-step oxidoreductases that convert an acyl-CoA to alcohol include those that transform substrates such as acetyl-CoA to ethanol (e.g., adhE from *E. coli* (Kessler et al., *FEES Lett.* 281:59-63 (1991)) and butyryl-CoA to butanol (e.g. adhE2 from *C. acetobutylicum* (Fontaine et al., *J. Bacteriol.* 184:821-830 (2002)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:43-55 (1972); Koo et al., *Biotechnol. Lett.* 27:505-510 (2005)).

| Protein | GenBank ID | GI number | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2002); Strauss and Fuchs, Eur. J. Biochem. 215:633-643 (1993). This enzyme, with a mass of 300 kDa, is highly substrate-specific and shows little sequence similarity to other known oxidoreductases (Hugler, supra (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | GI number | Organism |
|---|---|---|---|
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al., *Plant Physiol.* 122:635-644 (2000)).

FAR AAD38039.1 5020215 *Simmondsia chinensis*

The reduction of acetoacetyl-CoA into 3-oxobutyraldehyde can be accomplished via the CoA-dependent aldehyde forming acetoacetyl-CoA reductase. 3-oxobutyraldehyde is next reduced to 3-hydroxybutyraldehyde by 3-oxobutyraldehyde reductase (ketone reducing), and eventually, this intermediate is reduced to 1,3-butanediol by a 3-hydroxybutyraldehyde reductase. The candidates for each of these steps are listed below.

The enzymes for acetoacetyl-CoA reductase (CoA-dependent, aldehyde forming) are the same as that for the aldehyde forming 3-hydroxybutyryl-CoA reductase described above.

There exist several exemplary alcohol dehydrogenases that convert a ketone to a hydroxyl functional group. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on substrates of various chain lengths such as lactate, 2-oxobutyrate, 2-oxopentanoate and 2-oxoglutarate (Steinbuchel and Schlegel, *Eur. J. Biochem.* 130:329-334 (1983)). Conversion of the oxo functionality to the hydroxyl group can also be catalyzed by 2-keto1,3-butanediol reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). All of these enzymes are good candidates for 3-oxobutyraldehyde reductase. An additional candidate for these steps is the mitochondrial 3-hydroxybutyrate dehydrogenase (bdh) from the human heart which has been cloned and characterized (Marks et al., *J. Biol. Chem.* 267:15459-15463 (1992)). This enzyme is a dehydrogenase that operates on a 3-hydroxyacid. Another exemplary alcohol dehydrogenase that converts acetone to isopropanol as was shown in *C. beijerinckii* (Ismaiel et al., *J. Bacteriol.* 175:5097-5105 (1993) and *T. brockii* (Lamed and Zeikus, *Biochem. J.* 195:183-190 (1981); Peretz and Burstein, *Biochemistry* 28:6549-6555 (1989)). Methyl ethyl ketone (MEK) reductase, or alternatively, 2-butanol dehydrogenase, catalyzes the reduction of MEK to form 2-butanol. Exemplary enzymes can be found in *Rhodococcus ruber* (Kosjek et al., *Biotechnol. Bioeng.* 86:55-62 (2004) and *Pyrococcus furiosus* (van der et al. 2001).

| Protein | GenBank ID | GI number | Organism |
|---|---|---|---|
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* |
| adh | P14941.1 | 113443 | *Thermoanaerobacter brockii* |
| sadh | CAD36475 | 21615553 | *Rhodococcus ruber* |
| adhA | 3288810 | AAC25556 | *Pyrococcus furiosus* |

Acetoacetyl-CoA can also be reduced to 4-hydroxy, 2-butanone by the CoA-dependent, alcohol forming acetoacetyl-CoA reductase. This intermediate is then reduced to 1,3-butanediol by 4-hydroxybutanone reductase. 4-hydroxybutanone can also be formed from 3-oxobutyraldehyde by an aldehyde reducing 3-oxobutyraldehyde reductase.

Enzymes for acetoacetyl-CoA reductase (CoA-dependent, alcohol forming) are the same as those for the alcohol-forming 3-hydroxybutyryl-CoA reductase described herein.

The enzymes for 4-hydroxybutanone reductase are the same as those described for 3-oxobutyraldehyde reductase. Additionally, a number of organisms can catalyze the reduction of 4-hydroxy, 2-butanone to 1,3-butanediol, including those belonging to the genus *Bacillus, Brevibacterium, Candida,* and *Klebsiella* among others, as described by Matsuyama et al. (1).

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000), ADH2 from *Saccharomyces cerevisiae* (Atsumi et al., *Nature* 451:86-89 (2008), yqhD from *E. coli* which has preference for molecules longer than C3 (Sulzenbacher et al., *J. Mol. Biol.* 342:489-502 (2004), and bdh I and bdh II from *C. acetobutylicum* which converts butyraldehyde into butanol (Walter et al., *J. Bacteriol.* 174:7149-7158 (1992). The gene product of yqhD catalyzes the reduction of acetaldehyde, malondialdehyde, propionaldehyde, butyraldehyde, and acrolein using NADPH as the cofactor (Perez et al., *J. Biol. Chem.* 283:7346-7353 (2008)). ADH1 from *Zymomonas mobilis* has been demonstrated to have activity on a number of aldehydes including formaldehyde, acetaldehyde, propionaldehyde, butyraldehyde, and acrolein (Kinoshita et al., *Appl. Microbiol. Biotechnol.* 22:249-254 (1985)).

The protein sequences for each of these exemplary gene products, if available, can be found using the following GenBank accession numbers:

| Protein | GenBank ID | GI number | Organism |
|---|---|---|---|
| alrA | BAB12273.1 | 9967138 | *Acinetobacter sp. strain M-1* |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Acetoacetyl-CoA can be converted into acetoacetate by acetoacetyl-CoA transferase, hydrolase, or synthetase. Acetoacetate can next be reduced to 3-hydroxybutyrate by 3-hydroxybutyrate dehydrogenase and that gets further converted into 3-hydroxybutyraldehyde by 3-hydroxybutyrate reductase. Alternatively, acetoacetate can be reduced to 3-oxobutyraldehyde by acetoacetate reductase. 3-hydroxybutyryl-CoA can also be transformed into 3-hdyroxybutyrate via 3-hydroxybutyryl-CoA transferase, hydrolase, or synthetase.

The conversion of acetoacetyl-CoA to acetoacetate can be carried out by an acetoacetyl-CoA transferase which conserves the energy stored in the CoA-ester bond. Several exemplary transferase enzymes capable of catalyzing this transformation are provided below. These enzymes either naturally exhibit the desired acetoacetyl-CoA transferase activity or they can be engineered via directed evolution to accept acetetoacetyl-CoA as a substrate with increased efficiency. Such enzymes, either naturally or following directed evolution, are also suitable for catalyzing the conversion of 3-hydroxybutyryl-CoA to 3-hydroxybutyrate via a transferase mechanism.

Acetoacetyl-CoA:acetyl-CoA transferase naturally converts acetoacetyl-CoA and acetate to acetoacetate and acetyl-CoA. This enzyme may also accept 3-hydroxybutyryl-CoA as a substrate or could be engineered to do so. Exemplary enzymes include the gene products of atoAD from *E. coli* (Hanai et al., *Appl Environ Microbiol* 73:7814-7818 (2007)), ctfAB from *C. acetobutylicum* (Jojima et al., *Appl Microbiol Biotechnol* 77:1219-1224 (2008)), and ctfAB from *Clostridium saccharoperbutylacetonicum* (Kosaka et al., *Biosci. Biotechnol Biochem.* 71:58-68 (2007)). Information related to these proteins and genes is shown below.

| Protein | GenBank ID | GI number | Organism |
|---|---|---|---|
| AtoA | P76459.1 | 2492994 | *Escherichia coli* |
| AtoD | P76458.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Succinyl-CoA:3-ketoacid-CoA transferase naturally converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., *Genomics* 68:144-151 (2000); Tanaka et al., *Mol. Hum. Reprod.* 8:16-23 (2002)). Information related to these proteins and genes is shown below:

| Protein | GenBank ID | GI number | Organism |
|---|---|---|---|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Additional suitable acetoacetyl-CoA and 3-hydroxybutyryl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA acetyltransferase activity, respectively (Seedorf et al., Proc. Natl. Acad. Sci. USA 105:2128-2133 (2008); Sohling and Gottschalk, J Bacteriol 178:871-880 (1996)). Similar CoA transferase activities are also present in Trichomonas vaginalis (van Grinsven et al., J. Biol. Chem. 283:1411-1418 (2008)) and Trypanosoma brucei (Riviere et al., J. Biol. Chem. 279:45337-45346 (2004)). Yet another transferase capable of the desired conversions is butyryl-CoA: acetoacetate CoA-transferase. Exemplary enzymes can be found in Fusobacterium nucleatum (Barker et al., J. Bacteriol. 152(1):201-7 (1982)), Clostridium SB4 (Barker et al., J. Biol. Chem. 253(4):1219-25 (1978)), and Clostridium acetobutylicum (Wiesenborn et al., Appl. Environ. Microbiol. 55(2):323-9 (1989)). Although specific gene sequences were not provided for butyryl-CoA: acetoacetate CoA-transferase in these references, the genes FNO272 and FNO273 have been annotated as a butyrate-acetoacetate CoA-transferase (Kapatral et al., J. Bact. 184(7) 2005-2018 (2002)). Homologs in Fusobacterium nucleatum such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., J. Biol. Chem. 282 (10) 7191-7197 (2007)). Additional candidates from Porphyrmonas gingivalis and Thermoanaerobacter tengcongensis can be identified in a similar fashion (Kreimeyer, et al., J. Biol. Chem. 282 (10) 7191-7197 (2007)). Information related to these proteins and genes is shown below:

| Protein | GenBank ID | GI number | Organism |
| --- | --- | --- | --- |
| Cat1 | P38946.1 | 729048 | Clostridium kluyveri |
| Cat2 | P38942.2 | 1705614 | Clostridium kluyveri |
| Cat3 | EDK35586.1 | 146349050 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| FN0272 | NP_603179.1 | 19703617 | Fusobacterium nucleatum |
| FN0273 | NP_603180.1 | 19703618 | Fusobacterium nucleatum |
| FN1857 | NP_602657.1 | 19705162 | Fusobacterium nucleatum |
| FN1856 | NP_602656.1 | 19705161 | Fusobacterium nucleatum |
| PG1066 | NP_905281.1 | 34540802 | Porphyromonas gingivalis W83 |
| PG1075 | NP_905290.1 | 34540811 | Porphyromonas gingivalis W83 |
| TTE0720 | NP_622378.1 | 20807207 | Thermoanaerobacter tengcongensis MB4 |
| TTE0721 | NP_622379.1 | 20807208 | Thermoanaerobacter tengcongensis MB4 |

Acetoacetyl-CoA can be hydrolyzed to acetoacetate by acetoacetyl-CoA hydrolase. Similarly, 3-hydroxybutyryl-CoA can be hydrolyzed to 3-hydroxybutyate by 3-hydroxybutyryl-CoA hydrolase. Many CoA hydrolases (EC 3.1.2.1) have broad substrate specificity and are suitable enzymes for these transformations either naturally or following enzyme engineering. Though the sequences were not reported, several acetoacetyl-CoA hydrolases were identified in the cytosol and mitochondrion of the rat liver (Aragon and Lowenstein, J. Biol. Chem. 258(8):4725-4733 (1983)). Additionally, an enzyme from Rattus norvegicus brain (Robinson et al., Biochem. Biophys. Res. Commun. 71:959-965 (1976)) can react with butyryl-CoA, hexanoyl-CoA and malonyl-CoA. The acot12 enzyme from the rat liver was shown to hydrolyze C2 to C6 acyl-CoA molecules (Suematsu et al., Eur. J. Biochem. 268:2700-2709 (2001)). Though its sequence has not been reported, the enzyme from the mitochondrion of the pea leaf showed activity on acetyl-CoA, propionyl-CoA, butyryl-CoA, palmitoyl-CoA, oleoyl-CoA, succinyl-CoA, and crotonyl-CoA (Zeiher and Randall, Plant. Physiol. 94:20-27 (1990)). Additionally, a glutaconate CoA-transferase from Acidaminococcus fermentans was transformed by site-directed mutagenesis into an acyl-CoA hydrolase with activity on glutaryl-CoA, acetyl-CoA and 3-butenoyl-CoA (Mack and Buckel, FEES Lett. 405:209-212 (1997)). This indicates that the enzymes encoding succinyl-CoA:3-ketoacid-CoA transferases and acetoacetyl-CoA:acetyl-CoA transferases can also be used as hydrolases with certain mutations to change their function. The acetyl-CoA hydrolase, ACH1, from S. cerevisiae represents another candidate hydrolase (Buu et al., J. Biol. Chem. 278:17203-17209 (2003)). Information related to these proteins and genes is shown below.

| Protein | GenBank ID | GI number | Organism |
| --- | --- | --- | --- |
| Acot12 | NP_570103.1 | 18543355 | Rattus norvegicus |
| GctA | CAA57199 | 559392 | Acidaminococcus fermentans |
| GctB | CAA57200 | 559393 | Acidaminococcus fermentans |
| ACH1 | NP_009538 | 6319456 | Saccharomyces cerevisiae |

Another hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., J. Biol. Chem. 280:38125-38132 (2005)) and the closest E. coli homolog, tesB, which can also hydrolyze a broad range of CoA thioesters (Naggert et al., J. Biol. Chem. 266:11044-11050 (1991)) including 3-hydroxybutyryl-CoA (Tseng et al., Appl. Environ. Microbiol. 75(10):3137-3145 (2009)). A similar enzyme has also been characterized in the rat liver (Deana, Biochem. Int. 26:767-773 (1992)). Other potential E. coli thioester hydrolases include the gene products of tesA (Bonner and Bloch, J. Biol. Chem. 247:3123-3133 (1972)), ybgC (Kuznetsova et al., FEMS Microbiol. Rev. 29:263-279 (2005); Zhuang et al., FEES Lett. 516:161-163 (2002)), paaI (Song et al., J. Biol. Chem. 281:11028-11038 (2006)), and ybdB (Leduc et al., J. Bacteriol. 189:7112-7126 (2007)). Information related to these proteins and genes is shown below:

| Protein | GenBank ID | GI number | Organism |
| --- | --- | --- | --- |
| Acot8 | CAA15502 | 3191970 | Homo sapiens |
| TesB | NP_414986 | 16128437 | Escherichia coli |
| Acot8 | NP_570112 | 51036669 | Rattus norvegicus |
| TesA | NP_415027 | 16128478 | Escherichia coli |
| YbgC | NP_415264 | 16128711 | Escherichia coli |
| PaaI | NP_415914 | 16129357 | Escherichia coli |
| YbdB | NP_415129 | 16128580 | Escherichia coli |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., J. Biol. Chem. 269:14248-14253 (1994)). Genes encoding this enzyme include hibch of Rattus norvegicus (Shimomura et al., supra (1994); Shimomura et al., Methods Enzymol. 324:229-240 (2000)) and Homo sapiens (Shimomura et al., supra (1994). Candidate genes by sequence homology include hibch of Saccharomyces cerevisiae and BC_2292 of *Bacillus cereus*. BC_2292 was shown to demonstrate 3-hydroxybutyryl-CoA hydrolase activity and function as part of a pathway for 3-hydroxybutyrate synthesis when engineered into *Escherichia coli* (Lee et al., *Appl. Microbiol. Biotechnol.* 79:633-641 (2008)). Information related to these proteins and genes is shown below:

| Protein | GenBank ID | GI number | Organism |
|---|---|---|---|
| Hibch | Q5XIE6.2 | 146324906 | *Rattus norvegicus* |
| Hibch | Q6NVY1.2 | 146324905 | *Homo sapiens* |
| Hibch | P28817.2 | 2506374 | *Saccharomyces cerevisiae* |
| BC_2292 | AP09256 | 29895975 | *Bacillus cereus* ATCC 14579 |

An alternative method for removing the CoA moiety from acetoacetyl-CoA or 3-hydroxybutyryl-CoA is to apply a pair of enzymes such as a phosphate-transferring acyltransferase and a kinase to impart acetoacetyl-CoA or 3-hydroxybutyryl-CoA synthetase activity. This activity enables the net hydrolysis of the CoA-ester of either molecule with the simultaneous generation of ATP. For example, the butyrate kinase (buk)/phosphotransbutyrylase (ptb) system from *Clostridium acetobutylicum* has been successfully applied to remove the CoA group from 3-hydroxybutyryl-CoA when functioning as part of a pathway for 3-hydroxybutyrate synthesis (Tseng et al., *Appl. Environ. Microbiol.* 75(10): 3137-3145 (2009)). Specifically, the ptb gene from *C. acetobutylicum* encodes an enzyme that can convert an acyl-CoA into an acyl-phosphate (Walter et al. *Gene* 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186: 2099-2106 (2004)) and *Bacillus megaterium* (Vazquez et al. *Curr. Microbiol* 42:345-349 (2001)). Additional exemplary phosphate-transferring acyltransferases include phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27.477-492 (199811 Information related to these proteins and genes is shown below.

| Protein | GenBank ID | GI number | Organism |
|---|---|---|---|
| Pta | NP_416800.1 | 16130232 | *Escherichia coli* |
| Ptb | NP_349676 | 15896327 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 ((Walter et al. *Gene* 134(1):107-111 (1993); Huang et al. *J Mol Microbiol Biotechnol* 2(1):33-38 (2000)), and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol* 27:477-492 (1998)). Information related to these proteins and genes is shown below:

| Protein | GenBank ID | GI number | Organism |
|---|---|---|---|
| AckA | NP_416799.1 | 16130231 | *Escherichia coli* |
| Buk1 | NP_349675 | 15896326 | *Clostridium acetobutylicum* |
| Buk2 | Q97II1 | 20137415 | *Clostridium acetobutylicum* |
| ProB | NP_414777.1 | 16128228 | *Escherichia coli* |

The hydrolysis of acetoacetyl-CoA or 3-hydroxybutyryl-CoA can alternatively be carried out by a single enzyme or enzyme complex that exhibits acetoacetyl-CoA or 3-hydroxybutyryl-CoA synthetase activity. This activity enables the net hydrolysis of the CoA-ester of either molecule, and in some cases, results in the simultaneous generation of ATP. For example, the product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Gruys et al., U.S. Pat. No. 5,958,745, filed Sep. 28, 1999). Information related to these proteins and genes is shown below:

| Protein | GenBank ID | GI number | Organism |
|---|---|---|---|
| SucC | NP_415256.1 | 16128703 | *Escherichia coli* |
| SucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

Additional exemplary CoA-ligases include the rat dicarboxylate-CoA ligase for which the sequence is yet uncharacterized (Vamecq et al., *Biochemical J.* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178(14):4122-4130 (1996)). Additional candidate enzymes are acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)), which naturally catalyze the ATP-dependant conversion of acetoacetate into acetoacetyl-CoA. 4-Hydroxybutyryl-CoA synthetase activity has been demonstrated in *Metallosphaera sedula* (Berg et al., *Science* 318:1782-1786 (2007)). This function has been tentatively assigned to the Msed 1422 gene. Information related to these proteins and genes is shown below:

| Protein | GenBank ID | GI number | Organism |
|---|---|---|---|
| Phl | CAJ15517.1 | 77019264 | *Penicillium chrysogenum* |
| PhlB | ABS19624.1 | 152002983 | *Penicillium chrysogenum* |
| PaaF | AAC24333.2 | 22711873 | *Pseudomonas putida* |
| BioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |
| Msed_1422 | YP_001191504 | 146304188 | *Metallosphaera sedula* |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus, H. marismortui* and *P. aerophilum* have all been cloned, functionally expressed, and characterized in *E. coli* (Musfeldt et al., supra; Brasen et al., supra (2004)). Information related to these proteins and genes is shown below:

| Protein | GenBank ID | GI number | Organism |
| --- | --- | --- | --- |
| AF1211 | NP_070039.1 | 11498810 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |

The conversion of 3-hydroxybutyrate to 3-hydroxybutyraldehyde can be carried out by a 3-hydroxybutyrate reductase. Similarly, the conversion of acetoacetate to acetoacetaldehyde can be carried out by an acetoacetate reductase. A suitable enzyme for these transformations is the aryl-aldehyde dehydrogenase, or equivalently a carboxylic acid reductase, from *Nocardia iowensis*. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)). This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)). Information related to these proteins and genes is shown below:

| Protein | GI Number | genbank ID | Organism |
| --- | --- | --- | --- |
| Car | 40796035 | AAR91681.1 | *Nocardia iowensis* (sp. NRRL 5646) |
| Npt | 114848891 | ABI83656.1 | *Nocardia iowensis* (sp. NRRL 5646) |

Additional car and npt genes can be identified based on sequence homology.

| Protein | GENBANK ID | GI Number | Organism |
| --- | --- | --- | --- |
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |
| MSMEG_2956 | YP_887275.1 | 118473501 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | 227979396 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR 665, an enzyme similar in sequence to the *Nocardia iowensis* npt, can be beneficial. Information related to these proteins and genes is shown below:

| Protein | GI number | genbank ID | Organism |
|---|---|---|---|
| griC | 182438036 | YP_001825755.1 | *Streptomyces griseus* subsp. *griseus* NBRC 13350 |
| griD | 182438037 | YP_001825756.1 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date. Information related to these proteins and genes is shown below:

| Protein | GI number | genbank ID | Organism |
|---|---|---|---|
| LYS2 | 171867 | AAA34747.1 | *Saccharomyces cerevisiae* |
| LYS5 | 1708896 | P50113.1 | *Saccharomyces cerevisiae* |
| LYS2 | 2853226 | AAC02241.1 | *Candida albicans* |
| LYS5 | 28136195 | AAO26020.1 | *Candida albicans* |
| Lys1p | 13124791 | P40976.3 | *Schizosaccharomyces pombe* |
| Lys7p | 1723561 | Q10474.1 | *Schizosaccharomyces pombe* |
| Lys2 | 3282044 | CAA74300.1 | *Penicillium chrysogenum* |

Any of these CAR or CAR-like enzymes can exhibit 3-hydroxybutyrate or acetoacetate reductase activity or can be engineered to do so.

The requisite 3-hydroxybutyrate dehydrogenase catalyzes the reduction of acetoacetate to form 3-hydroxybutyrate. Exemplary enzymes can be found in *Rhodococcus ruber* (Kosjek et al., *Biotechnol Bioeng.* 86:55-62 (2004)) and *Pyrococcus furiosus* (van der et al., *Eur. J. Biochem.* 268:3062-3068 (2001)). Additional secondary alcohol dehydrogenase enzymes capable of this transformation include adh from *C. beijerinckii* (Hanai et al., *Appl Environ Microbiol* 73:7814-7818 (2007); Jojima et al., *Appl Microbiol Biotechnol* 77:1219-1224 (2008)) and adh from *Thermoanaerobacter brockii* (Hanai et al., *Appl Environ Microbiol* 73:7814-7818 (2007); Peretz et al., *Anaerobe* 3:259-270 (1997)). The cloning of the bdhA gene from *Rhizobium (Sinorhizobium) Meliloti* into *E. coli* conferred the ability to utilize 3-hydroxybutyrate as a carbon source (Aneja and Charles, *J. Bacteriol.* 181(3):849-857 (1999)). Additional 3-hydroxybutyrate dehydrogenase can be found in *Pseudomonas fragi* (Ito et al., *J. Mol. Biol.* 355(4) 722-733 (2006)) and *Ralstonia pickettii* (Takanashi et al., *Antonie van Leeuwenoek*, 95(3):249-262 (2009)). Information related to these proteins and genes is shown below:

| Protein | Genbank ID | GI Number | Organism |
|---|---|---|---|
| Sadh | CAD36475 | 21615553 | *Rhodococcus ruber* |
| AdhA | AAC25556 | 3288810 | *Pyrococcus furiosus* |
| Adh | P14941.1 | 113443 | *Thermoanaerobobacter brockii* |
| Adh | AAA23199.2 | 60592974 | *Clostridium beijerinckii* |
| BdhA | NP_437676.1 | 16264884 | *Rhizobium (Sinorhizobium) Meliloti* |
| PRK13394 | BAD86668.1 | 57506672 | *Pseudomonas fragi* |
| Bdh1 | BAE72684.1 | 84570594 | *Ralstonia pickettii* |
| Bdh2 | BAE72685.1 | 84570596 | *Ralstonia pickettii* |
| Bdh3 | BAF91602.1 | 158937170 | *Ralstonia pickettii* |

Example II

Isopropanol Synthesis Pathway

This Example shows how isopropanol production was achieved in recombinant *E. coli* following expression of two heterologous genes from *C. acetobutylicum* (thl and adc encoding acetoacetyl-CoA thiolase and acetoacetate decarboxylase, respectively) and one from *C. beijerinckii* (adh encoding a secondary alcohol dehydrogenase), along with the increased expression of the native atoA and atoD genes which encode acetoacetyl-CoA: acetate: CoA transferase activity (Hanai et al., *Appl. Environ. Microbiol.* 73:7814-7818 (2007)). The acetoacetyl-CoA thiolase (AtoB) enzymes are described herein above.

The conversion of acetoacetyl-CoA to acetoacetate or of 4-hydroxybutyryl-CoA to 4-hydroxybutyrate can be carried out by an acetoacetyl-CoA transferase or 4-hydroxybutyryl-CoA transferase, respectively. These enzymes conserve the energy stored in the CoA-ester bonds of acetoacetyl-CoA and 4-hydroxybutyryl-CoA. Many transferases have broad specificity and thus may utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. Acetoacetyl-CoA transferase catalyzes the conversion of acetoacetyl-CoA to acetoacetate while transferring the CoA moiety to a CoA acceptor molecule. Several exemplary transferase enzymes capable of catalyzing this transformation are provided below. These enzymes either naturally exhibit the desired acetoacetyl-CoA transferase activity or they can be engineered via directed evolution to accept acetoacetyl-CoA as a substrate with increased efficiency. Such enzymes, either naturally or following directed evolution, are also suitable for catalyzing the conversion of 4-hydroxybutyryl-CoA to 4-hydroxybutyrate via a transferase mechanism.

In one embodiment an exemplary acetoacetyl-CoA transferase is acetoacetyl-CoA:acetate-CoA transferase. This enzyme naturally converts acetate to acetyl-CoA while converting acetoacetyl-CoA to acetoacetate. In another embodiment, a succinyl-CoA:3-ketoacid CoA transferase (SCOT) catalyzes the conversion of the 3-ketoacyl-CoA, acetoacetyl-CoA, to the 3-ketoacid, acetoacetate.

Acetoacetyl-CoA:acetyl-CoA transferase naturally converts acetoacetyl-CoA and acetate to acetoacetate and acetyl-CoA. This enzyme can also accept 3-hydroxybutyryl-CoA as a substrate or could be engineered to do so. Exemplary enzymes include the gene products of atoAD from *E. coli* (Hanai et al., *Appl Environ Microbiol* 73:7814-7818 (2007)), ctfAB from *C. acetobutylicum* (Jojima et al., *Appl Microbiol Biotechnol* 77:1219-1224 (2008)), and ctfAB from *Clostridium saccharoperbutylacetonicum* (Kosaka et al., *Biosci. Biotechnol Biochem.* 71:58-68 (2007)). Information related to these proteins and genes is shown below:

| Protein | GENBANK ID | GI NUMBER | ORGANISM |
|---|---|---|---|
| AtoA | P76459.1 | 2492994 | *Escherichia coli* |
| AtoD | P76458.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Succinyl-CoA:3-ketoacid-CoA transferase naturally converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., *Genomics* 68:144-151 (2000); Tanaka et al., *Mol. Hum. Reprod.* 8:16-23 (2002)). Information related to these proteins and genes is shown below:

| Protein | GENBANK ID | GI NUMBER | ORGANISM |
|---|---|---|---|
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Additional suitable acetoacetyl-CoA and 4-hydroxybutyryl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA transferase activity, respectively (Seedorf et al., *Proc. Natl. Acad. Sci. USA* 105:2128-2133 (2008); Sohling and Gottschalk, *J. Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA: acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenborn et al., *Appl. Environ. Microbiol.* 55(2):323-9 (1989)). Although specific gene sequences were not provided for butyryl-CoA:acetoacetate CoA-transferase in these references, the genes FNO272 and FNO273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyromonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below:

| Protein | GENBANK ID | GI NUMBER | ORGANISM |
|---|---|---|---|
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Acetoacetyl-CoA can be hydrolyzed to acetoacetate by acetoacetyl-CoA hydrolase. Similarly, 4-hydroxybutyryl-CoA can be hydrolyzed to 4-hydroxybutyate by 4-hydroxybutyryl-CoA hydrolase. Many CoA hydrolases (EC 3.1.2.1) have broad substrate specificity and are suitable enzymes for these transformations either naturally or following enzyme engineering. Though the sequences were not reported, several acetoacetyl-CoA hydrolases were identified in the cytosol and mitochondrion of the rat liver (Aragon and Lowenstein, *J. Biol. Chem.* 258(8):4725-4733 (1983)). Additionally, an enzyme from *Rattus norvegicus* brain (Robinson et al., *Biochem. Biophys. Res. Commun.* 71:959-965 (1976)) can react with butyryl-CoA, hexanoyl-CoA and malonyl-CoA. The acot12 enzyme from the rat liver was shown to hydrolyze C2 to C6 acyl-CoA molecules (Suematsu et al., *Eur. J. Biochem.* 268:2700-2709 (2001)). Though its sequence has not been reported, the enzyme from the mitochondrion of the pea leaf showed activity on acetyl-CoA, propionyl-CoA, butyryl-CoA, palmitoyl-CoA, oleoyl-CoA, succinyl-CoA, and crotonyl-CoA (Zeiher and Randall, *Plant. Physiol.* 94:20-27 (1990)). Additionally, a glutaconate CoA-transferase from *Acidaminococcus fermentans* was transformed by site-directed mutagenesis into an acyl-CoA hydrolase with activity on glutaryl-CoA, acetyl-CoA and 3-butenoyl-CoA (Mack and Buckel, *FEBS Lett.* 405:209-212 (1997)). This indicates that the enzymes encoding acetoacetyl-CoA transferases and 4-hydroxybutyryl-CoA transferases can also be used as hydrolases with certain mutations to change their function. The acetyl-CoA hydrolase, ACH1, from *S. cerevisiae* represents another candidate hydrolase (Buu et al., *J. Biol. Chem.* 278:17203-17209 (2003)). Information related to these proteins and genes is shown below:

| Protein | GENBANK ID | GI NUMBER | ORGANISM |
| --- | --- | --- | --- |
| Acot12 | NP_570103.1 | 18543355 | Rattus norvegicus |
| GctA | CAA57199 | 559392 | Acidaminococcus fermentans |
| GctB | CAA57200 | 559393 | Acidaminococcus fermentans |
| ACH1 | NP_009538 | 6319456 | Saccharomyces cerevisiae |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., J. Biol. Chem. 280:38125-38132 (2005)) and the closest E. coli homolog, tesB, which can also hydrolyze a broad range of CoA thioesters (Naggert et al., J. Biol. Chem. 266:11044-11050 (1991)) including 3-hydroxybutyryl-CoA (Tseng et al., Appl. Environ. Microbiol. 75(10):3137-3145 (2009)). A similar enzyme has also been characterized in the rat liver (Deana, Biochem. Int. 26:767-773 (1992)). Other potential E. coli thioester hydrolases include the gene products of tesA (Bonner and Bloch, J. Biol. Chem. 247:3123-3133 (1972)), ybgC (Kuznetsova et al., FEMS Microbiol. Rev. 29:263-279 (2005); Zhuang et al., FEBS Lett. 516:161-163 (2002)), paaI (Song et al., J. Biol. Chem. 281:11028-11038 (2006)), and ybdB (Leduc et al., J. Bacteriol. 189:7112-7126 (2007)). Information related to these proteins and genes is shown below:

| Protein | GENBANK ID | GI NUMBER | ORGANISM |
| --- | --- | --- | --- |
| Acot8 | CAA15502 | 3191970 | Homo sapiens |
| TesB | NP_414986 | 16128437 | Escherichia coli |
| Acot8 | NP_570112 | 51036669 | Rattus norvegicus |
| TesA | NP_415027 | 16128478 | Escherichia coli |
| YbgC | NP_415264 | 16128711 | Escherichia coli |
| PaaI | NP_415914 | 16129357 | Escherichia coli |
| YbdB | NP_415129 | 16128580 | Escherichia coli |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., J. Biol. Chem. 269:14248-14253 (1994)). Genes encoding this enzyme include hibch of Rattus norvegicus (Shimomura et al., supra (1994); Shimomura et al., Methods Enzymol. 324:229-240 (2000)) and Homo sapiens (Shimomura et al., supra (1994). Candidate genes by sequence homology include hibch of Saccharomyces cerevisiae and BC_2292 of Bacillus cereus. BC_2292 was shown to demonstrate 3-hydroxybutyryl-CoA hydrolase activity and function as part of a pathway for 3-hydroxybutyrate synthesis when engineered into Escherichia coli (Lee et al., Appl. Microbiol. Biotechnol. 79:633-641 (2008)). Information related to these proteins and genes is shown below:

| Protein | GENBANK ID | GI NUMBER | ORGANISM |
| --- | --- | --- | --- |
| Hibch | Q5XIE6.2 | 146324906 | Rattus norvegicus |
| Hibch | Q6NVY1.2 | 146324905 | Homo sapiens |
| Hibch | P28817.2 | 2506374 | Saccharomyces cerevisiae |
| BC_2292 | AP09256 | 29895975 | Bacillus cereus ATCC 14579 |

The hydrolysis of acetoacetyl-CoA or 4-hydroxybutyryl-CoA can alternatively be carried out by a single enzyme or enzyme complex that exhibits acetoacetyl-CoA or 4-hydroxybutyryl-CoA synthetase activity. This activity enables the net hydrolysis of the CoA-ester of either molecule, and in some cases, results in the simultaneous generation of ATP. For example, the product of the LSC1 and LSC2 genes of S. cerevisiae and the sucC and sucD genes of E. coli naturally form a succinyl-CoA synthetase complex that catalyzes the formation of succinyl-CoA from succinate with the concomitant consumption of one ATP, a reaction which is reversible in vivo (Gruys et al., U.S. Pat. No. 5,958,745, filed Sep. 28, 1999). Information related to these proteins and genes is shown below:

| Protein | GENBANK ID | GI NUMBER | ORGANISM |
| --- | --- | --- | --- |
| SucC | NP_415256.1 | 16128703 | Escherichia coli |
| SucD | AAC73823.1 | 1786949 | Escherichia coli |
| LSC1 | NP_014785 | 6324716 | Saccharomyces cerevisiae |
| LSC2 | NP_011760 | 6321683 | Saccharomyces cerevisiae |

Additional exemplary CoA-ligases include the rat dicarboxylate-CoA ligase for which the sequence is yet uncharacterized (Vamecq et al., Biochemical J. 230:683-693 (1985)), either of the two characterized phenylacetate-CoA ligases from P. chrysogenum (Lamas-Maceiras et al., Biochem. J. 395:147-155 (2005); Wang et al., Biochem Biophy Res Commun 360(2):453-458 (2007)), the phenylacetate-CoA ligase from Pseudomonas putida (Martinez-Blanco et al., J. Biol. Chem. 265:7084-7090 (1990)), and the 6-carboxyhexanoate-CoA ligase from Bacillus subtilis (Bower et al., J. Bacteriol. 178(14):4122-4130 (1996)). Additional candidate enzymes are acetoacetyl-CoA synthetases from Mus musculus (Hasegawa et al., Biochim. Biophys. Acta 1779:414-419 (2008)) and Homo sapiens (Ohgami et al., Biochem. Pharmacol. 65:989-994 (2003)), which naturally catalyze the ATP-dependant conversion of acetoacetate into acetoacetyl-CoA. 4-Hydroxybutyryl-CoA synthetase activity has been demonstrated in Metallosphaera sedula (Berg et al., Science 318:1782-1786 (2007)). This function has been tentatively assigned to the Msed 1422 gene. Information related to these proteins and genes is shown below:

| Protein | GENBANK ID | GI NUMBER | ORGANISM |
| --- | --- | --- | --- |
| Phl | CAJ15517.1 | 77019264 | Penicillium chrysogenum |
| PhlB | ABS19624.1 | 152002983 | Penicillium chrysogenum |
| PaaF | AAC24333.2 | 22711873 | Pseudomonas putida |
| BioW | NP_390902.2 | 50812281 | Bacillus subtilis |
| AACS | NP_084486.1 | 21313520 | Mus musculus |
| AACS | NP_076417.2 | 31982927 | Homo sapiens |
| Msed_1422 | YP_001191504 | 146304188 | Metallosphaera sedula |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from Archaeoglobus fulgidus, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., J. Bacteriol. 184:636-644 (2002)). The enzyme from Haloarcula marismortui (annotated as a succinyl-CoA synthetase) accepts propionate, butyrate, and branched-chain acids (isovalerate and isobutyrate) as substrates, and was shown to operate in the forward and reverse directions (Brasen et al., Arch. Microbiol. 182:277-287 (2004)). The ACD encoded by PAE3250 from hyperthermophilic crenarchaeon Pyrobaculum aerophilum showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus, H. marismortui* and *P. aerophilum* have all been cloned, functionally expressed, and characterized in *E. coli* (Musfeldt et al., supra; Brasen et al., supra (2004)). Information related to these proteins and genes is shown below:

| Protein | GENBANK ID | GI NUMBER | ORGANISM |
|---|---|---|---|
| AF1211 | NP_070039.1 | 11498810 | *Archaeoglobus fulgidus* DSM 4304 |
| Scs | YP_135572.1 | 55377722 | *Haloarcula marismortui* ATCC 43049 |
| PAE3250 | NP_560604.1 | 18313937 | *Pyrobaculum aerophilum* str. IM2 |

An alternative method for removing the CoA moiety from acetoacetyl-CoA or 4-hydroxybutyryl-CoA is to apply a pair of enzymes such as a phosphate-transferring acyltransferase and a kinase to impart acetoacetyl-CoA or 4-hydroxybutyryl-CoA synthetase activity. Exemplary names for these enzymes include phosphotrans-4-hydroxybutyrylase/4-hydroxybutyrate kinase, which can remove the CoA moiety from 4-hydroxybutyryl-CoA, and phosphotransacetoacetylase/acetoacetate kinase which can remove the CoA moiety from acetoacetyl-CoA. This general activity enables the net hydrolysis of the CoA-ester of either molecule with the simultaneous generation of ATP. For example, the butyrate kinase (buk)/phosphotransbutyrylase (ptb) system from *Clostridium acetobutylicum* has been successfully applied to remove the CoA group from 3-hydroxybutyryl-CoA when functioning as part of a pathway for 3-hydroxybutyrate synthesis (Tseng et al., *Appl. Environ. Microbiol.* 75(10): 3137-3145 (2009)). Specifically, the ptb gene from *C. acetobutylicum* encodes an enzyme that can convert an acyl-CoA into an acyl-phosphate (Walter et al. *Gene* 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186: 2099-2106 (2004)) and *Bacillus megaterium* (Vazquez et al. *Curr. Microbiol* 42:345-349 (2001)). Additional exemplary phosphate-transferring acyltransferases include phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Information related to these proteins and genes is shown below:

| Protein | GENBANK ID | GI NUMBER | ORGANISM |
|---|---|---|---|
| Pta | NP_416800.1 | 16130232 | *Escherichia coli* |
| Ptb | NP_349676 | 15896327 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 ((Walter et al. *Gene* 134(1):107-111 (1993); Huang et al. *J Mol Microbiol Biotechnol* 2(1):33-38 (2000)), and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol* 27:477-492 (1998)). Information related to these proteins and genes is shown below:

| Protein | GENBANK ID | GI NUMBER | ORGANISM |
|---|---|---|---|
| AckA | NP_416799.1 | 16130231 | *Escherichia coli* |
| Buk1 | NP_349675 | 15896326 | *Clostridium acetobutylicum* |
| Buk2 | Q97II1 | 20137415 | *Clostridium acetobutylicum* |
| ProB | NP_414777.1 | 16128228 | *Escherichia coli* |

Acetoacetate decarboxylase converts acetoacetate into carbon dioxide and acetone. Exemplary acetoacetate decarboxylase enzymes are encoded by the gene products of adc from *C. acetobutylicum* (Petersen and Bennett, *Appl. Environ. Microbiol.* 56:3491-3498 (1990) and adc from *Clostridium saccharoperbutylacetonicum* (Kosaka et al., *Biosci. Biotechnol. Biochem.* 71:58-68 (2007)). The enzyme from *C. beijerinkii* can be inferred from sequence similarity.

| Protein | GenBank ID | GI Number | Organism |
|---|---|---|---|
| Adc | NP_149328.1 | 15004868 | *Clostridium acetobutylicum* |
| Adc | AAP42566.1 | 31075386 | *Clostridium saccharoperbutylacetonicum* |
| Adc | YP_001310906.1 | 150018652 | *Clostridium beijerinckii* |

The final step in the isopropanol synthesis pathway involves the reduction of acetone to isopropanol. Exemplary alcohol dehydrogenase enzymes capable of this transformation include adh from *C. beijerinckii* (Jojima et al., *Appl. Microbiol. Biotechnol.* 77:1219-1224 (2008); Hanai et al., *Appl. Environ. Microbiol.* 73:7814-7818 (2007) and adh from *Thermoanaerobacter* brockii (Hanai et al., supra; Peretz et al., *Anaerobe* 3:259-270 (1997)). Additional characterized enzymes include alcohol dehydrogenases from *Ralstonia eutropha* (formerly *Alcaligenes eutrophus*) (Steinbuchel and Schlegel, *Eur. J. Biochem.* 141:555-564 (1984) and *Phytomonas* species (Uttaro and Opperdoes, *Mol. Biochen. Parasitol.* 85: 213-219 (1997)).

| Protein | GenBank ID | GI Number | Organism |
|---|---|---|---|
| Adh | P14941.1 | 113443 | *Thermoanaerobobacter brockii* |
| Adh | AAA23199.2 | 60592974 | *Clostridium beijerinckii* |
| Adh | YP_299391.1 | 73539024 | *Ralstonia eutropha* |
| iPDH | AAP39869.1 | 31322946 | *Phtomonas* sp. |

Example III

4-Hydroxybutyrate Synthesis Pathway

This Example shows further enzymes that can be used in a 4-hydroxybutyrate pathway. The genes for the first enzyme, acetoacetyl-CoA thiolase are described herein above.

Exemplary 3-hydroxyacyl dehydrogenases which convert acetoacetyl-CoA to 3-hydroxybutyryl-CoA include hbd from *C. acetobutylicum* (Boynton et al., *J. Bacteriol.* 178: 3015-3024 (1996), hbd from *C. beijerinckii* (Colby and Chen, *Appl. Environ. Microbiol.* 58:3297-3302 (1992), and a number of similar enzymes from *Metallosphaera sedula* (Berg et al., *Science* 318:1782-1786 (2007)).

| Protein | GenBank ID | GI Number | Organism |
|---|---|---|---|
| hbd | NP_349314.1 | 15895965 | *Clostridium acetobutylicum* |
| hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |

The gene product of crt from *C. acetobutylicum* catalyzes the dehydration of 3-hydroxybutyryl-CoA to crotonyl-CoA (Boynton et al., *J. Bacteriol.* 178:3015-3024 (1996); Atsumi et al., *Metab. Eng.* (2007)). Further, enoyl-CoA hydratases are reversible enzymes and thus suitable candidates for catalyzing the dehydration of 3-hydroxybutyryl-CoA to crotonyl-CoA. The enoyl-CoA hydratases, phaA and phaB, of *P. putida* are believed to carry out the hydroxylation of double bonds during phenylacetate catabolism (Olivera et al., *Proc. Nat. Acad. Sci. U.S.A.* 95:6419-6424 (1998)). The paaA and paaB from *P. fluorescens* catalyze analogous transformations (Olivera et al., supra). Lastly, a number of *Escherichia coli* genes have been shown to demonstrate enoyl-CoA hydratase functionality including maoC, paaF, and paaG (Park and Lee, *J. Bacteriol.* 185:5391-5397 (2003); Park and Lee, *Appl. Biochem. Biotechnol.* 113-116: 335-346 (2004); Park and Yup, *Biotechnol. Bioeng.* 86:681-686 (2004); Ismail et al., *J. Bacteriol.* 175:5097-5105 (2003)).

| Protein | GenBank ID | GI Number | Organism |
|---|---|---|---|
| crt | NP_349318.1 | 15895969 | *Clostridium acetobutylicum* |
| paaA | NP_745427.1 | 26990002 | *Pseudomonas putida* |
| paaB | NP_745426.1 | 26990001 | *Pseudomonas putida* |
| phaA | ABF82233.1 | 106636093 | *Pseudomonas fluorescens* |
| phaB | ABF82234.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Several enzymes that naturally catalyze the reverse reaction (i.e., the dehydration of 4-hydroxybutyryl-CoA to crotonoyl-CoA) in vivo have been identified in numerous species. This transformation is required for 4-aminobutyrate fermentation by *Clostridium aminobutyricum* (Scherf and Buckel, *Eur. J. Biochem.* 215:421-429 (1993) and succinate-ethanol fermentation by *Clostridium kluyveri* (Scherf et al., *Arch. Microbiol.* 161:239-245 (1994)). The transformation is also a key step in Archaea, for example, *Metallosphaera sedula*, as part of the 3-hydroxypropionate/4-hydroxybutyrate autotrophic carbon dioxide assimilation pathway (Berg et al., *Science* 318:1782-1786 (2007)). This pathway requires the hydration of crotonoyl-CoA to form 4-hydroxybutyryl-CoA. The reversibility of 4-hydroxybutyryl-CoA dehydratase is well-documented (Muh et al., *Biochemistry* 35:11710-11718 (1996); Friedrich et al., *Agnew Chem. Int. Ed. Engl.* 47:3254-3257 (2008); Muh et al., *Eur. J. Biochem.* 248:380-384 (1997) and the equilibrium constant has been reported to be about 4 on the side of crotonyl-CoA (Scherf and Buckel, *Eur. J. Biochem.* 215:421-429 (1993). This implies that the downstream 4-hydroxybutyryl-CoA dehydrogenase must keep the 4-hydroxybutyryl-CoA concentration low so as to not create a thermodynamic bottleneck at crotonyl-CoA. The reverse reaction of 4-hydroxybutyryl-CoA dehydratase is crotonyl-CoA hydratase.

| Protein | GenBank ID | GI Number | Organism |
|---|---|---|---|
| AbfD | CAB60035 | 70910046 | *Clostridium aminobutyricum* |
| AbfD | YP_001396399 | 153955634 | *Clostridium kluyveri* |
| Msed_1321 | YP_001191403 | 146304087 | *Metallosphaera sedula* |
| Msed_1220 | YP_001191305 | 146303989 | *Metallosphaera sedula* |

Suitable acetoacetyl-CoA and 4-hydroxybutyryl-CoA transferases are encoded by the gene products of cat1, cat2, and cat3 of *Clostridium kluyveri*. These enzymes have been shown to exhibit succinyl-CoA, 4-hydroxybutyryl-CoA, and butyryl-CoA transferase activity, respectively (Seedorf et al., *Proc. Natl. Acad. Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA: acetoacetate CoA-transferase. Exemplary enzymes can be found in *Fusobacterium nucleatum* (Barker et al., *J. Bacteriol.* 152 (1):201-7 (1982)), *Clostridium* SB4 (Barker et al., *J. Biol. Chem.* 253(4):1219-25 (1978)), and *Clostridium acetobutylicum* (Wiesenborn et al., *Appl. Environ. Microbiol.* 55(2): 323-9 (1989)). Although specific gene sequences were not provided for butyryl-CoA:acetoacetate CoA-transferase in these references, the genes FNO272 and FNO273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyrmonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below.

| Protein | GENBANK ID | GI NUMBER | ORGANISM |
|---|---|---|---|
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

An alternative method for removing the CoA moiety from acetoacetyl-CoA or 4-hydroxybutyryl-CoA is to apply a pair of enzymes such as a phosphate-transferring acyltransferase and a kinase to impart acetoacetyl-CoA or 4-hydroxybutyryl-CoA synthetase activity. Exemplary names for these enzymes include phosphotrans-4-hydroxybutyrylase/4-hydroxybutyrate kinase, which can remove the CoA moiety from 4-hydroxybutyryl-CoA, and phosphotransacetoacetylase/acetoacetate kinase which can remove the CoA moiety from acetoacetyl-CoA. This general activity enables the net hydrolysis of the CoA-ester of either molecule with the simultaneous generation of ATP. For example, the butyrate kinase (buk)/phosphotransbutyrylase (ptb) system from *Clostridium acetobutylicum* has been successfully applied to remove the CoA group from 3-hydroxybutyryl-CoA when functioning as part of a pathway for 3-hydroxybutyrate synthesis (Tseng et al., *Appl. Environ. Microbiol.* 75(10): 3137-3145 (2009)). Specifically, the ptb gene from *C. acetobutylicum* encodes an enzyme that can convert an acyl-CoA into an acyl-phosphate (Walter et al. *Gene* 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186: 2099-2106 (2004)) and *Bacillus megaterium* (Vazquez et al. *Curr. Microbiol* 42:345-349 (2001)). Additional exemplary phosphate-transferring acyltransferases include phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Information related to these proteins and genes is shown below.

| Protein | GENBANK ID | GI NUMBER | ORGANISM |
| --- | --- | --- | --- |
| Pta | NP_416800.1 | 16130232 | *Escherichia coli* |
| Ptb | NP_349676 | 15896327 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 ((Walter et al. *Gene* 134(1):107-111 (1993); Huang et al. *J Mol Microbiol Biotechnol* 2(1):33-38 (2000)), and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol* 27:477-492 (1998)). Information related to these proteins and genes is shown below:

| Protein | GENBANK ID | GI NUMBER | ORGANISM |
| --- | --- | --- | --- |
| AckA | NP_416799.1 | 16130231 | *Escherichia coli* |
| Buk1 | NP_349675 | 15896326 | *Clostridium acetobutylicum* |
| Buk2 | Q97II1 | 20137415 | *Clostridium acetobutylicum* |
| ProB | NP_414777.1 | 16128228 | *Escherichia coli* |

Example IV 1,4-Butanediol Synthesis Pathway

This Example shows further enzymes that can be used in a 1,4-butanediol pathway. The genes for acetoacetyl-CoA thiolase, 3-Hydroxybutyryl-CoA dehydrogenase (Hbd), Crotonase (Crt), and Crotonyl-CoA hydratase (4-Budh) are described herein above.

Alcohol-forming 4-hydroxybutyryl-CoA reductase enzymes catalyze the 2 reduction steps required to form 1,4-butanediol from 4-hydroxybutyryl-CoA. Exemplary 2-step oxidoreductases that convert an acyl-CoA to alcohol include those that transform substrates such as acetyl-CoA to ethanol (e.g., adhE from *E. coli* (Kessler et al., *FEBS Lett.* 281:59-63 (1991)) and butyryl-CoA to butanol (e.g. adhE2 from *C. acetobutylicum* (Fontaine et al., *J. Bacteriol.* 184: 821-830 (2002)). The adhE2 enzyme from *C. acetobutylicum* was specifically shown in ref. (WO/2008/115840 (2008)) to produce BDO from 4-hydroxybutyryl-CoA. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972; Koo et al., *Biotechnol. Lett.* 27:505-510 (2005)).

| Protein | GenBank ID | GI Number | Organism |
| --- | --- | --- | --- |
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2002); Strauss and Fuchs, *Eur. J. Biochem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity.

| Protein | GenBank ID | GI Number | Organism |
| --- | --- | --- | --- |
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

An alternative route to BDO from 4-hydroxybutyryl-CoA involves first reducing this compound to 4-hydroxybutanal. Several acyl-CoA dehydrogenases are capable of reducing an acyl-CoA to its corresponding aldehyde. Exemplary genes that encode such enzymes include the *Acinetobacter* calcoaceticus acyl encoding a fatty acyl-CoA reductase (Reiser and Somerville, J. Bacteriol. 179:2969-2975 (1997), the Acinetobacter sp. M-1 fatty acyl-CoA reductase (Ishige et al., Appl. Environ. Microbiol. 68:1192-1195 (2002), and a CoA- and NADP-dependent succinate semialdehyde dehydrogenase encoded by the sucD gene in Clostridium kluyveri (Sohling and Gottschalk, J. Bacteriol. 178:871-880 (1996); Sohling and Gottschalk, J. Bacteriol. 178:8710880 (1996)). SucD of P. gingivalis is another succinate semialdehyde dehydrogenase (Takahashi et al., J. Bacteriol. 182:4704-4710 (2000)). These succinate semialdehyde dehydrogenases were specifically shown in ref. (WO/2008/115840 (2008)) to convert 4-hydroxybutyryl-CoA to 4-hydroxybutanal as part of a pathway to produce 1,4-butanediol. The enzyme acylating acetaldehyde dehydrogenase in Pseudomonas sp, encoded by bphG, is yet another capable enzyme as it has been demonstrated to oxidize and acylate acetaldehyde, propionaldehyde, butyraldehyde, isobutyraldehyde and formaldehyde (Powlowski et al., J. Bacteriol. 175:377-385 (1993)).

| Protein | GenBank ID | GI Number | Organism |
| --- | --- | --- | --- |
| acr1 | YP_047869.1 | 50086359 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., Science 318:1782-1786 (2007); Thauer, Science 318:1732-1733 (2007)). The enzyme utilizes NADPH as a cofactor and has been characterized in Metallosphaera and Sulfolobus spp (Alber et al., J. Bacteriol. 188:8551-8559 (2006); Hugler et al., J. Bacteriol. 184:2404-2410 (2002)). The enzyme is encoded by Msed 0709 in Metallosphaera sedula (Alber et al. Mol. Microbiol. 61:297-309 (2006); Berg et al., Science 318: 1782-1786 (2007)). A gene encoding a malonyl-CoA reductase from Sulfolobus tokodaii was cloned and heterologously expressed in E. coli (Alber et al., J. Bacteriol. 188:8551-8559 (2006)). Although the aldehyde dehydrogenase functionality of these enzymes is similar to the bifunctional dehydrogenase from Chloroflexus aurantiacus, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including Sulfolobus solfataricus and Sulfolobus acidocaldarius. Yet another candidate for CoA-acylating aldehyde dehydrogenase is the ald gene from Clostridium beijerinckii (Toth, Appl. Environ. Microbiol. 65:4973-4980 (1999). This enzyme has been reported to reduce acetyl-CoA and butyryl-CoA to their corresponding aldehydes. This gene is very similar to eutE that encodes acetaldehyde dehydrogenase of Salmonella typhimurium and E. coli (Toth, Appl. Environ. Microbiol. 65:4973-4980 (1999). These proteins are identified below.

| Protein | GenBank ID | GI Number | Organism |
| --- | --- | --- | --- |
| Msed_0709 | YP_001190808.1 | 146303492 | Metallosphaera sedula |
| Mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 49473535 | Clostridium beijerinckii |
| eutE | AAA80209 | 687645 | Salmonella typhimurium |
| eutE | P77445 | 2498347 | Escherichia coli |

4-Hydroxybutyryl-CoA can also be converted to 4-hydroxybutanal in several enzymatic steps, though the intermediate 4-hydroxybutyrate. First, 4-hydroxybutyryl-CoA can be converted to 4-hydroxybutyrate by a CoA transferase, hydrolase or synthetase. Alternately, 4-hydroxybutyryl-CoA can be converted to 4-hydroxybutyrate via a phosphonated intermediate by enzymes with phosphotrans-4-hydroxybutyrylase and 4-hydroxybutyrate kinase. Exemplary candidates for these enzymes are described above.

Subsequent conversion of 4-hydroxybutyrate to 4-hydroxybutanal is catalyzed by an aryl-aldehyde dehydrogenase, or equivalently a carboxylic acid reductase. Such an enzyme is found in Nocardia iowensis. Carboxylic acid reductase catalyzes the magnesium, ATP and NADPH-dependent reduction of carboxylic acids to their corresponding aldehydes (Venkitasubramanian et al., J. Biol. Chem. 282:478-485 (2007)) and is capable of catalyzing the conversion of 4-hydroxybutyrate to 4-hydroxybutanal. This enzyme, encoded by car, was cloned and functionally expressed in E. coli (Venkitasubramanian et al., J. Biol. Chem. 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in Biocatalysis in the Pharmaceutical and Biotechnology Industires, ed. R. N. Patel, Chapter 15, pp. 425-440, CRC Press LLC, Boca Raton, Fla. (2006)).

| Gene name | GI Number | GenBank ID | Organism |
| --- | --- | --- | --- |
| Car | 40796035 | AAR91681.1 | Nocardia iowensis (sp. NRRL 5646) |
| Npt | 114848891 | ABI83656.1 | Nocardia iowensis (sp. NRRL 5646) |

Additional car and npt genes can be identified based on sequence homology.

| Gene name | GI Number | GenBank ID | Organism |
| --- | --- | --- | --- |
| fadD9 | 121638475 | YP_978699.1 | Mycobacterium bovis BCG |
| BCG_2812c | 121638674 | YP_978898.1 | Mycobacterium bovis BCG |
| nfa20150 | 54023983 | YP_118225.1 | Nocardia farcinica IFM 10152 |

| Gene name | GI Number | GenBank ID | Organism |
|---|---|---|---|
| nfa40540 | 54026024 | YP_120266.1 | *Nocardia farcinica* IFM 10152 |
| SGR_6790 | 182440583 | YP_001828302.1 | *Streptomyces griseus* subsp. *griseus* NBRC 13350 |
| SGR_665 | 182434458 | YP_001822177.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | ZP_04026660.1 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR 665, an enzyme similar in sequence to the *Nocardia iowensis* npt, can be beneficial.

| Gene name | GI Number | GenBank ID | Organism |
|---|---|---|---|
| griC | 182438036 | YP_001825755.1 | *Streptomyces griseus* subsp. *griseus* NBRC 13350 |
| Grid | 182438037 | YP_001825756.1 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Gene name | GI Number | GenBank ID | Organism |
|---|---|---|---|
| LYS2 | 171867 | AAA34747.1 | *Saccharomyces cerevisiae* |
| LYS5 | 1708896 | P50113.1 | *Saccharomyces cerevisiae* |
| LYS2 | 2853226 | AAC02241.1 | *Candida albicans* |
| LYS5 | 28136195 | AAO26020.1 | *Candida albicans* |
| Lys1p | 13124791 | P40976.3 | *Schizosaccharomyces pombe* |
| Lys7p | 1723561 | Q10474.1 | *Schizosaccharomyces pombe* |
| Lys2 | 3282044 | CAA74300.1 | *Penicillium chrysogenum* |

Enzymes exhibiting 1,4-butanediol dehydrogenase activity are capable of forming 1,4-butanediol from 4-hydroxybutanal. Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani *Appl. Environ. Micro et al.* 66:5231-5235 (2000), ADH2 from *Saccharomyces cerevisiae* (Aoshima et al., *Mol. Microbiol.* 51:791-798 (2004)), yqhD from *E. coli* which has preference for molecules longer than C(3) (Sulzenbacher et al., *J. Mol. Biol.* 342:489-502 (2004), and bdh I and bdh II from *C. acetobutylicum* which converts butyraldehyde into butanol (Walter et al., *J. Bacteriol.* 174:7149-7158 (1992)). ADH1 from *Zymomonas mobilis* has been demonstrated to have activity on a number of aldehydes including formaldehyde, acetaldehyde, propionaldehyde, butyraldehyde, and acrolein (Kinoshita, *Appl. Microbiol. Biotechnol.* 22:249-254 (1985)).

| Protein | GenBank ID | GI Number | Organism |
|---|---|---|---|
| alrA | BAB12273.1 | 9967138 | *Acinetobacter* sp. Strain M-1 |
| ADH2 | NP_014032.1 | 6323961 | *Saccharymyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |

Enzymes exhibiting 4-hydroxybutyrate dehydrogenase activity (EC 1.1.1.61) also fall into this category. Such enzymes have been characterized in *Ralstonia eutropha* (Bravo et al., *J. Forensic Sci.* 49:379-387 (2004), *Clostridium kluyveri* (Wolff and Kenealy, *Protein Expr. Purif.* 6:206-212 (1995)) and *Arabidopsis thaliana* (Breitkreuz et al., *J. Biol. Chem.* 278:41552-41556 (2003)).

| Protein | GenBank ID | GI Number | Organism |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

Example V

Methods for Handling CO and Anaerobic Cultures

This example describes methods used in handling CO and anaerobic cultures.

A. Handling of CO in Small Quantities for Assays and Small Cultures.

CO is an odorless, colorless and tasteless gas that is a poison. Therefore, cultures and assays that utilized CO required special handling. Several assays, including CO oxidation, acetyl-CoA synthesis, CO concentration using myoglobin, and CO tolerance/utilization in small batch cultures, called for small quantities of the CO gas that were dispensed and handled within a fume hood. Biochemical assays called for saturating very small quantities (<2 mL) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO were dispensed to each of several possible cuvettes or vials. The Schlenk line was set up containing an oxygen scrubber on the input side and an oil pressure release bubbler and vent on the other side. Assay cuvettes were both anaerobic and CO-containing. Therefore, the assay cuvettes were tightly sealed with a rubber stopper and reagents were added or removed using gas-tight needles and syringes. Secondly, small (~50 mL) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes were pierced with 19 or 20 gage disposable syringe needles and were vented with the same. An oil bubbler was used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

B. Handling of CO in Larger Quantities Fed to Large-Scale Cultures.

Fermentation cultures are fed either CO or a mixture of CO and $H_2$ to simulate syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas are added to the cultures. At different points, the cultures are harvested or samples removed. Alternatively, cells are harvested with an integrated continuous flow centrifuge that is part of the fermenter.

The fermentative processes are carried out under anaerobic conditions. In some cases, it is uneconomical to pump oxygen or air into fermenters to ensure adequate oxygen saturation to provide a respiratory environment. In addition, the reducing power generated during anaerobic fermentation may be needed in product formation rather than respiration. Furthermore, many of the enzymes for various pathways are oxygen-sensitive to varying degrees. Classic acetogens such as *M. thermoacetica* are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway might be incompatible in the presence of oxygen because most are metallo-enzymes, key components are ferredoxins, and regulation can divert metabolism away from the Wood-Ljungdahl pathway to maximize energy acquisition. At the same time, cells in culture act as oxygen scavengers that moderate the need for extreme measures in the presence of large cell growth.

C. Anaerobic Chamber and Conditions.

Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry Calif.). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

D. Anaerobic Microbiology.

Small cultures were handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 μM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 μM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

Example VI

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. These clones were assayed for CO oxidation, using an assay that quantitatively measures CODH activity. Antisera to the *M. thermoacetica* gene products was used for Western blots to estimate specific activity. *M. thermoacetica* is Gram positive, and ribosome binding site elements are expected to work well in *E. coli*. This activity, described below in more detail, was estimated to be ~1/50th of the *M. thermoacetica* specific activity. It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum*, *Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as *Clostridial* (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., Biochemistry 43:3944-3955 (2004)). A typical activity of *M. thermoacetica* CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette four times in deionized water and one time with acetone. A small amount of vacuum grease was smeared on the top of the rubber gasket. The cuvette was gassed with CO, dried 10 min with a 22 Ga. needle plus an exhaust needle. A volume of 0.98 mlL of reaction buffer (50 mM Hepes, pH 8.5, 2 mM dithiothreitol (DTT) was added using a 22 Ga. needle, with exhaust needled, and 100% CO. Methyl viologen ($CH_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the $CH_3$ viologen. 4-5 aliquots were drawn up and discarded to wash and gas equilibrate the syringe. A small amount of sodium dithionite (0.1 M stock) was added when making up the $CH_3$ viologen stock to slightly reduce the $CH_3$ viologen. The temperature was equilibrated to 55° C. in a heated Olis spectrophotometer (Bogart Ga.). A blank reaction ($CH_3$ viologen+buffer) was run first to measure the base rate of $CH_3$ viologen reduction. Crude *E. coli* cell extracts of ACS90 and ACS91 (CODH-ACS operon of *M. thermoacetica* with and without, respectively, the first cooC). 10 microliters of extract were added at a time, mixed and assayed. Reduced $CH_3$ viologen turns purple. The results of an assay are shown in Table I.

TABLE I

Crude extract CO Oxidation Activities.

| ACS90 | 7.7 mg/ml | ACS91 | 11.8 mg/ml |
| Mta98 | 9.8 mg/ml | Mta99 | 11.2 mg/ml |

| Extract | Vol | OD/ | U/ml | U/mg |
| --- | --- | --- | --- | --- |
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

| Averages | | | | |
| --- | --- | --- | --- | --- |
| ACS90 | 0.057 U/mg | | | |
| ACS91 | 0.045 U/mg | | | |
| Mta99 | 0.0018 U/mg | | | |

Mta98/Mta99 are *E. coli* MG1655 strains that express methanol methyltransferase genes from *M. thermoacetia* and, therefore, are negative controls for the ACS90 ACS91 *E. coli* strains that contain *M. thermoacetica* CODH operons.

If ~1% of the cellular protein is CODH, then these figures would be approximately 100× less than the 500 U/mg activity of pure *M. thermoacetica* CODH. Actual estimates based on Western blots are 0.5% of the cellular protein, so the activity is about 50× less than for *M. thermoacetica* CODH. Nevertheless, this experiment demonstrates CO oxidation activity in recombinant *E. coli* with a much smaller amount in the negative controls. The small amount of CO oxidation ($CH_3$ viologen reduction) seen in the negative controls indicates that *E. coli* may have a limited ability to reduce $CH_3$ viologen.

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified *M. thermoacetica* CODH-ACS and Mtr proteins and were visualized using an alkaline phosphatase-linked goat-anti-rabbit secondary antibody. The Westerns were performed and results are shown in FIG. 9. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant *E. coli* cells express multiple components of a 7 gene operon. In addition, both the methyltransferase and corrinoid iron sulfur protein were active in the same recombinant *E. coli* cells. These proteins are part of the same operon cloned into the same cells.

The CO oxidation assays were repeated using extracts of *Moorella thermoacetica* cells for the positive controls. Though CODH activity in *E. coli* ACS90 and ACS91 was measurable, it was at about 130-150× lower than the *M. thermoacetica* control. The results of the assay are shown in FIG. 10. Briefly, cells (*M. thermoacetica* or *E. coli* with the CODH/ACS operon; ACS90 or ACS91 or empty vector: pZA33S) were grown and extracts prepared as described above. Assays were performed as described above at 55° C. at various times on the day the extracts were prepared. Reduction of methylviologen was followed at 578 nm over a 120 sec time course.

These results describe the CO oxidation (CODH) assay and results. Recombinant *E. coli* cells expressed CO oxidation activity as measured by the methyl viologen reduction assay.

Example VII

Acetyl-CoA Synthase (ACS) Activity Assay (CO Exchange Assay)

This Example describes an ACS assay method.

This assay measures the ACS-catalyzed exchange of the carbonyl group of acetyl-CoA with CO (Raybuck et al., *Biochemistry* 27:7698-7702 (1988)). ACS (as either a purified enzyme or part of a cell extract) is incubated with acetyl-CoA labeled with $^{14}C$ at the carbonyl carbon under a CO atmosphere. In the presence of active ACS, the radioactivity in the liquid phase of the reaction decreases exponentially until it reaches a minimum defined by the equilibrium between the levels of $^{14}C$-labeled acetyl-CoA and $^{14}C$-labeled CO. The same cell extracts of *E. coli* MG1655 expressing ACS90 and ACS91 employed in the other assays as well as control extracts were assayed by this method.

Briefly in more detail, in small assay vials under normal atmosphere, a solution of 0.2 mM acetyl-CoA, 0.1 mM methyl viologen, and 2 mM Ti(III)citrate in 0.3M MES buffer, pH 6.0, was made. The total reaction volume when all components were added was 500 µl. Vials were sealed with rubber stoppers (Bellco) and crimp aluminum seals (Bellco) to create a gas-tight reaction atmosphere. Each vial was sparged with 100% CO for several minutes, long enough to completely exchange the vials' atmosphere, and brought into an anaerobic chamber. The assay vials were placed in a 55° C. sand bath and allowed to equilibrate to that temperature. A total of 10 scintillation vials with 40 µl of 1M HCl were prepared for each assay vial. A gas-tight Hamilton syringe was used to add ACS to the assay vial and incubated for approximately 2-3 minutes for the reaction to come to equilibrium. A gas-tight Hamilton syringe was used to add 1 µl (0.36 nmoles) $^{14}C$-acetyl-CoA to start the assay (time=0 min). Time points were taken starting immediately. Samples (40 µl) were removed from the assay vials with a gas-tight Hamilton syringe. Each sample was added to the 40 µl of HCl in the prepared scintillation vials to quench the reaction. As the ACS enzyme transfers $^{14}C$ label to CO from acetyl-CoA, the concentration of the isotope decreases exponentially. Therefore, the assay was sampled frequently in the early time points. The precise time for each sample was recorded. The exact pace of the reaction depends on the ACS enzyme, but generally several samples are taken immediately and sampled over the initial 10-15 minutes. Samples are continued to be taken for 1-2 hours.

In a particular exemplary assay, four assay conditions were used: blank (no ACS), 12 µl of purified *E. coli* strains expressing *M. thermoacetica* ACS, 4 µl of purified *E. coli* ACS, and 3.7 µl of *M. thermoacetica* CODH/ACS. In another exemplary assay, four assay conditions were used: 108 µg CODH/ACS, 1 mg Mta99 cell extract, 1 mg ACS90 cell extract, and 1 mg ACS91 cell extract. The enzymes were added as 100 µl solutions (50 mM KPi, 0.1M NaCl, pH7.6). A more sensitive assay that can be used for most of the CODH-ACS activities is the synthesis assay described below. This example describes the assay conditions for measuring ACS activity.

Example VIII

Acetyl-CoA Synthesis and Methyltransferase Assays

This example describes acetyl-CoA synthesis and methyltransferase assays.

Acetyl-CoA synthesis assay. This assay is an in vitro reaction that synthesizes acetyl-CoA from methyl-tetrahydrofolate, CO, and CoA using CODH/ACS, methyltransferase (MeTr), and corrinoid Fe—S protein (CFeSP) (Raybuck et al., *Biochemistry* 27:7698-7702 (1988)). By adding or leaving out each of the enzymes involved, this assay can be used for a wide range of experiments, from testing one or more purified enzymes or cell extracts for activity, to determining the kinetics of the reaction under various conditions or with limiting amounts of substrate or enzyme. Samples of the reaction taken at various time points are quenched with 1M HCl, which liberates acetate from the acetyl-CoA end product. After purification with Dowex columns, the acetate can be analyzed by chromatography, mass spectrometry, or by measuring radioactivity. The exact method can be determined by the specific substrates used in the reaction.

A $^{14}C$-labeled methyl-THF was utilized, and the radioactivity of the isolated acetate samples was measured. The primary purpose was to test CFeSP subunits. The assay also included +/− purified methyltransferase enzymes. The following 6 different conditions were assayed: (1) purified CODH/ACS, MeTr, and CFeSP as a positive control; (2) purified CODH/ACS with ACS90 cell extract; (3) purified CODH/ACS with ACS91 cell extract; (4) purified CODH/ACS, MeTr with ACS90 cell extract; (5) purified CODH/ACS, MeTr with ACS91 cell extract; (6) purified CODH/ACS, MeTr with as much ACS91 cell extract as possible (excluding the MES buffer).

The reaction is assembled in the anaerobic chamber in assay vials that are filled with CO. The total reaction volume is small compared to the vial volume, so the reagents can be added before or after the vial is filled with CO, so long as a gas-tight Hamilton syringe is used and the reagents are kept anaerobic. The reaction (~60 ul total) consisted of the cell extract (except assay #1), CoA, Ti(III)citrate, MES (except assay #6), purified CODH/ACS, $^{14}C$-methyl-tetrahydrofolate, methyl-viologen, and ferredoxin. Additionally, purified MeTr was added to assays #1 and #4-6, and purified CFeSP was added to assay #1.

The reaction was carried out in an anaerobic chamber in a sand bath at 55° C. The final reagent added was the $^{14}C$-methyl-tetrahydrofolate, which started the reaction (t=0 s). An initial sample was taken immediately, followed by samples at 30 minutes, 1 hour, and 2 hours. These time points are not exact, as the 6 conditions were run concurrently (since this experiment was primarily a qualitative one). The 15 µl samples were added to 15 µl of 1M HCl in scintillation vials. For the last sample, if less than 15 µl was left in the reactions, the assay vials were rinsed with the 15 ul of HCl to take the remainder of the reaction. A volume of 10 µl of cell extract was used for assay #2-5, and 26.4 µl of cell extract was used for assay #6.

Typical amounts of purified enzyme used in the assays is as follows: CODH/ACS=~0.2 nmoles; MeTr=0.2 nmoles; CFeSP=0.05 nmoles. Typical assay concentrations are used as follows: CODH/ACS=1 uM; Me-CFeSP=0.4 uM; MeTr=1 uM; Ferredoxin=3 uM; CoA=0.26 mM; $^{14}C$ methyl-THF=0.4 mM; methyl viologen=0.1 mM; and Ti(III) citrate=3 mM.

After counting the reaction mixtures, it was determined that the corrinoid Fe—S protein in ACS90 extracts was active with total activity approaching approximately ⅕ of the positive control and significantly above the negative control (no extract).

A non-radioactive synthesis assay can also be used. Optional non-radioactive assay conditions are as follows: Assay condition #1: 100 mM MES, pH6.0; 1 mM CoA; 1 mM Me-THF; 0.33 mM Ti(III)citrate, volume to 950 ul, +50 ul of extract; incubated under a CO atmosphere (Ar for control), at 55° C. These reactions should be carried out in the dark, as the corrinoid methyl carrier is light sensitive. Assay condition #2: 100 mM MES, pH6.0; 1 mM CoA; 1 mM Me-THF; 1 mM methyl viologen; volume to 950 ul, +50 ul of extract; incubated under a CO atmosphere, at 55° C., in the dark. The reaction was quenched with 10 µl of 10% formic acid, with samples taken at 1 hr, 3 hrs, and 6.5 hrs, and stored at −20°. Assay condition #3: 100 mM Tris, pH 7.6; 5 mM CoA; 7.5 mM Me-THF; 1 mM Me-viologen; volume to 90 µl, +10 µl extract; incubated under CO or Ar, at 55° C. in the dark for 1 hr, quenched with 10 µl 10% formic acid, and stored at −20° C.

In Lu et al., (*J. Biol. Chem.* 265:3124-3133. (1990)), the pH optimum for the synthesis reaction was found to be between 7.2-7.5. Lu et al. also found that CoA concentrations above 10 mM were inhibitory. Lu et al. described using methyl iodide as the methyl donor instead of Me-THF, and used 5-7.5 mM concentrations. Lu et al. also determined that DTT or other reducing agents were not necessary, although they did use ferredoxin as an electron carrier. Methyl viologen was substituted in the above-described reactions. In addition, Maynard et al., *J. Biol. Inorg. Chem.* 9:316-322 (2004), has determined that the electron carrier was not strictly necessary, but that failure to include one resulted in a time lag of the synthesis. Maynard et al. used 1 mM methyl viologen as electron carrier when one was used.

Methyltransferase Assay. Within the CODH-ACS operon is encoded an essential methyltransferase activity that catalyzes the transfer of $CH_3$ from methyl-tetrahydrofolate to the ACS complex as part of the synthesis of acetyl-CoA. This is the step that the methyl and carbonyl pathways join together. Within the operon in *M. thermoacetica*, the Mtr-encoding gene is Moth_1197 and comes after the main CODH and ACS subunits. Therefore, Mtr activity would constitute indirect evidence that the more proximal genes can be expressed.

Mtr activity was assayed by spectroscopy. Specifically, methylated CFeSP, with Co(III), has a small absorption peak at ~450 nm, while non-methylated CFeSP, with Co(I), has a large peak at ~390 nm. This spectrum is due to both the cobalt and iron-sulfur cluster chromophores. Additionally, the CFeSP can spontaneously oxidize to Co(II), which creates a broad absorption peak at ~470 nm (Seravalli et al., *Biochemistry* 38:5728-5735 (1999)). Recombinant methyltransferase is tested using *E. coli* cell extracts, purified CFeSP from M *thermoacetica*, and methyl-tetrahydrofolate. The methylation of the corrinoid protein is observed as a decrease in the absorption at 390 nm with a concurrent increase in the absorption at 450 nm, along with the absence of a dominant peak at 470 nm.

Non-radioactive assays are also being developed using $^{13}C$-methanol. This should transfer to tetrahydrofolate and create a MTHF of molecular mass +1. Alternatively, the methyltransferase is thought to also work by transfer of the methanol methyl group to homocysteine to form methionine. This assay is also useful because methionine +1 mass is more readily detectable than MTHF+1 or some other possibilities. In addition to using $^{13}C$, deuterium can also be used as a tracer, both of which can be measured using mass spectrometry. These tracers can also be used in in vivo labeling studies. Other assay methods can be used to determine various intermediates or products including, for example, electron paramagnetic resonance (EPR), Mossbauer spectroscopy, Electron-Nuclear DOuble Resonance (ENDOR), infrared, magnetic circular dichroism (MCD), crystallography, X-ray absorption, as well as kinetic methods, including stopped flow and freeze-quench EPR.

FIG. 3B illustrates how methanol methyltransferase fits into a CODH/ACS ('syngas') pathway. Essentially, the methyl group of methanol is transferred via a cobabalamin-dependent process to tetrahydrofolate and then to the corrinoid-FeS protein of CODH/ACS (also a cobalamin protein) and that, in turn, donates the methyl group to the ACS reaction that results in acetate synthesis. The methanol methyltransferase complex consists of three gene products; two of these, MtaB and MtaC, (Moth_1209 and Moth_1208) are adjacent and were readily cloned. The third, MtaA, may be encoded by three different genes (Moth_2100, Moth_2102, and Moth_2346), and it unclear whether all three genes are required or whether a subset of the three can function. All cloning in *E. coli* was performed using the Lutz-Bujard vectors (Lutz and Bujard, *Nucleic Acids Res.* 25:1203-1210 (1997)).

The following assay can be used to determine the activity of MtaB that encodes a methanol methyltransferase gene product. A positive control for the latter can be performed with vanillate o-demethylation.

Methanol Methyltransferase reaction. An exemplary methanol methyl-transfer reaction has been described previously (Sauer and Thauer, *Eur. J. Biochem.* 249:280-285 (1997); Naidu and Ragsdale, *J. Bacteriol.* 183:3276-3281 (2001)). The reaction conditions are as follows: 50 mM MOPS/KOH, pH 7.0; 10 mM $MgCl_2$; 4 mM Ti(III)citrate; 0.2% dodecylmaltoside (replacing SDS, see Sauer and. Thauer, *Eur. J. Biochem.* 253:698-705 (1998)); 25 µM hydroxycobalamin; 1% MeOH or 1 mM vanillate (depending on the methyl transferase version). These reactions are measured by spectrograph readings in the dark at 37° C. or 55° C. This assay tests the ability of MtaB or MtvB to transfer the methyl group to cobalamin from methanol or vanillate, respectively.

Example IX

E. coli CO Tolerance Experiment and CO Concentration Assay (Myoglobin Assay)

This example describes the tolerance of *E. coli* for high concentrations of CO.

To test whether or not *E. coli* can grow anaerobically in the presence of saturating amounts of CO, cultures were set up in 120 ml serum bottles with 50 ml of Terrific Broth medium (plus reducing solution, $NiCl_2$, $Fe(II)NH_4SO_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both $N_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. $N_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. each of these was added in 1 microliter increments to the same cuvette. Midway through the experiment a second cuvette was set up and used. The results are shown in Table II.

TABLE II

Carbon Monoxide Concentrations, 36 hrs.

| Strain and Growth Conditions | Final CO concentration (micromolar) |
|---|---|
| pZA33-CO | 930 |
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

The results shown in Table II indicate that the cultures grew whether or not a strain was cultured in the presence of CO or not. These results indicate that *E. coli* can tolerate exposure to CO under anaerobic conditions and that *E. coli* cells expressing the CODH-ACS operon can metabolize some of the CO.

These results demonstrate that *E. coli* cells, whether expressing CODH/ACS or not, were able to grow in the presence of saturating amounts of CO. Furthermore, these grew equally well as the controls in nitrogen in place of CO. This experiment demonstrated that laboratory strains of *E. coli* are insensitive to CO at the levels achievable in a syngas project performed at normal atmospheric pressure. In addition, preliminary experiments indicated that the recombinant *E. coli* cells expressing CODH/ACS actually consumed some CO, probably by oxidation to carbon dioxide.

Example X

Enhanced Yield of 1,4-Butanediol from Carbohydrates Using $CO/H_2$

This example describes the generation of a microbial organism capable of producing 1,4-butanediol from carbohydrates (e.g., glucose) at a yield greater than 1 mol 1,4-butanediol/mol glucose. Synthesis gas is supplied as a secondary source of reducing equivalents to compliment the carbohydrate-based feedstock.

*Escherichia coli* is used as a target organism to engineer the 1,4-butanediol pathway shown in FIG. 6A. *E. coli* provides a good host for generating a non-naturally occurring microorganism capable of producing 1,4-butanediol from a mixed feedstock consisting of carbohydrates, CO, and/or $H_2$. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 1,4-butanediol and extract reducing equivalents from CO and $H_2$, nucleic acids encoding the requisite enzymes are expressed in *E. coli* and various non-desirable genes are targeted for deletion using well known molecular biology techniques (see, for example, Sambrook, supra, 2001; Ausubel, supra, 1999). The construction of a host *E. coli* strain capable of synthesizing 1,4-butanediol from succinyl-CoA is described in (Burk et al., WO 2008/115840). Targeted gene deletions of lactate dehydrogenase (ldh), alcohol/aldehyde dehydrogenase (adhE), pyruvate formate lyase (pfl), succinate semialdehyde dehydrogenase (sad and gabD) are implemented for enhancing the yield of 1,4-butanediol.

Suitable host backgrounds include AB3 and ECKh-138 as described by Van Dien et al., (2009). Genes integrated into the chromosome or expressed via plasmids to enable 1,4-butanediol production from succinyl-CoA include succinyl-CoA reductase (aldehyde forming) [sucD, NP_904963.1, GI: 34540484, *Porphyromonas gingivalis* W83], 4-hydroxybutyrate dehydrogenase[4hbd, NP_904964.1, GI: 34540485, *Porphyromonas gingivalis* W83], 4-hydr nn oxybutyryl-CoA transferase [cat2, NP_906037.1, GI: 34541558, *Porphyromonas gingivalis* W83], and 4-hydroxybutyryl-CoA reductase (aldehyde forming) [GNM0025B—codon optimized variant of ald, AAT66436, GI: 49473535, *Clostridium beijerinckii*—described in Van Dien et al., (2009). Endogenous alcohol dehydrogenases can carry out the reduction of 4-hydroxybutyryaldehyde to 1,4-butanediol. This step can be enhanced by overexpressing a native alcohol dehydrogenase such as (yqhD, NP_417484.1, GI: 16130909, *Escherichia coli*) or a non-native alcohol dehydrogenase such as (adhA, YP_162971.1, GI: 56552132, *Zymomonas mobilis*). PEP carboxykinase from *E. coli* [pck, NP_417862.1, GI: 16131280], *H. influenzae* [pckA, P43923.1, GI: 1172573], or another organism are expressed to improve the energetic efficiency of the engineered pathway.

1,4-Butanediol pathway genes are integrated into the chromosome as synthetic operons. This entails targeted integration using RecET-based 'recombineering' (Angrand et al., *Nucleic Acids Res.* 27.17:e16 (1999); Muyrers et al., *Nucleic Acids Res.* 27.6:1555-1557 (1999); Zhang et al., *Nat. Genet.* 20.2:123-128 (1998)). A potential issue with RecET-based integration of a cassette and removal of a FRT or loxP-bounded selectable marker by FLP or Cre is the production of a recombination scar at each integration site. While problems caused by this can be minimized by a number of methods, other means that do not leave genomic scars are available. The standard alternative is to introduce the desired genes using integrative 'suicide' plasmids coupled to counter-selection such as that allowed by the *Bacillus* sacB gene (Link et al., *J. Bacteriol.* 179.20:6228-6237 (1997)); in this way, markerless and scar less insertions at any location in the *E. coli* chromosome can be generated.

Carbon monoxide dehydrogenase activity is enabled by cloning the following genes from *Clostridium carboxydivorans* P7 (ZP_05391756.1, GI: 255524806; ZP_05391757.1, GI: 255524807; ZP_05391758.1, GI: 255524808; ZP_05392945, GI: 255526021) into the pZE13 vector (Expressys, Ruelzheim, Germany) under the PA1/lacO promoter. Alternatively, carbon monoxide dehydrogenase activity is enabled by cloning the following genes from *Clostridium carboxydivorans* P7 (ZP_05392944, GI: 255526020; ZP_05392945, GI: 255526021) into the pZE13 vector (Expressys, Ruelzheim, Germany) under the PA1/lacO promoter. In addition, ferredoxin and NAD(P)H:ferredoxin oxidoreductase activity is enabled by cloning the following genes from *Clostridium carboxydivorans* P7 (ZP_05392639.1, GI: 255525707; ZP_05392638.1, GI: 255525706; ZP_05392636.1, GI: 255525704; ZP_05392958.1, GI: 255526034) or from *Helicobacter pylori* (NP_207955.1; GI: 15645778; AAD07340.1, GI: 2313367) into the pZA33 vector (Expressys, Ruelzheim, Germany) under the PA1/lacO promoter. Hydrogenase activity is enabled by cloning the following genes from *Ralstonia eutropha* H16 (HoxF, NP_942727.1, GI: 38637753; HoxU, NP_942728.1, GI: 38637754; HoxY, NP_942729.1, GI: 38637755; HoxH, NP_942730.1, GI: 38637756; HoxW, NP_942731.1, GI: 38637757; HoxI, NP_942732.1, GI: 38637758) into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques.

Cloned genes are verified by PCR and or restriction enzyme mapping to demonstrate construction and insertion into the expression vector. DNA sequencing of the presumptive clones is carried out to confirm the expected sequences of each gene. Expression of the cloned genes is monitored using SDS-PAGE of whole cell extracts. To optimize levels of soluble vs. pellet (potentially inclusion body origin) protein, the affect of titration of the promoter on these levels can be examined. If no acceptable expression is obtained, higher or lower copy number vectors or variants in promoter strength are tested. The three sets of plasmids are transformed into the 1,4-butanediol-producing host strain of *E. coli* to express the proteins and enzymes required for the extraction of reducing equivalents from $H_2$ and CO.

The resulting genetically engineered organism is cultured in glucose-containing medium following procedures well known in the art (see, for example, Sambrook et al., supra, 2001). The expression of the 1,4-butanediol synthesis and reducing equivalent extraction genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The assay for CO dehydrogenase activity is one of the simpler, reliable, and more versatile assays of enzymatic activities within the Wood-Ljungdahl pathway (Ragsdale and Wood, *J. Biol. Chem.* 260:3970-3977 (1985)). It will provide a measure of the activity of CODH in recombinant cells. This assay employs reduction of methyl viologen in the presence of CO. This is measured at 578 nm in stoppered, anaerobic, glass cuvettes. Some hydrogenase assays use electron acceptors such as methyl viologen and test the enzymatic activity relative to inhibitors such as cyanide (Ragsdale and Ljungdahl, *Arch. Microbiol.* 139: 361-365 (1984); Menon and Ragsdale, *Biochemistry* 36:8484-8494 (1996)). Assays for hydrogenase activity that directly measure $H_2$ generation or loss with GC or $H_2$ electrodes can also be applied (Der et al., *Anal. Biochem.* 150:481-486 (1985)). The ability of the engineered *E. coli* strain to produce 1,4-butanediol is confirmed using HPLC, gas chromatography-mass spectrometry (GCMS), liquid chromatography-mass spectrometry (LCMS), or other suitable analytical methods using routine procedures well known in the art.

Microbial strains engineered to have a functional 1,4-butanediol synthesis and reducing equivalent extraction pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 1,4-butanediol. One modeling method is the bilevel optimization approach, OptKnock (Burgard et al., *Biotechnol. Bioengineer.* 84:647-657 (2003)), which is applied to select gene knockouts that collectively result in better production of 1,4-butanediol. Adaptive evolution also can be used to generate better producers of, for example, the succinyl-CoA intermediate of the 1,4-butanediol product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the 1,4-butanediol producer to further increase production.

Initial conditions employ strictly anaerobically grown cells provided with exogenous glucose as a carbon and energy source. Alternatively, or in addition to glucose, nitrate can be added to the fermentation broth to serve as an electron acceptor and initiator of growth. Anaerobic growth of *E. coli* on fatty acids, which are ultimately metabolized to acetyl-CoA, has been demonstrated in the presence of nitrate (Campbell et al., *Mol. Microbiol.* 47:793-805 (2003). Oxygen can also be provided as long as its intracellular levels are maintained below any inhibition threshold of the engineered enzymes. Anaerobic conditions are maintained by first sparging the medium with nitrogen, then CO and $H_2$, and finally sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art.

For large-scale production of 1,4-butanediol, the above organism is cultured in a fermenter using a medium known in the art to support growth of the organism under anaerobic or microaerobic conditions. Fermentations are performed in either a batch, fed-batch or continuous manner. Previous studies have shown that a rate-limiting step to syngas utilization can be the mass transfer of CO into the liquid phase (Do et al., *Biotechnol. Bioeng.* 97:279-286 (2007)). This is largely due to the relatively low solubility of CO in water. Continuously gas-sparged fermentations (i.e., with $H_2$ and CO) are performed in controlled fermenters with continuous off-gas analysis by mass spectrometry and periodic liquid sampling and analysis by GC and HPLC. 1,4-butanediol production, as well as detailed metabolite production, are quantified via GCMS or LCMS. All piping in these systems is glass or metal to maintain anaerobic conditions. The gas sparging is done using glass fits to decrease bubble size, maximize the surface to volume ratio, and improve mass transfer. Various sparging rates are tested, ranging from about 0.1 to 1 vvm (vapor volumes per minute). Agitation and impeller design are examined. We will also test methods such as moderate overpressure at 1.5 atm to improve mass transfer (Najafpour and Younesi, 38(1-2):223-228 (2006)). To obtain accurate measurements of gas uptake rates, periodic challenges are performed in which the gas flow is temporarily stopped, and the gas phase composition is monitored as a function of time. We also will evaluate other high mass transfer systems such as bubble columns, which allow hydrostatic overpressure and longer bubble retention times. Fermentation conditions are optimized to further improve the productivity and titer of the 1,4-butanediol producing strains. The data generated from fermentations are analyzed to discern the impact of each parameter on cell density and alcohol yield. The pH of the culture impacts the growth of the host and may also affect the bioavailability of some of the trace elements. Other parameters to be optimized include temperature, trace metals innoculum size, ionic strength and duration of fermentation.

Example XI

Engineering the Reverse TCA Cycle into an Isopropanol-Producing Organism

This example describes the generation of a microbial organism that has been engineered to produce isopropanol from glucose and $CO_2$. The organism contains a functional reverse TCA cycle and a pathway for producing isopropanol from acetyl-CoA as shown in FIG. 2b. Engineering a functional pathway to produce isopropanol from glucose and $CO_2$ at high yields will require the optimized expression of a combination of exogenous and/or endogenous genes.

*Escherichia coli* is used as a target organism for engineering an isopropanol-producing pathway that utilizes enzymes from the reduced TCA cycle to assimilate $CO_2$. *E. coli* provides a good host for generating a non-naturally occurring microorganism capable of producing isopropanol. *E. coli* is amenable to genetic manipulation and is known to be capable of producing various products, like ethanol, acetic acid, formic acid, lactic acid, and succinic acid, effectively under anaerobic or microaerobic conditions. Engineering a functional pathway to produce isopropanol from glucose and $CO_2$ at high yields will require the optimized expression of a combination of exogenous and/or endogenous genes.

To generate an *E. coli* strain engineered to produce isopropanol, nucleic acids encoding the enzymes utilized in the isopropanol pathway from acetyl-CoA are expressed in *E. coli* using well known molecular biology techniques (see, for example, Sambrook, supra, 2001; Ausubel supra, 1999; Roberts et al., supra, 1989). In particular, an *E. coli* strain is engineered to produce isopropanol from acetyl-CoA via the route outlined in Figure XX. Conversion of acetyl-CoA to acetoacetyl-CoA is catalyzed by acetoacetyl-CoA thiolase, an enzyme native to *E. coli* encoded by atoB (NP_416728). For the first stage of pathway construction, genes encoding enzymes to transform acetoacetyl-CoA to isopropanol are assembled onto a vector. In particular, the genes ctfAB (NP_149326.1 and NP_149327.1), adc (NP_149328.1), and adh (AAA23199.2) encoding acetoacetyl-CoA-transferase, acetoacetate decarboxylase and isopropanol dehydrogenase, respectively, are cloned into the pZE13 vector (Expressys, Ruelzheim, Germany), under the control of the PA1/lacO promoter. The vector is transformed into E. coli strain MG1655 to express the proteins and enzymes required for isopropanol synthesis from acetoacetyl-CoA.

The resulting genetically engineered organism is cultured in glucose containing medium following procedures well known in the art (see, for example, Sambrook et al., supra, 2001). The expression of isopropanol pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered E. coli strain to produce isopropanol through this pathway is confirmed using HPLC, gas chromatography-mass spectrometry (GCMS) or liquid chromatography-mass spectrometry (LCMS).

Microbial strains engineered to have a functional isopropanol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers. After successful demonstration of enhanced isopropanol production via the activities of the exogenous enzymes, the genes encoding these enzymes are inserted into the chromosome of a wild type E. coli host using methods known in the art. Such methods include, for example, sequential single crossover (Gay et al., J. Bacteriol. 153:1424-1431 (1983) and Red/ET methods from GeneBridges (Zhang et al. (2001). Chromosomal insertion provides several advantages over a plasmid-based system, including greater stability and the ability to co-localize expression of pathway genes.

The isopropanol-overproducing host strain is further engineered to assimilate $CO_2$ via the reductive TCA cycle as shown in FIG. 2B. Many of the native E. coli enzymes are capable of operating in the reductive direction including aconitase, isocitrate dehydrogenase, succinyl-CoA synthetase, fumarate reductase, fumarase and malate dehydrogenase. To generate a strain with a functional RTCA cycle, nucleic acids encoding alpha-ketoglutarate synthase, pyruvate:ferredoxin oxidoreductase, ATP-citrate synthase, ferredoxin and ferredoxin:$NADP^+$ reductase are expressed in the isopropanol-producing host using well known molecular biology techniques (see, for example, Sambrook, supra, 2001; Ausubel supra, 1999; Roberts et al., supra, 1989).

In particular, the korAB (BAB21494 and BAB21495), por (YP_428946.1) genes encoding the alpha-ketoglutarate synthase and pyruvate:ferredoxin oxidoreductase, respectively, are cloned into the pZE13 vector (Expressys, Ruelzheim, Germany), under the control of the PA1/lacO promoter. This plasmid is then transformed into a host strain containing $lacI^Q$, which allows inducible expression by addition of isopropyl-beta-D-1-thiogalactopyranoside (IPTG). The genes aclAB (AAM72321.1 and AAM72322.1), fdx1 (BAE02673.1) and HP1164 (NP_207955.1) encoding ATP-citrate synthase, ferredoxin and ferredoxin:$NADP^+$ reductase, respectively, are cloned into the pZA33 vector (Expressys, Ruelzheim, Germany) under the PA1/lacO promoter. The two sets of plasmids are transformed into the isopropanol-producing E. coli strain, described above, to express the proteins and enzymes required for $CO_2$ assimilation to acetyl-CoA, and subsequently isopropanol, via the reductive TCA cycle.

The resulting genetically engineered organism is cultured in glucose-containing medium following procedures well known in the art (see, for example, Sambrook et al., supra, 2001). The expression of reductive TCA cycle genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered E. coli strain to assimilate $CO_2$ through this pathway is confirmed using $^{13}C$ labeled bicarbonate, HPLC, gas chromatography-mass spectrometry (GCMS) or liquid chromatography-mass spectrometry (LCMS).

Microbial strains engineered to have a functional reductive TCA pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced isopropanol production via the activities of the exogenous enzymes, the genes encoding these enzymes are inserted into the chromosome of a wild type E. coli host using methods known in the art. Such methods include, for example, sequential single crossover ((Gay et al., J. Bacteriol. 153:1424-1431 (1983) and Red/ET methods from GeneBridges (Zhang et al. (2001). Chromosomal insertion provides several advantages over a plasmid-based system, including greater stability and the ability to co-localize expression of pathway genes.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of isopropanol. One modeling method is the bilevel optimization approach, OptKnock (Burgard et al., Biotechnol. Bioengineer. 84:647-657 (2003)), which is applied to select gene knockouts that collectively result in better production of isopropanol. Adaptive evolution also can be used to generate better producers of, for example, acetyl-CoA or acetoacetyl-CoA intermediates or the isopropanol product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the isopropanol producer to further increase production.

For large-scale production of isopropanol, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2504. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Example XII

Introducing the Syngas Utilization Pathway into an Isopropanol Producing Organism This example describes the generation of a microbial organism that has been engineered to produce isopropanol from glucose and $CO_2$. The organism contains a functional Wood Ljungdahl pathway for fixing carbon as shown in FIG. 4A and a pathway for producing isopropanol from acetyl-CoA as shown in FIG. 1B.

*Escherichia coli* is used as a target organism for engineering an isopropanol-producing pathway that utilizes enzymes from the Wood ljungdahl pathway to fix $CO_2$. *E. coli* provides a good host for generating a non-naturally occurring microorganism capable of producing isopropanol. *E. coli* is amenable to genetic manipulation and is known to be capable of producing various products, like ethanol, acetic acid, formic acid, lactic acid, and succinic acid, effectively under anaerobic or microaerobic conditions. Engineering a functional pathway to produce isopropanol from glucose and $CO_2$ at high yields will require the optimized expression of a combination of exogenous and/or endogenous genes.

To generate an *E. coli* strain engineered to produce isopropanol, nucleic acids encoding the enzymes utilized in the isopropanol pathway from acetyl-CoA are expressed in *E. coli* using well known molecular biology techniques (see, for example, Sambrook, supra, 2001; Ausubel supra, 1999; Roberts et al., supra, 1989). In particular, an *E. coli* strain is engineered to produce isopropanol from acetyl-CoA via the route outlined in FIG. 1B. Conversion of acetyl-CoA to acetoacetyl-CoA is catalyzed by acetoacetyl-CoA thiolase, an enzyme native to *E. coli* encoded by atoB (NP_416728). For the first stage of pathway construction, genes encoding enzymes to transform acetoacetyl-CoA to isopropanol are assembled onto a vector. In particular, the genes ctfAB (NP_149326.1 and NP_149327.1), adc (NP_149328.1), and adh (AAA23199.2) encoding acetoacetyl-CoA-transferase, acetoacetate decarboxylase and isopropanol dehydrogenase, respectively, are cloned into the pZE13 vector (Expressys, Ruelzheim, Germany), under the control of the PA1/lacO promoter. The vector is transformed into *E. coli* strain MG1655 to express the proteins and enzymes required for isopropanol synthesis from acetoacetyl-CoA.

The resulting genetically engineered organism is cultured in glucose containing medium following procedures well known in the art (see, for example, Sambrook et al., supra, 2001). The expression of isopropanol pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce isopropanol through this pathway is confirmed using HPLC, gas chromatography-mass spectrometry (GCMS) or liquid chromatography-mass spectrometry (LCMS).

Microbial strains engineered to have a functional isopropanol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers. After successful demonstration of enhanced isopropanol production via the activities of the exogenous enzymes, the genes encoding these enzymes are inserted into the chromosome of a wild type *E. coli* host using methods known in the art. Such methods include, for example, sequential single crossover (Gay et al., *J. Bacteriol.* 153:1424-1431 (1983) and Red/ET methods from GeneBridges (Zhang et al. (2001). Chromosomal insertion provides several advantages over a plasmid-based system, including greater stability and the ability to co-localize expression of pathway genes.

The isopropanol-overproducing host strain is further engineered to assimilate carbon via the Wood Ljungdahl pathway as shown in FIG. 4A. The enzymes required to be active are formate dehydrogenase, Formyltetrahydrofolate synthetase, Methenyltetrahydrofolate cyclohydrolase, Methylenetetrahydrofolate dehydrogenase, Methylenetetrahydrofolate reductase, Methyltetrahydrofolate:corrinoid protein methyltransferase (AcsE), Corrinoid iron-sulfur protein (AcsD), Nickel-protein assembly protein (AcsF & CooC), Ferredoxin (Orf7), Acetyl-CoA synthase (AcsB & AcsC), Carbon monoxide dehydrogenase (AcsA), Pyruvate formate lyase (Pfl), and Pyruvate ferredoxin oxidoreductase (Por) or pyruvate dehydrogenase (PDH).

While *E. coli* naturally possesses the capability for some of the required transformations in the methyl branch (i.e., methenyltetrahydrofolate cyclohydrolase, methylenetetrahydrofolate dehydrogenase, methylenetetrahydrofolate reductase), it is thought that the methyl branch enzymes from acetogens may have significantly higher (50-100×) specific activities than those from non-acetogens (Morton et al., *Genetics and Molecular Biology of Anaerobic Bacteria*, M. Sebald, Ed., New York: Springer Verlag pp. 389-406 (1992)). Formate dehydrogenase also appears to be specialized for anaerobic conditions (Ljungdahl and Andreesen, *FEBS Lett.* 54:279-282 (1975)). Therefore, various non-native versions of each of these are expressed in the strain of *E. coli* capable of methanol and syngas utilization. For example, Moth_2312 and Moth_2314 (Accession numbers YP_431142 and YP_431144 respectively) encoding the alpha and beta subunits of formate dehydrogenase, Moth_0109 (GenBank No: YP_428991.1) encoding for formyltetrahydrofolate synthetase, Moth_1516 (Accession no: YP_430368.1) encoding for methenyltetrahydrofolate cyclohydrolase and methylenetetrahydrofolate dehydrogenase, and Moth_1191 (Accession no: YP_430048.1) encoding for methylenetetrahydrofolate reductase will be cloned and combined into an expression vector designed to express them as a set. Initially, a high or medium copy number vector will be chosen (using ColE1 or P15A replicons). The first promoter to be tested is a strongly constitutive promoter such as lambda pL or an IPTG-inducible version of this, pL-lacO (Lutz and Bujard, *Nucleic Acids Res.* 25:1203-1210 (1997)). To make an artificial operon, one 5' terminal promoter is placed upstream of the set of genes and each gene receives a consensus rbs element. The order of genes is based on the natural order whenever possible. Ultimately, the genes are integrated into the *E. coli* chromosome. Enzyme assays are performed as described in (Ljungdahl and Andreesen, supra; Yamamoto et al., *J. Biol. Chem.* 258:1826-1832 (1983); Lovell et al., *Arch. Microbiol.* 149: 280-285 (1988); de Mata and Rabinowitz, *J. Biol. Chem.* 255:2569-2577(1980); D'Ari and Rabinowitz, *J. Biol. Chem.* 266:25953-23958 (1991); Clark and Ljungdahl, *J. Biol. Chem.* 259:10845-10849 (1984); Clark and Ljungdahl, *Methods Enzymol.* 122:392-399 (1986)).

Expression of acetyl CoA synthase/CO dehydrogenase in a foreign host requires introducing many, if not all, of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes required for carbon-monoxide dehydrogenase/acetyl-CoA synthase activity typically reside in a limited region of the native genome that may be an extended operon (Ragsdale, *Crit. Rev. Biochem. Mol. Biol.* 39:165-195 (2004); Morton et al., *J. Biol. Chem.* 266:23824-23828 (1991); Roberts et al., *Proc. Nat. Acad. Sci. U.S.A.* 86:32-36 (1989)). Each of the genes in this operon from the acetogen, *M. thermoacetica*, has already been cloned and expressed actively in *E. coli* (Morton et al., *J. Biol. Chem.* 266:23824-23828 (1991); Roberts et al., supra; Lu et al., *J. Biol. Chem.* 268:5605-5614 (1993)). The protein sequences of these genes can be identified by the following GenBank accession numbers.

| Protein | GenBank ID | Organism |
| --- | --- | --- |
| AcsE | YP_430054 | *Moorella thermoacetica* |
| AcsD | YP_430055 | *Moorella thermoacetica* |
| AcsF | YP_430056 | *Moorella thermoacetica* |
| Orf7 | YP_430057 | *Moorella thermoacetica* |
| AcsC | YP_430058 | *Moorella thermoacetica* |
| AcsB | YP_430059 | *Moorella thermoacetica* |
| AcsA | YP_430060 | *Moorella thermoacetica* |
| CooC | YP_430061 | *Moorella thermoacetica* |

Using standard PCR methods, the entire ACS/CODH operons are assembled into low or medium copy number vectors such as pZA33-S (P15A-based) or pZS13-S (pSC101-based). The structures and sequences of the cloned genes are confirmed. Expression is monitored via protein gel electrophoresis of whole-cell lysates grown under strictly anaerobic conditions with the requisite metals (Ni, Zn, Fe) and coenzyme $B_{12}$ provided. As necessary, the gene cluster is modified for *E. coli* expression by identification and removal of any apparent terminators and introduction of consensus ribosomal binding sites chosen from sites known to be effective in *E. coli* (Barrick et al., *Nucleic Acids Res.* 22:1287-1295 (1994); Ringquist et al., *Mol. Microbiol.* 6:1219-1229 (1992)). However, each gene cluster is cloned and expressed in a manner parallel to its native structure and expression. This helps ensure the desired stoichiometry between the various gene products—most of which interact with each other.

*E. coli* possesses native pyruvate formate lyase activity. The resulting genetically engineered organism is cultured in glucose-containing medium following procedures well known in the art (see, for example, Sambrook et al., supra, 2001). The expression of the methyl/carbonyl branch genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to assimilate carbon through this pathway is confirmed using $^{13}C$ labeled bicarbonate, HPLC, gas chromatography-mass spectrometry (GCMS) or liquid chromatography-mass spectrometry (LCMS). Initial conditions employ strictly anaerobically grown cells provided with exogenous glucose as a carbon and energy source via substrate-level phosphorylation or anaerobic respiration with nitrate as an electron acceptor. Additionally, exogenously provided $CH_3$-THF is added to the medium.

Microbial strains engineered to have a functional W-L pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced isopropanol production via the activities of the exogenous enzymes, the genes encoding these enzymes are inserted into the chromosome of a wild type *E. coli* host using methods known in the art. Such methods include, for example, sequential single crossover (Gay et al., *J. Bacteriol.* 153:1424-1431 (1983) and Red/ET methods from GeneBridges (Zhang et al. (2001). Chromosomal insertion provides several advantages over a plasmid-based system, including greater stability and the ability to co-localize expression of pathway genes.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of isopropanol. One modeling method is the bilevel optimization approach, OptKnock (Burgard et al., *Biotechnol. Bioengineer.* 84:647-657 (2003)), which is applied to select gene knockouts that collectively result in better production of isopropanol. Adaptive evolution also can be used to generate better producers of, for example, acetyl-CoA or acetoacetyl-CoA intermediates or the isopropanol product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the isopropanol producer to further increase production.

For large-scale production of isopropanol, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Example XIII

Engineering the Methanol Utilization Pathway into an Isopropanol Producing Organism This Example shows how an organism is engineered to utilize methanol in an isopropanol producing organism.

The first step in the cloning and expression process is to express in *E. coli* the minimal set of genes (e.g., MtaA, MtaB, and MtaC) necessary to produce Methyl-THF from methanol (FIG. 4B). These methyltransferase activities require Coenzyme $B_{12}$ (cobalamin) as a cofactor. In *Moorella thermoacetica*, a cascade of methyltransferase proteins mediate incorporation of methanol derived methyl groups into the acetyl-CoA synthase pathway. Recent work (Das et al., *Proteins* 67:167-176 (2007) suggests that MtaABC are encoded by Moth_1208-09 and Moth_2346. These genes are cloned via proof-reading PCR and linked together for expression in a high-copy number vector such as pZE22-S under control of the repressible PA1-lacO1 promoter (Lutz and Bujard, *Nucleic Acids Res.* 25:1203-1210 (1997). Cloned genes are verified by PCR and or restriction enzyme mapping to demonstrate construction and insertion of the 3-gene set into the expression vector. DNA sequencing of the presumptive clones is carried out to confirm the expected sequences of each gene. Once confirmed, the final construct is expressed in *E. coli* K-12 (MG1655) cells by addition of IPTG inducer between 0.05 and 1 mM final concentration. Expression of the cloned genes is monitored using SDS-PAGE of whole cell extracts. To optimize levels of soluble vs. pellet (potentially inclusion body origin) protein, the affect of titration of the promoter on these levels can be examined. If no acceptable expression is obtained, higher or lower copy number vectors or variants in promoter strength are tested.

To determine if expression of the MtaABC proteins from *M. thermoacetica* confers upon *E. coli* the ability to transfer methyl groups from methanol to tetrahydrofolate (THF) the recombinant strain is fed methanol at various concentrations. Activity of the methyltransferase system is assayed anaerobically as described for vanillate as a methyl source in *M. thermoacetica* (Naidu and Ragsdale, *J. Bacteriol.* 183: 3276-3281 (2001) or for *Methanosarcina barkeri* methanol methyltransferase (Sauer et al., *Eur. J. Biochem.* 243:670-677 (1997); Tallant et al., *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996)). For a positive control, *M. thermoacetica* cells are cultured in parallel and assayed anaerobically to confirm endogenous methyltransferase activity. Demonstration of dependence on exogenously added coenzyme $B_{12}$ confirms methanol:corrinoid methyltransferase activity in *E. coli*.

Once methyltransferase expression is achieved, further work is performed towards optimizing the expression. Titrating the promoter in the expression vector enables the testing of a range of expression levels. This is then used as a guide towards the expression required in single-copy, or enables the determination of whether or not a single-copy of these genes allows sufficient expression. If so, the methyl-transferase genes are integrated into the chromosome as a single, synthetic operon. This entails targeted integration using RecET-based 'recombineering' (Angrand et al., *Nucleic Acids Res.* 27:e16 (1999); Muyrers et al., *Nucleic Acids Res.* 27:1555-1557 (1999); Zhang et al., *Nat. Genet.* 20:123-128 (1998)). A potential issue with RecET-based integration of a cassette and removal of a FRT or loxP-bounded selectable marker by FLP or Cre is the production of a recombination scar at each integration site. While problems caused by this can be minimized by a number of methods, other means that do not leave genomic scars are available. The standard alternative, is to introduce the desired genes using integrative 'suicide' plasmids coupled to counter-selection such as that allowed by the *Bacillus* sacB gene (Link et al., *J. Bacteriol.* 179:6228-6237 (1997); in this way, markerless and scar less insertions at any location in the *E. coli* chromosome can be generated. The final goal is a strain of *E. coli* K-12 expressing methanol:corrinoid methyltransferase activity under an inducible promoter and in single copy (chromosomally integrated).

Expression of acetyl CoA synthase/CO dehydrogenase in a foreign host requires introducing many, if not all, of the following proteins and their corresponding activities. Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes required for carbon-monoxide dehydrogenase/acetyl-CoA synthase activity typically reside in a limited region of the native genome that may be an extended operon (Ragsdale, *Crit. Rev. Biochem. Mol. Biol.* 39:165-195 (2004); Morton et al., *J. Biol. Chem.* 266:23824-23828 (1991); Roberts et al., *Proc. Natl. Acad. Sci. U.S.A.* 86:32-36 (1989)). Each of the genes in this operon from the acetogen, *M. thermoacetica*, has already been cloned and expressed actively in *E. coli* (Morton et al., *J. Biol. Chem.* 266:23824-23828 (1991); Roberts et al., *Proc. Natl. Acad. Sci. U.S.A.* 86:32-36 (1989); Lu et al., *J. Biol. Chem.* 268:5605-5614 (1993)). The protein sequences of these genes can be identified by the following GenBank accession numbers.

| Protein | GenBank ID | Organism |
| --- | --- | --- |
| AcsE | YP_430054 | *Moorella thermoacetica* |
| AcsD | YP_430055 | *Moorella thermoacetica* |
| AcsF | YP_430056 | *Moorella thermoacetica* |
| Orf7 | YP_430057 | *Moorella thermoacetica* |
| AcsC | YP_430058 | *Moorella thermoacetica* |
| AcsB | YP_430059 | *Moorella thermoacetica* |
| AcsA | YP_430060 | *Moorella thermoacetica* |
| CooC | YP_430061 | *Moorella thermoacetica* |

Using standard PCR methods, the entire ACS/CODH operons are assembled into low or medium copy number vectors such as pZA33-S (P15A-based) or pZS13-S (pSC101-based). The structures and sequences of the cloned genes are confirmed. Expression is monitored via protein gel electrophoresis of whole-cell lysates grown under strictly anaerobic conditions with the requisite metals (Ni, Zn, Fe) and coenzyme $B_{12}$ provided. As necessary, the gene cluster is modified for *E. coli* expression by identification and removal of any apparent terminators and introduction of consensus ribosomal binding sites chosen from sites known to be effective in *E. coli* (Barrick et al., *Nucleic Acids Res.* 22:1287-1295 (1994); Ringquist et al., *Mol. Microbiol.*

6:1219-1229 (1992)). However, each gene cluster is cloned and expressed in a manner parallel to its native structure and expression. This helps ensure the desired stoichiometry between the various gene products—most of which interact with each other.

E. coli possesses native pyruvate formate lyase activity. The resulting genetically engineered organism is cultured in glucose-containing medium following procedures well known in the art (see, for example, Sambrook et al., supra, 2001). The expression of the exogenous genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered E. coli strain to assimilate carbon through this pathway is confirmed using $^{13}C$ labeled bicarbonate, HPLC, gas chromatography-mass spectrometry (GCMS) or liquid chromatography-mass spectrometry (LCMS). Initial conditions employ strictly anaerobically grown cells provided with exogenous glucose as a carbon and energy source via substrate-level phosphorylation or anaerobic respiration with nitrate as an electron acceptor. Additionally, exogenously provided $CH_3$-THF is added to the medium.

Microbial strains engineered to have a functional methanol utilization pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced isopropanol production via the activities of the exogenous enzymes, the genes encoding these enzymes are inserted into the chromosome of a wild type E. coli host using methods known in the art. Such methods include, for example, sequential single crossover (Gay et al., J. Bacteriol. 153:1424-1431 (1983) and Red/ET methods from GeneBridges (Zhang et al. (2001). Chromosomal insertion provides several advantages over a plasmid-based system, including greater stability and the ability to co-localize expression of pathway genes.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of isopropanol. One modeling method is the bilevel optimization approach, OptKnock (Burgard et al., Biotechnol. Bioengineer. 84:647-657 (2003)), which is applied to select gene knockouts that collectively result in better production of isopropanol. Adaptive evolution also can be used to generate better producers of, for example, acetyl-CoA or acetoacetyl-CoA intermediates or the isopropanol product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the isopropanol producer to further increase production.

For large-scale production of isopropanol, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2504. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., Biotechnol. Bioeng., 775-779 (2005).

Example XIV

Engineering Cobalamin Synthesis into an Organism

This example describes engineering de novo $B_{12}$ synthetic capability into an organism. One enzyme of the Wood-Ljungdahl pathway, ACS/CODH, uses cobalamin (vitamin $B_{12}$) to function. $B_{12}$ is synthesized de novo in some organisms but must be supplied exogenously to others. Still other organisms such as S. cerevisiae lack the ability to efficiently uptake $B_{12}$.

$B_{12}$ biosynthetic pathways have been characterized in several organisms including Salmonella typhimurium LT2 (Roth et al., J. Bacteriol. 175:3303-3316 (1993), Lactobacillus reuteri CRL1098 (Santos et al., Microbiology 154:81-93 (2008) and Bacillus megaterium (Brey et al., J. Bacteriol. 167:623-630 (1986)). Bacterial $B_{12}$ biosynthesis pathways involve 20-30 genes clustered together in one or more operons. Two cobalamin biosynthesis pathways: late-insertion (aerobic only) and early-insertion (anaerobic) have been described (Scott, A. I., J. Org. Chem. 68:2529-2539 (2003)). The final products of the biosynthesis of vitamin $B_{12}$ are 5'-deoxyadenosylcobalamin (coenzyme $B_{12}$) and methylcobalamin (MeCbl). Vitamin $B_{12}$ is defined as cyanocobalamin (CNCbl) which is the form commonly prepared in industry. In this example, $B_{12}$ refers to all three analogous molecules.

The anaerobic cobalamin biosynthesis pathway has been well-characterized in Salmonella typhimurium LT2 (Roth et al., J. Bacteriol. 175:3303-3316 (1993)). Pathway genes are clustered in a large operon termed the cob operon. A plasmid containing the following 20 genes from the cob operon (pAR8827) was transformed into E. coli and conferred the ability to synthesize cobalamin de novo (Raux et al., J. Bacteriol. 178:753-767 (1996)). To further improve yield of the cobyric acid precursor, the known regulatory elements of cbiA were removed and the RBS altered. The genes and corresponding GenBank identifiers and gi numbers are listed below.

| Protein | GenBank ID | GI Number | Organism |
|---|---|---|---|
| cysG | NP_462380.1 | 16766765 | Salmonella typhimurium |
| cbiK | NP_460970.1 | 16765355 | Salmonella typhimurium |
| cbiL | NP_460969.1 | 16765354 | Salmonella typhimurium |
| cbiH | NP_460972.1 | 16765357 | Salmonella typhimurium |
| cbiF | NP_460974.1 | 16765359 | Salmonella typhimurium |

| Protein | GenBank ID | GI Number | Organism |
|---|---|---|---|
| cbiG | NP_460973.1 | 16765358 | *Salmonella typhimurium* |
| cbiD | NP_460977.1 | 16765362 | *Salmonella typhimurium* |
| cbiJ | NP_460971.1 | 16765356 | *Salmonella typhimurium* |
| cbiE | NP_460976.1 | 16765361 | *Salmonella typhimurium* |
| cbiT | NP_460975.1 | 16765360 | *Salmonella typhimurium* |
| cbiC | NP_460978.1 | 16765363 | *Salmonella typhimurium* |
| cbiA | NP_460980.1 | 16765365 | *Salmonella typhimurium* |
| fldA | NP_459679.1 | 16764064 | *Salmonella typhimurium* |
| cobA | P31570.1 | 399274 | *Salmonella typhimurium* |
| cbiP | AAA27268.1 | 154436 | *Salmonella typhimurium* |
| cbiB | Q05600.1 | 543942 | *Salmonella typhimurium* |
| cobU | NP_460963.1 | 16765348 | *Salmonella typhimurium* |
| cobT | NP_460961.1 | 16765346 | *Salmonella typhimurium* |
| Cobs | AAA27270.1 | 154438 | *Salmonella typhimurium* |
| cobC | NP_459635.1 | 16764020 | *Salmonella typhimurium* |
| cysG | NP_462380.1 | 16766765 | *Salmonella typhimurium* |

Some organisms unable to synthesize $B_{12}$ de novo are able to catalyze some steps of the pathway. *E. coli*, for example, is unable to synthesize the corrin ring structure but encodes proteins that catalyze several reactions in the pathway (Raux et al., *J. Bacteriol.* 178:753-767 (1996)). The cysG gene encodes a functional CysG, a multifunctional enzyme that converts uroporphyrinogen III to precorrin-2 (Warren et al. 1990; Woodcock et al. 1998). The proteins encoded by cobTSU transform cobinamide to cobalamin and introduce the 5'-deoxyadenosyl group (Raux et al., *J. Bacteriol.* 178:753-767 (1996)).

| Protein | GenBank ID | GI Number | Organism |
|---|---|---|---|
| cobT | NP_416495.1 | 16129932 | *Escherichia coli* K12 sp. |
| cobs | NP_416496.1 | 16129933 | *Escherichia coli* K12 sp. |
| cobU | NP_416497.1 | 16129934 | *Escherichia coli* K12 sp. |
| cysG | NP_417827.1 | 16131246 | *Escherichia coli* K12 sp. |

*S. cerevisiae* is not able to synthesize $B_{12}$ de novo, nor is it able to uptake the vitamin at detectable levels. However, the *S. cerevisiae* genome encodes two proteins, Met1p and Met8p, that catalyze several $B_{12}$ pathway reactions. Met1p is analogous to the uroporphyrinogen III transmethylase CysG of *S. typhimurium*, which catalyzes the first step of B12 biosynthesis from uroporphyrinogen III (Raux et al., *Biochem. J.* 338(Pt 3): 701-708 (1999)). The Met8p protein is a bifunctional protein with uroporphyrinogen III transmethylase activity and cobaltochelatase activity analogous to the CysG of *B. megaterium* (Raux et al., supra (1999)).

| Protein | GenBank ID | GI Number | Organism |
|---|---|---|---|
| Met1p | NP_012995.1 | 6322922 | *Saccharomyces cerevisiae* |
| Met8p | NP_009772.1 | 6319690 | *Saccharomyces cerevisiae* |

Any or all of these genes can be introduced into an organism deficient or inefficient in one or more components of cobalamin synthesis to enable or increase the efficiency of cobalamin synthesis.

Example XV

Engineering Enhanced Cobalamin Uptake Capability in an Organism

This example describes engineering $B_{12}$ uptake capability into a host organism. $B_{12}$ uptake requires a specific transport system (Sennett et al., *Annu. Rev. Biochem.* 50:1053-1086 (1981)).

The $B_{12}$ transport system of *E. coli* has been extensively studied. High-affinity transport across the outer membrane is calcium-dependent and mediated by a 66 kDa outer membrane porin, BtuB (Heller et al., *J. Bacteria* 161:896-903 (1985)). BtuB interacts with the TonB energy transducing system (TonB-ExbB-ExbD), facilitating energy-dependent translocation and binding to periplasmic binding protein BtuF (Letain and Postle, 1997; Chimento et al. 2003). Transport across the inner membrane is facilitated by an ABC type uptake system composed of BtuF, BtuD (ATP binding component) and BtuC (permease) (Locher et al., *Science* 296:1091-1098 (2002)). Crystal structures of the BtuCDF complex are available (Hvorup et al., *Science* 317:1387-1390 (2007); Locher et al. supra). An additional protein, BtuE, is coexpressed in the btuCED operon, but this protein is not required for B12 transport and its function is unknown (Rioux and Kadner, *Mol. Gen. Genet.* 217:301-308 (1989)). The btuCED operon is constitutively expressed. The GenBank identifiers and GI numbers of the genes associated with $B_{12}$ transport are listed below.

| Protein | GenBank ID | GI Number | Organism |
|---|---|---|---|
| btuB | NP_418401.1 | 16131804 | *Escherichia coli* K12 sp. MG1655 |
| btuC | NP_416226.1 | 16129667 | *Escherichia coli* K12 sp. MG1655 |
| btuD | NP_416224.1 | 16129665 | *Escherichia coli* K12 sp. MG1655 |
| btuF | NP_414700.1 | 16128151 | *Escherichia coli* K12 sp. MG1655 |
| tonB | NP_415768.1 | 16129213 | *Escherichia coli* K12 sp. MG1655 |
| exbB | NP_417479.1 | 16130904 | *Escherichia coli* K12 sp. MG1655 |
| exbD | NP_417478.1 | 16130903 | *Escherichia coli* K12 sp. MG1655 |

The $B_{12}$ uptake capability of an organism can be further improved by overexpressing genes encoding the requisite transport proteins, and reducing or eliminating negative regulatory control. Overexpressing the btuBCDF genes leads to increased binding of B12 to membranes and increased rate of uptake into cells. Another strategy is to remove regulatory control. The btuB mRNA translation is directly repressed by B12 at the 5' UTR (Nahvi et al., *Chem. Biol.* 9:1043 (2002)). This interaction may induce mRNA folding to block ribosome access to the translational start. Mutation or elimination of the $B_{12}$ binding site removes inhibition and improves the efficiency of $B_{12}$ uptake (U.S. Pat. No. 6,432,686 (2002)). These strategies were successfully employed to improve $B_{12}$ uptake capability in 1,3-PDO producing microorganisms (WO/1999/058686) and (U.S. Pat. No. 6,432,686 (2002)). A recent patent application describes improving the efficiency of $B_{12}$ uptake (WO/2008/152016) by deleting negative regulatory proteins such as *C. glutamicum* btuR2.

*S. typhimurium* possesses both high and low affinity transporters for $B_{12}$. The high affinity transporter is encoded by btuB (Rioux and Kadner, *J. Bacteriol.* 171:2986-2993 (1989)). Like *E. coli* transport across the periplasmic membrane is predicted to occur via an ABC transport system, although this has not been characterized to date. The $B_{12}$ binding protein is encoded by btuD and btuE, and btuC is predicted to encode the permease.

| Protein | GenBank ID | GI Number | Organism |
|---|---|---|---|
| btuB | AAA27031.1 | 153891 | *Salmonella typhimurium* LT2 |
| btuC | NP_460306.1 | 16764691 | *Salmonella typhimurium* LT2 |
| btuD | NP_460308.1 | 16764693 | *Salmonella typhimurium* LT2 |
| btuE | AAL20266.1 | 16419860 | *Salmonella typhimurium* LT2 |

Any or all of these genes can be introduced into an organism deficient in one or more components of cobalamin uptake to enable or increase the efficienty cobalamin uptake.

Method for Quantifying $B_{12}$ in the Culture Medium.

To quantify the amount of $B_{12}$ in the culture medium, cell free samples are run on HPLC. Cobalamin quantification is achieved by comparing peak area ratios at 278 nm and 361 num with standards, then applying peak areas to standard curves of cobalamin.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A non-naturally occurring microbial organism comprising exogenous nucleic acid encoding enzymes carbon monoxide dehydrogenase and a malate dehydrogenase, said enzymes expressed in a sufficient amount to enhance the availability of reducing equivalents in the presence of carbon monoxide or hydrogen, thereby increasing the yield of redox-limited products via carbohydrate-based carbon feedstock.

2. The non-naturally occurring microbial organism of claim 1 further comprising one or more nucleic acids encoding an enzyme selected from a hydrogenase, an NAD(P)H:ferredoxin oxidoreductase, and a ferredoxin, a phosphoenolpyruvate carboxylase, a phosphoenolpyruvate carboxykinase, a pyruvate carboxylase, a malic enzyme, a fumarase, a fumarate reductase, a succinyl-CoA synthetase, and a succinyl-CoA transferase.

3. The non-naturally occurring microbial organism of claim 1 further comprising
(a) a 1,4-butanediol pathway, wherein said microbial organism comprises at least one exogenous nucleic acid encoding an enzyme selected from 1) Succinyl-CoA transferase, Succinyl-CoA synthetase, or Succinyl-CoA ligase, 2) Succinyl-CoA reductase (aldehyde forming), 3) 4-Hydroxybutyrate dehydrogenase, 4) 4-Hydroxybutyrate kinase, 5) Phosphotrans-4-hydroxybutyrylase, 6) 4-Hydroxybutyryl-CoA reductase (aldehyde forming), 7) 1,4-butanediol dehydrogenase, 8) Succinate reductase, 9) Succinyl-CoA reductase (alcohol forming), 10) 4-Hydroxybutyryl-CoA transferase, 4-Hydroxybutyryl-CoA hydrolase, or 4-Hydroxybutyryl-CoA synthetase, 11) 4-Hydroxybutyrate reductase, 12) 4-Hydroxybutyryl-phosphate reductase, and 13) 4-Hydroxybutyryl-CoA reductase (alcohol forming);
(b) a 1,3-butanediol pathway, wherein said microbial organism comprises at least one exogenous nucleic acid encoding an enzyme selected from 1) Succinyl-CoA transferase, Succinyl-CoA synthetase, or Succinyl-CoA ligase, 2) Succinyl-CoA reductase (aldehyde forming), 3) 4-Hydroxybutyrate dehydrogenase, 4) 4-Hydroxybutyrate kinase, 5) Phosphotrans-4-hydroxybutyrylase, 6) 4-Hydroxybutyryl-CoA dehydratase, 7) Crotonase, 8) 3-Hydroxybutyryl-CoA reductase (aldehyde forming), 9) 3-Hydroxybutyraldehyde reductase, 10) Succinate reductase, 11) Succinyl-CoA reductase (alcohol forming), 12) 4-Hydroxybutyryl-CoA transferase or 4-Hydroxybutyryl-CoA synthetase, 13) 3-Hydroxybutyryl-CoA reductase (alcohol forming), 14) 3-Hydroxybutyryl-CoA hydrolase, 3-Hydroxybutyryl-CoA synthetase, or 3-Hydroxybutyryl-CoA transferase, 15) 3-Hydroxybutyrate reductase; and/or
(c) a butanol pathway, wherein said microbial organism comprises at least one exogenous nucleic acid encoding an enzyme selected from 1) Succinyl-CoA transferase, Succinyl-CoA synthetase, or Succinyl-CoA ligase, 2) Succinyl-CoA reductase (aldehyde forming), 3) 4-Hydroxybutyrate dehydrogenase, 4) 4-Hydroxybutyrate kinase, 5) Phosphotrans-4-hydroxybutyrylase, 6) 4-Hydroxybutyryl-CoA dehydratase, 7) Butyryl-CoA dehydrogenase, 8) Butyryl-CoA reductase (aldehyde forming), 9) Butyraldehyde reductase, 10) Succinate reductase, 11) Succinyl-CoA reductase (alcohol forming), 12) 4-Hydroxybutyryl-CoA transferase or 4-Hydroxybutyryl-CoA synthetase, 13) Butyryl-CoA reductase (alcohol forming), 14) Butyryl-CoA hydrolase, Butyryl-CoA synthetase, or Butyryl-CoA transferase, 15) Butyrate reductase.

4. A method for enhancing the availability of reducing equivalents, the method comprising culturing the non-naturally occurring microbial organism of claim 1 with a carbohydrate-based carbon feedstock in the presence of carbon monoxide or hydrogen under conditions and for a sufficient period of time to produce the product, thereby increasing the yield of a redox-limited product.

* * * * *